(12) United States Patent
Lipkens et al.

(10) Patent No.: US 10,704,021 B2
(45) Date of Patent: *Jul. 7, 2020

(54) ACOUSTIC PERFUSION DEVICES

(71) Applicant: FloDesign Sonics, Inc., Wilbraham, MA (US)

(72) Inventors: Bart Lipkens, Bloomfield, CT (US); Benjamin Ross-Johnsrud, Northampton, MA (US); Erik Miller, Belchertown, MA (US); Mark Brower, Wilbraham, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/947,770

(22) Filed: Apr. 6, 2018

(65) Prior Publication Data
US 2018/0298323 A1    Oct. 18, 2018

Related U.S. Application Data

(63) Continuation-in-part of application No. 15/696,176, filed on Sep. 5, 2017, which is a continuation of
(Continued)

(51) Int. Cl.
*B01D 17/06* (2006.01)
*C12M 1/00* (2006.01)
(Continued)

(52) U.S. Cl.
CPC ............. *C12M 47/02* (2013.01); *B01D 17/04* (2013.01); *B01D 17/06* (2013.01);
(Continued)

(58) Field of Classification Search
CPC ...... B01D 29/115; B01D 37/00; B01D 29/52; B01D 29/865; B01D 2201/0415;
(Continued)

(56) References Cited

U.S. PATENT DOCUMENTS 1,016,731 A   2/1912  Bennis et al.
1,017,524 A   2/1912  Ferguson
(Continued)

FOREIGN PATENT DOCUMENTS

AU     2002236405    9/2002
CN     105 087 788 A    11/2015
(Continued)

OTHER PUBLICATIONS

Alvarez et al.; Shock Waves, vol. 17, No. 6, pp. 441-447, 2008.
(Continued)

*Primary Examiner* — Cameron J Allen
(74) *Attorney, Agent, or Firm* — FloDesign Sonics, Inc.

(57) ABSTRACT

Acoustic perfusion devices and processes for separating biomolecules from other material in a fluid mixture are disclosed. The devices include an inlet port, an outlet port, and a collection port that are connected to an acoustic chamber. An ultrasonic transducer creates an acoustic standing wave in the acoustic chamber that permits a continuous flow of fluid to be recovered through the collection port while keeping the biological cells within the acoustic chamber to be returned to the bioreactor from which the fluid mixture is being drawn.

17 Claims, 38 Drawing Sheets

Related U.S. Application Data application No. 15/139,187, filed on Apr. 26, 2016, now Pat. No. 9,752,113, which is a continuation-in-part of application No. 14/975,307, filed on Dec. 18, 2015, now Pat. No. 9,822,333, and a continuation-in-part of application No. 14/175,766, filed on Feb. 7, 2014, now Pat. No. 9,416,344, and a continuation-in-part of application No. 14/026,413, filed on Sep. 13, 2013, now Pat. No. 9,458,450, which is a continuation-in-part of application No. 13/844,754, filed on Mar. 15, 2013, now Pat. No. 10,040,011.

(60) Provisional application No. 62/563,068, filed on Sep. 26, 2017, provisional application No. 62/482,681, filed on Apr. 6, 2017, provisional application No. 62/256,952, filed on Nov. 18, 2015, provisional application No. 62/243,211, filed on Oct. 19, 2015, provisional application No. 62/211,057, filed on Aug. 28, 2015, provisional application No. 62/093,491, filed on Dec. 18, 2014, provisional application No. 61/611,159, filed on Mar. 15, 2012, provisional application No. 61/611,240, filed on Mar. 15, 2012, provisional application No. 61/754,792, filed on Jan. 21, 2013, provisional application No. 61/708,641, filed on Oct. 2, 2012, provisional application No. 61/761,717, filed on Feb. 7, 2013.

(51) Int. Cl.
| | | |
|---|---|---|
| *B01D 17/04* | (2006.01) | |
| *B01D 21/28* | (2006.01) | |
| *B06B 1/06* | (2006.01) | |
| *C12M 1/26* | (2006.01) | |
| *C12M 1/42* | (2006.01) | |
| *C12N 13/00* | (2006.01) | |
| *B01D 21/24* | (2006.01) | |
| *H01L 41/09* | (2006.01) | |

(52) U.S. Cl.
CPC ........ *B01D 21/2411* (2013.01); *B01D 21/283* (2013.01); *B06B 1/0644* (2013.01); *C12M 29/10* (2013.01); *C12M 29/18* (2013.01); *C12M 33/08* (2013.01); *C12M 35/04* (2013.01); *C12N 13/00* (2013.01); *H01L 41/0973* (2013.01)

(58) Field of Classification Search
CPC ........ B01D 2201/0446; B01D 2201/12; B01D 17/04; B01D 17/06; B01D 21/283; C12M 47/02; C12M 29/18; C12M 29/10; C12M 33/08; C12M 35/04; C12N 13/00; C12N 1/02; B06B 1/0644; H01L 41/0973
See application file for complete search history.

(56) References Cited

U.S. PATENT DOCUMENTS

| | | |
|---|---|---|
| 1,035,754 A | 8/1912 | Shook |
| 2,473,971 A | 6/1949 | Ross |
| 2,667,944 A | 2/1954 | Crites |
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,125,789 A | 11/1978 | Van Schoiack |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,211,949 A | 7/1980 | Brisken |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,484,907 A | 11/1984 | Sheeran, Jr. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,429 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,562,823 A | 10/1996 | Reeves |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,844,140 A | 12/1998 | Seale |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,029,518 A | 2/2000 | Oeftering |
| 6,090,295 A | 6/2000 | Raghavarao et al. |
| 6,166,231 A | 12/2000 | Hoeksema |
| 6,216,538 B1 | 4/2001 | Yasuda et al. |
| 6,205,848 B1 | 6/2001 | Faber et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,235,227 B2 | 6/2007 | Lanza et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |

(56) References Cited

U.S. PATENT DOCUMENTS

| | | |
|---|---|---|
| 7,541,166 B2 | 6/2009 | Belgrader et al. |
| 7,601,267 B2 | 10/2009 | Haake et al. |
| 7,673,516 B2 | 3/2010 | Janssen et al. |
| 7,674,630 B2 | 3/2010 | Siversson |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,865,003 B2 | 10/2014 | Yang |
| 8,873,051 B2 | 10/2014 | Kaduchak et al. |
| 8,889,388 B2 | 11/2014 | Wang et al. |
| 9,023,658 B2 | 5/2015 | Gauer et al. |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,375,662 B2 | 6/2016 | Kambayashi et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,618 B2 | 1/2018 | Hoyos |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehl et al. |
| 9,944,702 B2 | 4/2018 | Galetto |
| 9,944,709 B2 | 4/2018 | Galetto |
| 9,947,431 B2 | 4/2018 | El-Zahab et al. |
| 9,974,898 B2 | 5/2018 | Spain et al. |
| 9,983,459 B2 | 5/2018 | Arnold |
| 10,006,052 B2 | 6/2018 | Jarjour |
| 10,045,913 B2 | 8/2018 | Warner |
| 10,046,028 B2 | 8/2018 | Gregory |
| 10,046,037 B2 | 8/2018 | Weinschenk et al. |
| 10,047,116 B2 | 8/2018 | Morein |
| 10,047,123 B2 | 8/2018 | Weinschenk et al. |
| 10,047,124 B2 | 8/2018 | Weinschenk et al. |
| 10,047,144 B2 | 8/2018 | Elson et al. |
| 10,047,365 B2 | 8/2018 | Williams |
| 10,047,451 B2 | 8/2018 | Gaben |
| 10,047,650 B2 | 8/2018 | Abram |
| 10,052,427 B2 | 8/2018 | Flieg |
| 10,052,431 B2 | 8/2018 | Dreschel |
| 10,052,631 B2 | 8/2018 | Ben-Yakar et al. |
| 10,071,148 B2 | 9/2018 | Weinschenk |
| 10,071,383 B2 | 9/2018 | Dionne |
| 10,072,062 B2 | 9/2018 | Collingwood |
| 10,073,098 B2 | 9/2018 | Wong |
| 10,076,574 B2 | 9/2018 | Wang |
| 10,160,786 B1 | 12/2018 | Weinschenk et al. |
| 10,166,255 B2 | 1/2019 | Moriarity et al. |
| 10,166,323 B2 | 1/2019 | Fiering et al. |
| 10,167,474 B2 | 1/2019 | Rossi et al. |
| 10,167,478 B2 | 1/2019 | Williams |
| 10,190,113 B2 | 1/2019 | Forsyth |
| 10,190,137 B2 | 1/2019 | Zhang et al. |
| 10,195,605 B2 | 2/2019 | Reinbigler |
| 10,196,608 B2 | 2/2019 | Poirot |
| 10,196,651 B2 | 2/2019 | Conway et al. |
| 10,196,652 B2 | 2/2019 | Conway et al. |
| 10,201,365 B2 | 2/2019 | Boudreaux et al. |
| 10,201,652 B2 | 2/2019 | Dutra et al. |
| 10,202,457 B2 | 2/2019 | Ruiz-Opazo et al. |

(56) References Cited

U.S. PATENT DOCUMENTS

| | | |
|---|---|---|
| 10,202,762 B2 | 2/2019 | Sollohub |
| 10,208,300 B2 | 2/2019 | Messina et al. |
| 10,214,013 B2 | 2/2019 | Foresti et al. |
| 10,214,718 B2 | 2/2019 | Berteau et al. |
| 10,215,760 B2 | 2/2019 | Grove |
| 10,221,843 B2 | 3/2019 | Locker |
| 10,224,015 B2 | 3/2019 | Hsu |
| 10,236,797 B2 | 3/2019 | Wischnewskiy |
| 10,238,365 B2 | 3/2019 | Shiraishi |
| 10,238,741 B2 | 3/2019 | Creusot |
| 10,239,058 B2 | 3/2019 | Lavieu et al. |
| 10,239,948 B2 | 3/2019 | Jullerat et al. |
| 10,245,064 B2 | 4/2019 | Rhee et al. |
| 10,251,664 B2 | 4/2019 | Shelton et al. |
| 10,253,296 B2 | 4/2019 | Kahvejian et al. |
| 10,254,212 B2 | 4/2019 | Ward |
| 10,254,401 B2 | 4/2019 | Suyama |
| 10,258,698 B2 | 4/2019 | Hoge et al. |
| 10,261,078 B2 | 4/2019 | Branch |
| 10,272,163 B2 | 4/2019 | Laterza |
| 10,272,412 B2 | 4/2019 | Rubio Martinez et al. |
| 10,273,283 B2 | 4/2019 | Springer et al. |
| 10,286,007 B2 | 5/2019 | Galetto et al. |
| 10,308,928 B2 | 6/2019 | Lipkens et al. |
| 10,316,063 B1 | 6/2019 | Weinschenk et al. |
| 10,316,101 B2 | 6/2019 | Galetto et al. |
| 10,322,949 B2 | 6/2019 | Lipkens et al. |
| 10,323,065 B1 | 6/2019 | Weinschenk et al. |
| 10,323,076 B2 | 6/2019 | Ellsworth et al. |
| 10,324,082 B2 | 6/2019 | Taylor et al. |
| 10,326,383 B2 | 6/2019 | Stiebel et al. |
| 10,329,531 B2 | 6/2019 | Kahvejian et al. |
| 10,334,390 B2 | 6/2019 | Bakish |
| 10,342,829 B2 | 7/2019 | Smith et al. |
| 10,343,187 B2 | 7/2019 | Doyle et al. |
| 10,344,051 B2 | 7/2019 | Bracewell et al. |
| 10,344,263 B2 | 7/2019 | Kahvejian et al. |
| 10,350,514 B2 | 7/2019 | Lipkens et al. |
| 10,357,766 B2 | 7/2019 | Raghen et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057886 A1 | 3/2004 | Jona Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0055136 A1 | 3/2005 | Hoffman |
| 2005/0121269 A1 | 6/2005 | Namduri |
| 2005/0145567 A1 | 7/2005 | Quintel et al. |
| 2005/0196725 A1 | 9/2005 | Fu |
| 2005/0239198 A1 | 10/2005 | Kunas |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0035568 A1* | 2/2008 | Huang .......... B01D 63/02 210/646 |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0042253 A1 | 2/2009 | Hiller et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0226994 A1 | 9/2009 | Lemor et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0161903 A1 | 6/2012 | Thomas et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0206688 A1 | 8/2013 | El-Naas |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0309757 A1 | 11/2013 | Sung-Chun Kim |
| 2013/0316412 A1 | 11/2013 | Schultz |
| 2014/0011240 A1 | 1/2014 | Lipkens et al. |
| 2014/0017758 A1 | 1/2014 | Kniep et al. |
| 2014/0033808 A1 | 2/2014 | Ding et al. |
| 2014/0046181 A1 | 2/2014 | Benchimol et al. |
| 2014/0102947 A1 | 4/2014 | Baym et al. |
| 2014/0141413 A1 | 5/2014 | Laugharn, Jr. et al. |
| 2014/0154795 A1 | 6/2014 | Lipkens et al. |
| 2014/0193381 A1 | 7/2014 | Warner et al. |
| 2014/0230912 A1 | 8/2014 | Aider et al. |
| 2014/0319077 A1 | 10/2014 | Lipkens et al. |

(56) References Cited

U.S. PATENT DOCUMENTS

| | | |
|---|---|---|
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0287778 A1 | 10/2016 | Leach et al. |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0291122 A1 | 10/2017 | Lipkens et al. |
| 2017/0298316 A1* | 10/2017 | Kennedy, III ......... C12M 35/04 |
| 2017/0369865 A1* | 12/2017 | Lipkens ................. C12N 13/00 |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |
| 2018/0001011 A1 | 1/2018 | Paschon et al. |
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0010758 A1 | 1/2018 | Mochizuki |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |

(56) References Cited

U.S. PATENT DOCUMENTS

| | | |
|---|---|---|
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea et al. |
| 2018/0119174 A1 | 5/2018 | Scharenberg et al. |
| 2018/0130491 A1 | 5/2018 | Mathur |
| 2018/0136167 A1 | 5/2018 | Smith et al. |
| 2018/0140758 A1 | 5/2018 | Vincent et al. |
| 2018/0143138 A1 | 5/2018 | Shreve et al. |
| 2018/0147245 A1 | 5/2018 | O'Shea et al. |
| 2018/0147576 A1 | 5/2018 | Lavieu et al. |
| 2018/0148740 A1 | 5/2018 | Conway |
| 2018/0148763 A1 | 5/2018 | Shimada et al. |
| 2018/0153946 A1 | 6/2018 | Alemany et al. |
| 2018/0155716 A1 | 6/2018 | Zhang et al. |
| 2018/0157107 A1 | 6/2018 | Koyama |
| 2018/0161775 A1 | 6/2018 | Kapur et al. |
| 2018/0177490 A1 | 6/2018 | Shiraishi |
| 2018/0178184 A1 | 6/2018 | Holland |
| 2018/0180610 A1 | 6/2018 | Taha |
| 2018/0223256 A1 | 8/2018 | Kim |
| 2018/0223273 A1 | 8/2018 | Lipkens |
| 2018/0223439 A1 | 8/2018 | Lipkens |
| 2018/0230433 A1 | 8/2018 | Kokkaliaris |
| 2018/0231555 A1 | 8/2018 | Davis |
| 2018/0236103 A1 | 8/2018 | Friedland |
| 2018/0236280 A1 | 8/2018 | Lipkens Bart et al. |
| 2018/0237533 A1 | 8/2018 | Juillerat et al. |
| 2018/0237768 A1 | 8/2018 | Reik |
| 2018/0237798 A1 | 8/2018 | Duchateau et al. |
| 2018/0243382 A1 | 8/2018 | Wang |
| 2018/0243665 A1 | 8/2018 | Lacki |
| 2018/0244722 A1 | 8/2018 | Stickel |
| 2018/0246103 A1 | 8/2018 | Lipkens |
| 2018/0249688 A1 | 9/2018 | Ayares |
| 2018/0250424 A1 | 9/2018 | Cotta-Ramusino |
| 2018/0251723 A1 | 9/2018 | Murthy |
| 2018/0251770 A1 | 9/2018 | Friedland |
| 2018/0255751 A1 | 9/2018 | Regev |
| 2018/0256922 A1 | 9/2018 | Mittelstein |
| 2018/0257042 A1 | 9/2018 | Hester |
| 2018/0257076 A1 | 9/2018 | Weitz |
| 2018/0258160 A1 | 9/2018 | Lai |
| 2018/0258955 A1 | 9/2018 | Levasseur |
| 2018/0258957 A1 | 9/2018 | Levasseur |
| 2018/0296954 A1 | 10/2018 | Trampler |
| 2018/0353614 A1 | 12/2018 | Peters |
| 2018/0361053 A1 | 12/2018 | Fiering et al. |
| 2018/0361383 A1 | 12/2018 | Kapur et al. |
| 2018/0361384 A1 | 12/2018 | Kapur et al. |
| 2018/0369816 A1 | 12/2018 | Ai |
| 2018/0371418 A1 | 12/2018 | Yang et al. |
| 2019/0000932 A1 | 1/2019 | Martini |
| 2019/0000933 A1 | 1/2019 | Martini |
| 2019/0000947 A1 | 1/2019 | Weinschenk et al. |
| 2019/0000959 A1 | 1/2019 | Ciaramella et al. |
| 2019/0000982 A1 | 1/2019 | Wang et al. |
| 2019/0002497 A1 | 1/2019 | Stickel et al. |
| 2019/0002504 A1 | 1/2019 | Weinschenk et al. |
| 2019/0002561 A1 | 1/2019 | Galetto |
| 2019/0002573 A1 | 1/2019 | Galetto |
| 2019/0002578 A1 | 1/2019 | Brayshaw et al. |
| 2019/0002589 A1 | 1/2019 | Bardroff et al. |
| 2019/0002890 A1 | 1/2019 | Martini et al. |
| 2019/0004052 A1 | 1/2019 | Herd et al. |
| 2019/0008943 A1 | 1/2019 | Poolman et al. |
| 2019/0008948 A1 | 1/2019 | Ciaramella et al. |
| 2019/0010190 A1 | 1/2019 | Weinschenk et al. |
| 2019/0010192 A1 | 1/2019 | Binder et al. |
| 2019/0010471 A1 | 1/2019 | Zhang et al. |
| 2019/0010495 A1 | 1/2019 | Boitano et al. |
| 2019/0010514 A1 | 1/2019 | Poirot et al. |
| 2019/0011407 A9 | 1/2019 | Lipkens et al. |
| 2019/0015501 A1 | 1/2019 | Ciaramella et al. |
| 2019/0016753 A1 | 1/2019 | Jang et al. |
| 2019/0016767 A1 | 1/2019 | Shah |
| 2019/0016781 A1 | 1/2019 | Bolen |
| 2019/0021729 A1 | 1/2019 | Smith et al. |
| 2019/0022019 A1 | 1/2019 | Martini |
| 2019/0023577 A1 | 1/2019 | Feng |
| 2019/0024114 A1 | 1/2019 | Bauer |
| 2019/0030073 A1 | 1/2019 | Kalayoglu |
| 2019/0030151 A1 | 1/2019 | Jones et al. |
| 2019/0030533 A1 | 1/2019 | Shachar et al. |
| 2019/0031780 A1 | 1/2019 | Eavarone et al. |
| 2019/0031999 A1 | 1/2019 | Suresh et al. |
| 2019/0032036 A1 | 1/2019 | Zhang |
| 2019/0032052 A1 | 1/2019 | Zhang |
| 2019/0036152 A1 | 1/2019 | Gaben et al. |
| 2019/0036172 A1 | 1/2019 | Gaben et al. |
| 2019/0006036 A1 | 2/2019 | Moriarty et al. |
| 2019/0038671 A1 | 2/2019 | Fan et al. |
| 2019/0039060 A1 | 2/2019 | Chien et al. |
| 2019/0040099 A1 | 2/2019 | Brellisford et al. |
| 2019/0040117 A1 | 2/2019 | Elson et al. |
| 2019/0040414 A1 | 2/2019 | Wu |
| 2019/0046986 A1 | 2/2019 | Yuan et al. |
| 2019/0048060 A1 | 2/2019 | Conway et al. |
| 2019/0048061 A1 | 2/2019 | Smeland et al. |
| 2019/0054112 A1 | 2/2019 | Gregoire |
| 2019/0054119 A1 | 2/2019 | Alma et al. |
| 2019/0054122 A1 | 2/2019 | Moriarity et al. |
| 2019/0055286 A1 | 2/2019 | Walz et al. |
| 2019/0055509 A1 | 2/2019 | Meacham et al. |
| 2019/0056302 A1 | 2/2019 | Berezin et al. |
| 2019/0056399 A1 | 2/2019 | Wong et al. |
| 2019/0060363 A1 | 2/2019 | Moriarity et al. |
| 2019/0062185 A1 | 2/2019 | Amouzadeh et al. |
| 2019/0062690 A1 | 2/2019 | Tostoes et al. |
| 2019/0062735 A1 | 2/2019 | Welstead et al. |
| 2019/0064146 A1 | 2/2019 | Glick |
| 2019/0067554 A1 | 2/2019 | Karrai et al. |
| 2019/0070233 A1 | 3/2019 | Yeung |
| 2019/0070528 A1 | 3/2019 | Luthe |
| 2019/0071695 A1 | 3/2019 | Wagner |
| 2019/0071717 A1 | 3/2019 | Zhang et al. |
| 2019/0076473 A1 | 3/2019 | Nguyen |
| 2019/0076769 A1 | 3/2019 | Meacham et al. |
| 2019/0078133 A1 | 3/2019 | Cavanagh et al. |
| 2019/0079070 A1 | 3/2019 | Shiffman et al. |
| 2019/0083533 A1 | 3/2019 | Soon-Shiong et al. |
| 2019/0085067 A1 | 3/2019 | Schurpf et al. |
| 2019/0085082 A1 | 3/2019 | Bicknell |
| 2019/0085381 A1 | 3/2019 | Neely et al. |
| 2019/0090900 A1 | 3/2019 | Rhee et al. |
| 2019/0091683 A1 | 3/2019 | Baudoin et al. |
| 2019/0092794 A1 | 3/2019 | Rubio Martinez et al. |
| 2019/0092865 A1 | 3/2019 | Ruiz-Opazo |
| 2019/0093097 A1 | 3/2019 | Madison et al. |
| 2019/0094185 A1 | 3/2019 | Athanassiadis |
| 2019/0101541 A1 | 4/2019 | Wandall et al. |
| 2019/0105043 A1 | 4/2019 | Jaworek et al. |
| 2019/0106039 A1 | 4/2019 | Winton et al. |
| 2019/0106710 A1 | 4/2019 | Zhang et al. |
| 2019/0107420 A1 | 4/2019 | Kincel |
| 2019/0111480 A1 | 4/2019 | Barbati et al. |
| 2019/0119387 A1 | 4/2019 | Brett |
| 2019/0119701 A1 | 4/2019 | Liang et al. |
| 2019/0125839 A1 | 5/2019 | Frederick et al. |

(56) References Cited

U.S. PATENT DOCUMENTS

| | | |
|---|---|---|
| 2019/0127685 A1 | 5/2019 | Fattah et al. |
| 2019/0133633 A1 | 5/2019 | Neurohr et al. |
| 2019/0135942 A1 | 5/2019 | Duthe et al. |
| 2019/0136261 A1 | 5/2019 | Conway |
| 2019/0143013 A1 | 5/2019 | Vincent et al. |
| 2019/0153027 A1 | 5/2019 | Natarajan et al. |
| 2019/0153106 A1 | 5/2019 | Ruiz-Opazo et al. |
| 2019/0160463 A1 | 5/2019 | Ai et al. |
| 2019/0161540 A1 | 5/2019 | Gearing et al. |
| 2019/0167722 A1 | 6/2019 | Soon-Shiong et al. |
| 2019/0169233 A1 | 6/2019 | Weinschenk et al. |
| 2019/0169597 A1 | 6/2019 | Astrakhan et al. |
| 2019/0169639 A1 | 6/2019 | Zhang et al. |
| 2019/0170745 A1 | 6/2019 | Hu et al. |
| 2019/0173129 A1 | 6/2019 | Gaben et al. |
| 2019/0175517 A1 | 6/2019 | Martini et al. |
| 2019/0175651 A1 | 6/2019 | Lee et al. |
| 2019/0176150 A1 | 6/2019 | Kapur et al. |
| 2019/0177368 A1 | 6/2019 | Weinschenk et al. |
| 2019/0177369 A1 | 6/2019 | Weinschenk et al. |
| 2019/0183931 A1 | 6/2019 | Alice et al. |
| 2019/0184035 A1 | 6/2019 | Jarjour et al. |
| 2019/0184312 A1 | 6/2019 | Liu et al. |
| 2019/0184326 A1 | 6/2019 | Davis et al. |
| 2019/0185860 A1 | 6/2019 | Kim et al. |
| 2019/0191252 A1 | 6/2019 | Lipkens et al. |
| 2019/0192653 A1 | 6/2019 | Hoge |
| 2019/0194049 A1 | 6/2019 | Lindemann |
| 2019/0194087 A1 | 6/2019 | Larsen |
| 2019/0194340 A1 | 6/2019 | Emtage et al. |
| 2019/0194617 A1 | 6/2019 | Emtage et al. |
| 2019/0199312 A1 | 6/2019 | Dasgupta et al. |
| 2019/0199322 A1 | 6/2019 | Dasgupta et al. |
| 2019/0201041 A1 | 7/2019 | Kimball et al. |
| 2019/0201047 A1 | 7/2019 | Yates et al. |
| 2019/0201048 A1 | 7/2019 | Nguyen et al. |
| 2019/0209616 A1 | 7/2019 | Galetto et al. |
| 2019/0211109 A1 | 7/2019 | Peshwa et al. |
| 2019/0218254 A1 | 7/2019 | Weinschenk et al. |
| 2019/0218602 A1 | 7/2019 | Zhang et al. |
| 2019/0225694 A1 | 7/2019 | Zien et al. |
| 2019/0225990 A1 | 7/2019 | Adbudl-Manan et al. |
| 2019/0290201 A1 | 7/2019 | Boudreaux et al. |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 501 A1 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| EP | 2675901 | 5/2018 |
| EP | 2956772 | 5/2018 |
| EP | 3323444 | 5/2018 |
| EP | 3324996 | 5/2018 |
| EP | 3327127 | 5/2018 |
| EP | 3337819 | 6/2018 |
| EP | 2772196 | 8/2018 |
| EP | 2882091 | 8/2018 |
| EP | 2910568 | 8/2018 |
| EP | 3265805 | 8/2018 |
| EP | 3359676 | 8/2018 |
| EP | 3360955 | 8/2018 |
| EP | 3361252 | 8/2018 |
| EP | 3362102 | 8/2018 |
| EP | 3363456 | 8/2018 |
| EP | 3363813 | 8/2018 |
| EP | 3365062 | 8/2018 |
| EP | 3365095 | 8/2018 |
| EP | 3365441 | 8/2018 |
| EP | 3365447 | 8/2018 |
| EP | 3366696 | 8/2018 |
| EP | 3367118 | 8/2018 |
| EP | 2931892 | 9/2018 |
| EP | 3019606 | 9/2018 |
| EP | 3089800 | 9/2018 |
| EP | 3123534 | 9/2018 |
| EP | 3368528 | 9/2018 |
| EP | 3368670 | 9/2018 |
| EP | 3371295 | 9/2018 |
| EP | 3372813 | 9/2018 |
| EP | 3372814 | 9/2018 |
| EP | 2535355 | 1/2019 |
| EP | 2922902 | 1/2019 |
| EP | 3004338 | 1/2019 |
| EP | 3421975 | 1/2019 |
| EP | 3423092 | 1/2019 |
| EP | 3423580 | 1/2019 |
| EP | 3425386 | 1/2019 |
| EP | 3426271 | 1/2019 |
| EP | 3426372 | 1/2019 |
| EP | 3426375 | 1/2019 |
| EP | 3426690 | 1/2019 |
| EP | 3427815 | 1/2019 |
| EP | 3429753 | 1/2019 |
| EP | 3430050 | 1/2019 |
| EP | 3430134 | 1/2019 |
| EP | 3430146 | 1/2019 |
| EP | 3430463 | 1/2019 |
| EP | 3433363 | 1/2019 |
| EP | 3433366 | 1/2019 |
| EP | 3434774 | 1/2019 |
| EP | 3434776 | 1/2019 |
| EP | 2598533 | 2/2019 |

(56) References Cited

FOREIGN PATENT DOCUMENTS

| | | |
|---|---|---|
| EP | 2691422 | 2/2019 |
| EP | 2925431 | 2/2019 |
| EP | 3170185 | 2/2019 |
| EP | 3436030 | 2/2019 |
| EP | 3436196 | 2/2019 |
| EP | 3436575 | 2/2019 |
| EP | 3436579 | 2/2019 |
| EP | 3437740 | 2/2019 |
| EP | 3439698 | 2/2019 |
| EP | 3440191 | 2/2019 |
| EP | 3441468 | 2/2019 |
| EP | 3442598 | 2/2019 |
| EP | 3443002 | 2/2019 |
| EP | 3443084 | 2/2019 |
| EP | 3445407 | 2/2019 |
| EP | 3445848 | 2/2019 |
| EP | 3445853 | 2/2019 |
| EP | 3445856 | 2/2019 |
| EP | 2694091 | 3/2019 |
| EP | 3080260 | 3/2019 |
| EP | 3448291 | 3/2019 |
| EP | 3448995 | 3/2019 |
| EP | 3449850 | 3/2019 |
| EP | 3452133 | 3/2019 |
| EP | 3452499 | 3/2019 |
| EP | 3453406 | 3/2019 |
| EP | 3456339 | 3/2019 |
| EP | 3458081 | 3/2019 |
| EP | 3458083 | 3/2019 |
| EP | 3458104 | 3/2019 |
| EP | 3458105 | 3/2019 |
| EP | 3458107 | 3/2019 |
| EP | 3458108 | 3/2019 |
| EP | 3458590 | 3/2019 |
| EP | 3066115 | 4/2019 |
| EP | 3119807 | 4/2019 |
| EP | 3186281 | 4/2019 |
| EP | 3361252 | 4/2019 |
| EP | 3463433 | 4/2019 |
| EP | 3463660 | 4/2019 |
| EP | 3464198 | 4/2019 |
| EP | 3464594 | 4/2019 |
| EP | 3467276 | 4/2019 |
| EP | 3467491 | 4/2019 |
| EP | 3468225 | 4/2019 |
| EP | 3468351 | 4/2019 |
| EP | 3468594 | 4/2019 |
| EP | 3470089 | 4/2019 |
| EP | 3470519 | 4/2019 |
| EP | 3471621 | 4/2019 |
| EP | 3473707 | 4/2019 |
| EP | 2546144 | 5/2019 |
| EP | 3311588 | 5/2019 |
| EP | 3474904 | 5/2019 |
| EP | 3475307 | 5/2019 |
| EP | 3481361 | 5/2019 |
| EP | 3481867 | 5/2019 |
| EP | 2412817 | 6/2019 |
| EP | 3490562 | 6/2019 |
| EP | 3490574 | 6/2019 |
| EP | 3490694 | 6/2019 |
| EP | 3490712 | 6/2019 |
| EP | 3490801 | 6/2019 |
| EP | 3491124 | 6/2019 |
| EP | 3491126 | 6/2019 |
| EP | 3493836 | 6/2019 |
| EP | 3493907 | 6/2019 |
| EP | 3495376 | 6/2019 |
| EP | 3495811 | 6/2019 |
| EP | 3498846 | 6/2019 |
| EP | 3500244 | 6/2019 |
| EP | 3500271 | 6/2019 |
| EP | 3500297 | 6/2019 |
| EP | 3500659 | 6/2019 |
| EP | 3500696 | 6/2019 |
| EP | 3501619 | 6/2019 |
| EP | 3502137 | 6/2019 |
| EP | 3502253 | 6/2019 |
| EP | 3EP510161 | 7/2019 |
| EP | 2680877 | 7/2019 |
| EP | 2996789 | 7/2019 |
| EP | 3068535 | 7/2019 |
| EP | 3140319 | 7/2019 |
| EP | 3277333 | 7/2019 |
| EP | 3505098 | 7/2019 |
| EP | 3511342 | 7/2019 |
| EP | 3511420 | 7/2019 |
| EP | 3512540 | 7/2019 |
| GB | 2 420 510 A | 5/2006 |
| JP | H02-290266 | 11/1990 |
| JP | 9-136090 | 5/1997 |
| JP | H11-090110 | 4/1999 |
| JP | 2005-249267 | 12/2005 |
| KR | 1442486 | 9/2014 |
| RU | 2037327 C1 | 6/1995 |
| RU | 94015846 | 6/1996 |
| RU | 2067079 | 9/1996 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/130321 | 10/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043046 | 3/2013 |
| WO | WO 2013/043297 A1 | 3/2013 |
| WO | WO 2013030691 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/035457 | 3/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2014/165177 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/011519 | 1/2017 |
| WO | WO 2017/021543 | 2/2017 |
| WO | WO 2017/041102 | 3/2017 |
| WO | WO 20174201349 | 11/2017 |
| WO | WO 201721871 4 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |

(56) References Cited

FOREIGN PATENT DOCUMENTS

| | | |
|---|---|---|
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO 2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018058275 | 5/2018 |
| WO | WO 2018081476 | 5/2018 |
| WO | WO 2018091879 | 5/2018 |
| WO | WO2018094244 | 5/2018 |
| WO | WO 20180814701 | 5/2018 |
| WO | WO 2018098671 | 6/2018 |
| WO | WO 2018102752 | 6/2018 |
| WO | WO 2018106163 | 6/2018 |
| WO | WO 2018112145 | 6/2018 |
| WO | WO 2018112335 | 6/2018 |
| WO | WO 2018138385 | 8/2018 |
| WO | WO 2018140573 | 8/2018 |
| WO | WO 2018140845 | 8/2018 |
| WO | WO 2018142364 | 8/2018 |
| WO | WO 2018151811 | 8/2018 |
| WO | WO 2018151823 | 8/2018 |
| WO | WO 2018153772 | 8/2018 |
| WO | WO 2018160548 | 9/2018 |
| WO | WO 2018160909 | 9/2018 |
| WO | WO 2018160993 | 9/2018 |
| WO | WO 2018161017 | 9/2018 |
| WO | WO 2018161026 | 9/2018 |
| WO | WO 2018161038 | 9/2018 |
| WO | WO 2018161905 | 9/2018 |
| WO | WO 2018163183 | 9/2018 |
| WO | WO2018227286 | 12/2018 |
| WO | WO2018229612 | 12/2018 |
| WO | WO2018231990 | 12/2018 |
| WO | WO2018232045 | 12/2018 |
| WO | WO2018232131 | 12/2018 |
| WO | WO2018234421 | 12/2018 |
| WO | WO2018235228 | 12/2018 |
| WO | WO2018236708 | 12/2018 |
| WO | WO2018237201 | 12/2018 |
| WO | WO2018237239 | 12/2018 |
| WO | WO2018183966 | 1/2019 |
| WO | WO2019002551 | 1/2019 |
| WO | WO2019002633 | 1/2019 |
| WO | WO2019005155 | 1/2019 |
| WO | WO2019005866 | 1/2019 |
| WO | WO2019005871 | 1/2019 |
| WO | WO2019006418 | 1/2019 |
| WO | WO2019007869 | 1/2019 |
| WO | WO2019008335 | 1/2019 |
| WO | WO2019010422 | 1/2019 |
| WO | WO2019018423 | 1/2019 |
| WO | WO2019018491 | 1/2019 |
| WO | WO2019018796 | 1/2019 |
| WO | WO2019022671 | 1/2019 |
| WO | WO2019023523 | 1/2019 |
| WO | WO2019025661 | 2/2019 |
| WO | WO2019025984 | 2/2019 |
| WO | WO2019028172 | 2/2019 |
| WO | WO2019032675 | 2/2019 |
| WO | WO2019036382 | 2/2019 |
| WO | WO209048639 | 3/2019 |
| WO | WO2019041344 | 3/2019 |
| WO | WO2019046450 | 3/2019 |
| WO | WO2019048666 | 3/2019 |
| WO | WO2019051106 | 3/2019 |
| WO | WO2019051255 | 3/2019 |
| WO | WO2019051278 | 3/2019 |
| WO | WO2019051316 | 3/2019 |
| WO | WO2019051355 | 3/2019 |
| WO | WO2019055697 | 3/2019 |
| WO | WO2019055817 | 3/2019 |
| WO | WO2019055896 | 3/2019 |
| WO | WO2019056015 | 3/2019 |
| WO | WO2019057774 | 3/2019 |
| WO | WO2019058321 | 3/2019 |
| WO | WO2019058326 | 3/2019 |
| WO | WO2019060253 | 3/2019 |
| WO | WO2019060425 | 3/2019 |
| WO | WO2019060779 | 3/2019 |
| WO | WO2019067015 | 4/2019 |
| WO | WO2019069101 | 4/2019 |
| WO | WO2019070541 | 4/2019 |
| WO | WO2019070974 | 4/2019 |
| WO | WO2019072889 | 4/2019 |
| WO | WO2019075409 | 4/2019 |
| WO | WO2019079497 | 4/2019 |
| WO | WO2019079819 | 4/2019 |
| WO | WO2019080898 | 5/2019 |
| WO | WO2019081521 | 5/2019 |
| WO | WO2019094360 | 5/2019 |
| WO | WO2019098839 | 5/2019 |
| WO | WO2019099619 | 5/2019 |
| WO | WO2019099736 | 5/2019 |
| WO | WO2019099949 | 5/2019 |
| WO | WO2019101691 | 5/2019 |
| WO | WO2019101956 | 5/2019 |
| WO | WO201912655 | 6/2019 |
| WO | WO2018215686 | 6/2019 |
| WO | WO2019111250 | 6/2019 |
| WO | WO2019113310 | 6/2019 |
| WO | WO2019118475 | 6/2019 |
| WO | WO2019118885 | 6/2019 |
| WO | WO2019126329 | 6/2019 |
| WO | WO2019126558 | 6/2019 |
| WO | WO2019126724 | 6/2019 |
| WO | WO2019134007 | 7/2019 |
| WO | WO2019135843 | 7/2019 |
| WO | WO2019136288 | 7/2019 |
| WO | WO 2018231759 | 12/2019 |

OTHER PUBLICATIONS

Augustsson et al., Acoustophoretic microfluidic chip for sequential elution of surface bound molecules from beads or cells, Biomicrofluidics, Sep. 2012, 6(3):34115.

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

(56) References Cited

OTHER PUBLICATIONS

Chitale et al.; Understanding the Fluid Dynamics Associated with Macro Scale Ultrasonic Separators; Proceedings of Meetings on Acoustics, May 2015.
Cravotto et al.; Ultrasonics Sonochemistry, vol. 15, No. 5, pp. 898-902, 2008.
Ding, X et al., "Cell Separation Using Tilted-Angle Standing Surface Acoustic Waves", Proceedings of the National Academy of Sciences, Sep. 9, 2014, vol. 111, No. 36, pp. 12992-12997, See abstract; p. 12994, left col. p. 12995, left col. figure 1-3 and 6.
Ensminger et al; Ultrasonics Fundamentals, Technologies, and Applications; 2011.
Evander et al; Acoustofluidics 20: Applications in acoustic trapping, Lab Chip, 2012,12,4667-4676.
Evander et al; Acoustiofluidics 5: Building microfluidic acoustic resonators, Lab Chip, 2012, 12, 684.
Gallego-Juarez et al; "Piezoelectric ceramic and ultrasonic transducers"; Journal of Physics E: Scientific Instruments. 1989.
Ganguly et al; Essential Physics for Radiology and Imaging; Academic Publishers, Jan. 2016.
Garcia-Lopez, et al; Enhanced Acoustic Separation of Oil-Water Emulsion in Resonant Cavities. The Open Acoustics Journal. 2008, vol. 1, pp. 66-71.
Greenhall et al; Dynamic behavior of microscale particles controlled by standing bulk acoustic waves; Applied Physics Letters, 105, 144105 (2014).
Grenvall et al.; Concurrent Isolation of Lymphocytes and Granulocytes Using Prefocused Free Flow Acoustophoresis; Analytical Chemistry; vol. 87; pp. 5596-5604; 2015.
Gorenflo et al; Characterization and Optimization of Acoustic Filter Performance by Experimental DesignMethodology (whole document).
Gor'Koy et al; On the Forces Acting on a Small Particle in an Acoustical Field in an Ideal Fluid; Soviet Physics Doklady, vol. 6, p. 773.
Higginson et al.; Tunable optics derived from nonlinear acoustic effects; Journal of Applied Physics; vol. 95; No. 10; pp. 5896-5904; 2004.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Jin et al; Pharmaceutical Engineering; Jan. 2015; vol. 35 No. 1.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; Separation of bacterial spores from flowering water in macro-scale cavities by ultrasonic standing waves; submitted/ uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Musiak et al.; Design of a Control System for Acoustophoretic Separation, 2013 IEEE 56th International Midwest Symposium on Circuits and Systems (MWSCAS), Aug. 2013, pp. 1120-1123.
National Science Foundation, "Catalyzing Commercialization: putting sound to work for challenging separations", CEP, Sep. 2015, p. 14.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Nienow et al.; A potentially scalable method for the harvesting of hMSCs from microcarriers; Biochemical Engineering Journal 85 (2014) 79-88.
Pangu et al.; Droplet transport and coalescence kinetics in emulsions subjected to acoustic fields; Ultrasonics 46, pp. 289-302 (2007).
Phys. Org. "Engineers develop revolutionary nanotech water desalination membrane." Nov. 6, 2006. http://phys.org/news82047372.html.
Ponomarenko et al.; Density of states and zero Landau level probed through capacitance of graphene; Nature Nanotechnology Letters, Jul. 5, 2009; DOI: 10.1038/NNANO.2009.177.
"Proceedings of the Acoustics 2012 Nantes Conference," Apr. 23-27, 2012, Nantes, France, pp. 278-282.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Shitizu et al; "A Tutorial Review on Bioprocessing Systems Engineering" (whole document).
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-1196; 2012.
Woodside et al; Acoustic Force Distribution in Resonators for Ultrasonic Particle Separation; Biotechnology Laboratory and Dept of Chemical and Bio-Resource Engineering, University of British Columbia, Sep. 1998, vol. 44, No. 9.
Zhanqiu et al ;Culture Conditions and Types of Growth Media for Mammalian Cells (whole document).
Annex to Form PCT/ISA/206—Communication Relating to the Results of the Partial International Search Report dated Jul. 18, 2013.
European Search Report of European Application No. 11769474.5 dated Sep. 5, 2013.
European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.

(56) References Cited

OTHER PUBLICATIONS

International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/050729 dated Sep. 25, 2013.
International Search Report and Written Opinion for International Application No. PCT/US2013/059640 dated Feb. 18, 2014.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
European Search Report of European Application No. 12825592.4 dated Apr. 28, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.
International Search Report and Written Opinion for International Application No. PCT/US2018/026617, dated Jul. 4, 2018.
International Search Report and Written Opinion for International Application No. PCT/US2018/31267, dated Aug. 1, 2018.
European Search Report of European Application No. 15847217.5 dated Oct. 15, 2018.
International Search Report and Written Opinion for International Application No. PCT/US2017/057485, dated Apr. 23, 2019.
International Search Report and Written Opinion for International Application No. PCT/US18/65839, dated May 16, 2019.
International Search Report and Written Opinion for International Application No. PCT/US19/12950, dated May 24, 2019.
International Search Report and Written Opinion for International Application No. PCT/US18/63698, dated May 27, 2019.
International Search Report and Written Opinion for International Application No. PCT/US19/21492, dated Jun. 25, 2019.

\* cited by examiner

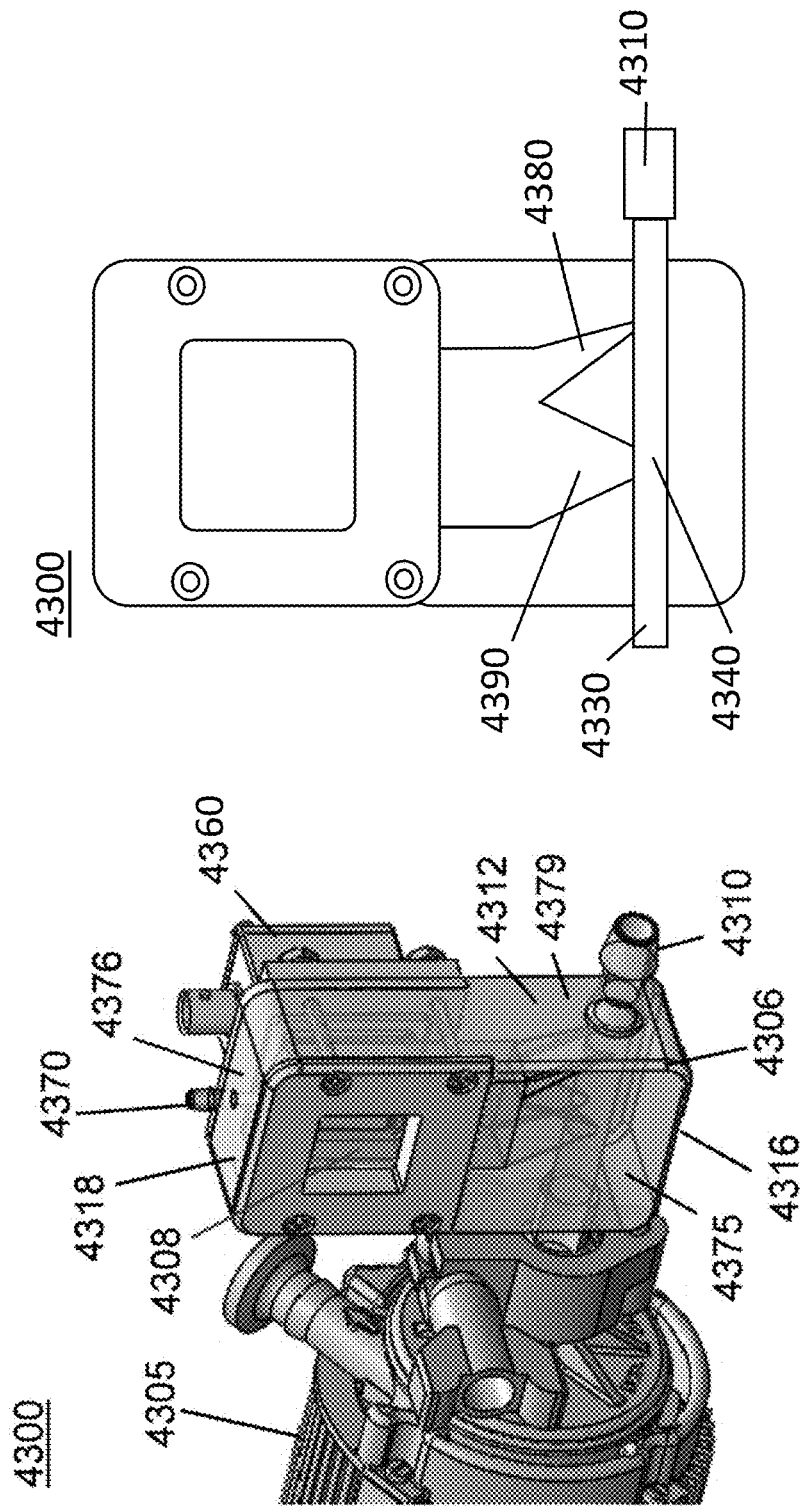

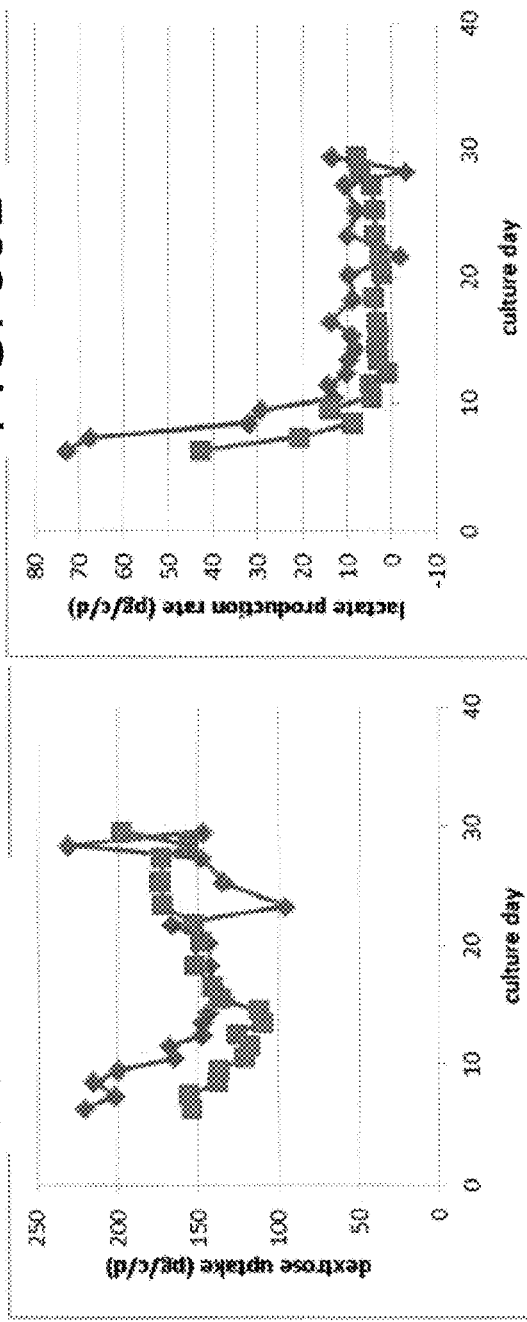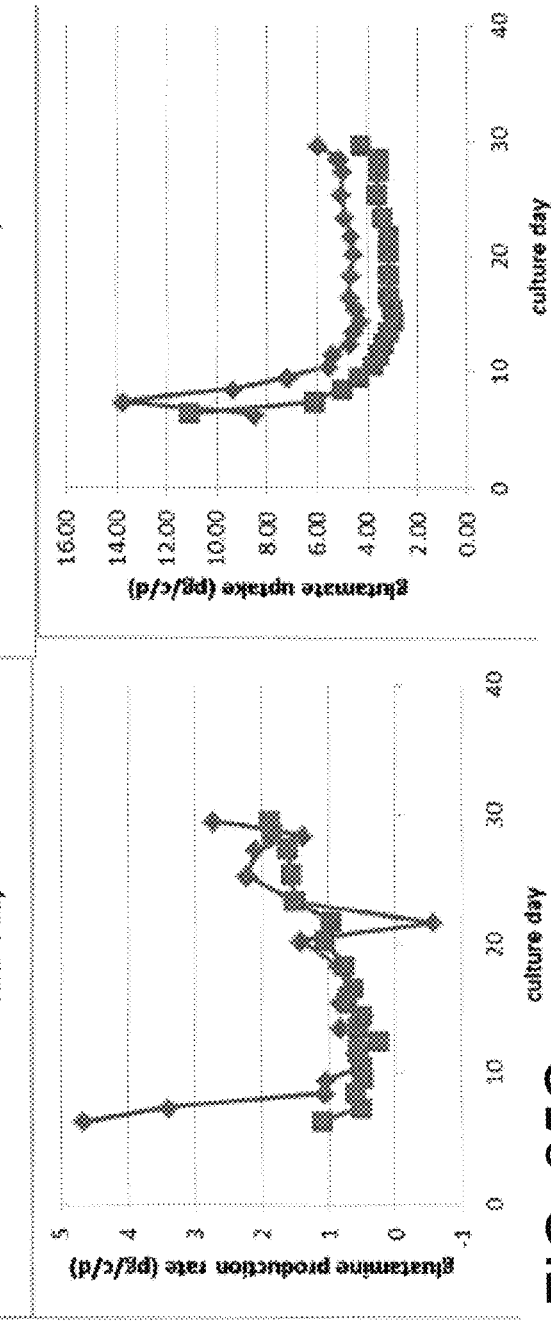

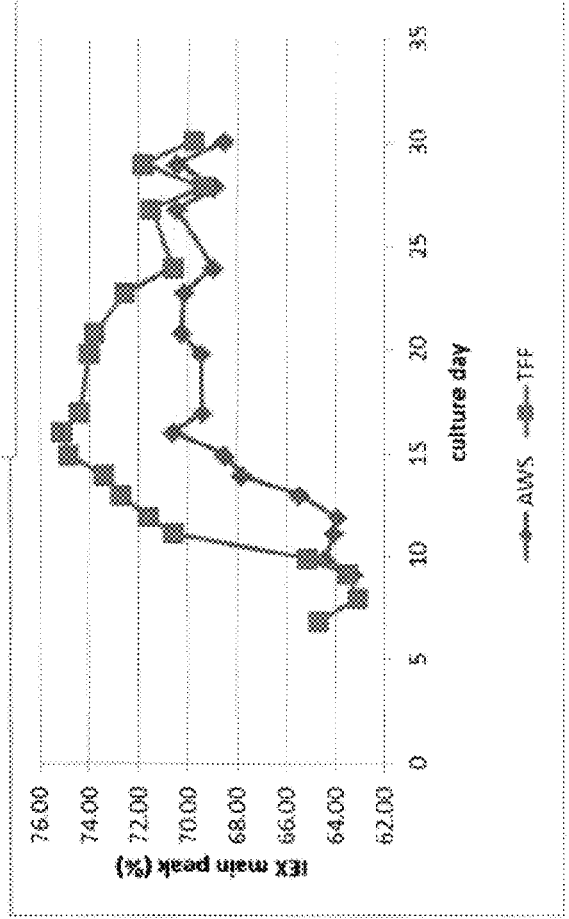
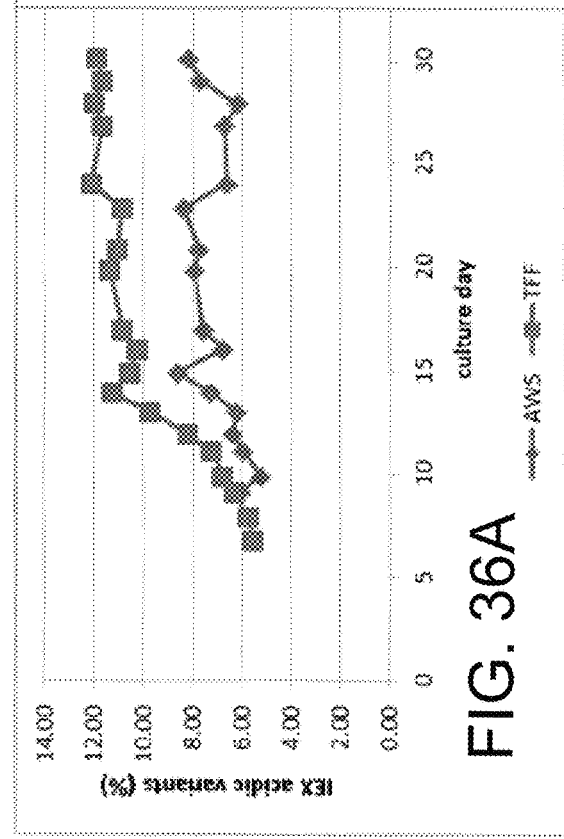
FIG. 36A
FIG. 36B
FIG. 36C

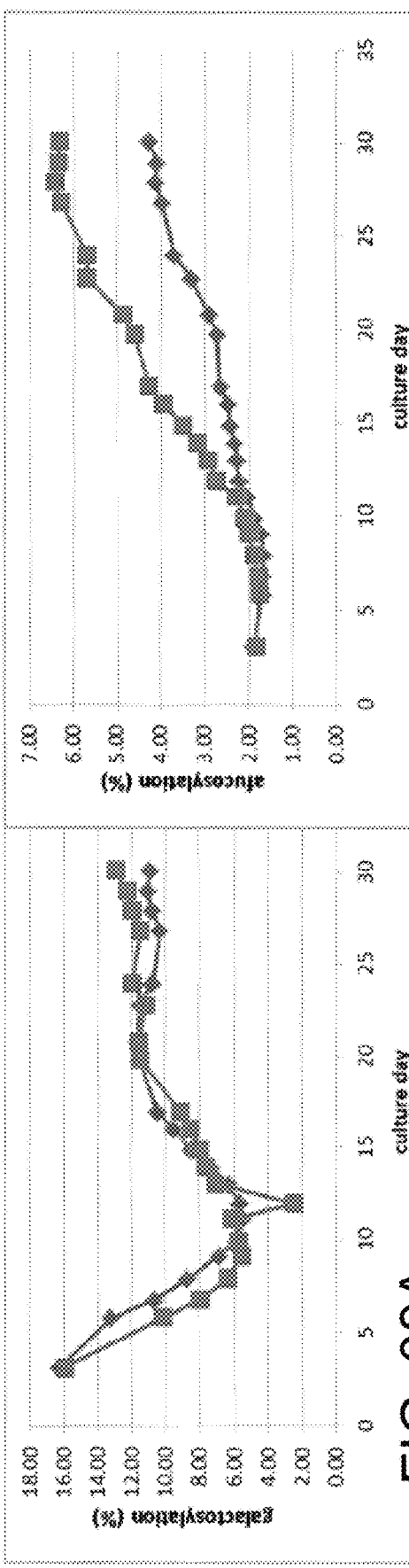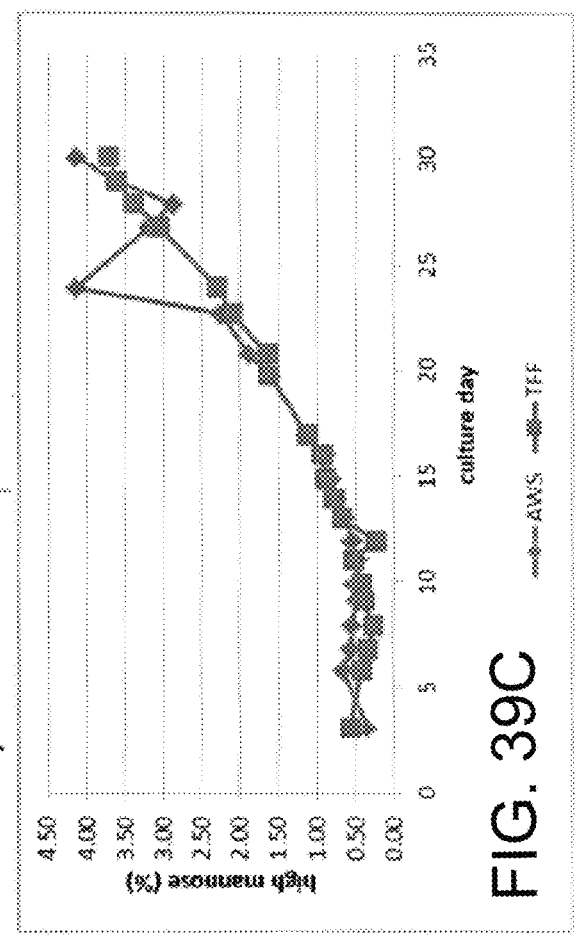
FIG. 39A
FIG. 39B
FIG. 39C

ACOUSTIC PERFUSION DEVICES

CROSS-REFERENCE TO RELATED APPLICATIONS

This application claims priority to U.S. Provisional Patent Application Ser. No. 62/563,068, filed on Sep. 26, 2017, and to U.S. Provisional Patent Application Ser. No. 62/482,681, filed on Apr. 26, 2017. This application is also a continuation-in-part of U.S. patent application Ser. No. 15/696,176, filed Sep. 5, 2017, which is a continuation of U.S. patent application Ser. No. 15/139,187 filed Apr. 26, 2016, now U.S. Pat. No. 9,752,113, which is a continuation-in-part of U.S. patent application Ser. No. 14/975,307, filed Dec. 18, 2015, now U.S. Pat. No. 9,822,333, which claims priority to U.S. Provisional Patent Application Ser. No. 62/256,952, filed on Nov. 18, 2015, and to U.S. Provisional Patent Application Ser. No. 62/243,211, filed on Oct. 19, 2015, and to U.S. Provisional Patent Application Ser. No. 62/211,057, filed on Aug. 28, 2015, and to U.S. Provisional Patent Application Ser. No. 62/093,491, filed on Dec. 18, 2014. U.S. patent application Ser. No. 14/975,307 is also a continuation-in-part of U.S. patent application Ser. No. 14/175,766, filed on Feb. 7, 2014, now U.S. Pat. No. 9,416,344, which claims priority to U.S. Provisional Patent Application Ser. No. 61/761,717, filed on Feb. 3, 2013, and is also a continuation-in-part of U.S. patent application Ser. No. 14/026,413, filed on Sep. 13, 2013, now U.S. Pat. No. 9,458,450, which claims the benefit of U.S. Provisional Patent Application Ser. No. 61/708,641, filed on Oct. 2, 2012. U.S. patent application Ser. No. 14/026,413 is also a continuation-in-part of U.S. Ser. No. 13/844,754, filed Mar. 15, 2013, which claims the benefit of U.S. Provisional Patent Application Ser. No. 61/611,159, filed Mar. 15, 2012, and of U.S. Provisional Patent Application Ser. No. 61/611,240, filed Mar. 15, 2012, and of U.S. Provisional Patent Application Ser. No. 61/708,641, filed Oct. 2, 2012, and of U.S. Provisional Patent Application Ser. No. 61/754,792, filed Jan. 21, 2013. These applications are incorporated herein by reference in their entireties.

BACKGROUND

One of the key components that is utilized in the manufacturing processes of new biologically based pharmaceuticals is the bioreactor and the ancillary processes associated therewith. An area of growth in the bioreactor field has been with the perfusion process. The perfusion process is distinguished from the fed-batch process by its lower capital cost and continuous (rather than batch) operation.

A perfusion bioreactor processes a continuous supply of fresh media that is fed into the bioreactor while growth-inhibiting byproducts are constantly removed. The nonproductive downtime can be reduced or eliminated with a perfusion bioreactor process. The cell densities achieved in perfusion culture (30-100 million cells/mL) are typically higher than for fed-batch modes (5-25 million cells/mL). These improvements have led to lower contamination in the harvest and better yields without significant increase in cost. A perfusion bioreactor may use a cell retention device to prevent escape of the culture when byproducts are being removed. These cell retention systems add a level of complexity to the perfusion process, which may be seen in the additional management, control, and/or maintenance activities that can lead to successful operation. Operational issues such as malfunction or failure of the cell retention equipment has previously been a problem with perfusion bioreactors, which has limited their attractiveness in the past.

BRIEF DESCRIPTION

The present disclosure relates, in various embodiments, to acoustic devices and processes which are used for perfusion biomanufacturing. More particularly, the devices are coupled to an associated bioreactor. Within the bioreactor, biomolecules, such as recombinant proteins or monoclonal antibodies, are produced from cells. The acoustic device is used for separating the biomolecules from the cells on a continuous basis, and the cells are continuously returned to the bioreactor. In some examples, a fluid mixture containing the cells and the desired products (e.g., biomolecules) are passed or flowed through the acoustic device and separated therein by multi-dimensional standing wave(s). The fluid mixture may contain other materials, such as cell debris and fines. The fluid mixture can be continuously flowed into the device, with desired products being continuously removed. The acoustic perfusion device returns healthy viable cells to the bioreactor while desired products are harvested and flowed downstream for further processing, e.g., additional filtering, chromatography, etc. Additionally, the cell culture media in the bioreactor is clarified as cell fragments are also allowed to pass into the harvest stream and thereby out of the fluid mixture being recycled to the bioreactor.

In some examples, smaller, less productive cells are selected out of the bioreactor return stream thus leaving larger more productive cells in the bioreactor. This retention of larger cells in the bioreactor system increases the specific cell productivity due to the size of the cells and the greater amount of ribosomal content for protein production. This increase in productivity results in lower overall cell culture media usage, corresponding to a predicted cost savings of up to $20,000 per day for large bioreactors.

Disclosed in various embodiments are acoustic perfusion devices, comprising: an acoustic chamber and an outlet flow path from the acoustic chamber. At least one ultrasonic transducer is coupled to the acoustic chamber to one side of the outlet flow path. The at least one ultrasonic transducer includes a piezoelectric material that can be excited to generate an acoustic standing wave across a portion of the acoustic chamber. The acoustic standing wave may be planar or multi-dimensional, or a combination of such waves may be present within the acoustic chamber. Multiple transducers may be used to generate the acoustic standing wave(s). The acoustic standing wave can be thought of as a "force field" that holds back whole cells but permits smaller materials such as the desired biomolecules (e.g. recombinant proteins and/or monoclonal antibodies) and cell fragments, to pass through and be removed from the fluid that is returned to the bioreactor.

In some examples, an inlet port, an inlet flow path leading from the inlet port to the acoustic chamber; an outlet port for recirculating fluid flowing through the device back to its source (e.g. a bioreactor) may be provided. The outlet port may be arranged below the inlet port, and may be located at a bottom end of the device.

As mentioned above, the device may have one or more collection or harvest ports at the top of the device. In some more specific embodiments, the device may have a total of two harvest ports spaced apart from each other on the top end of the device.

In particular embodiments, the inlet port is at a first end of the device at a first height, the at least one ultrasonic transducer is at a second height above the first height, and a bottom wall extends from the inlet port to the outlet port. The outlet port may be located at a second end of the device opposite the first end. The bottom wall may be concave, relative to a line between the inlet port and the outlet port. The device may include an upper wall above the inlet flow path. The inlet port, the outlet port, and the at least one harvest port are sometimes all located on a front wall of the device. The front wall itself may be planar (i.e. flat).

The device can further comprise a reflector located in the acoustic chamber opposite the at least one ultrasonic transducer. Alternatively, the device can have a total of two ultrasonic transducers located on opposite sides of the harvest flow path at the same height and facing each other, or additional ultrasonic transducers can be located on multiple sides of the collection/harvest flow path. A reflector may be located between the two ultrasonic transducers. There may also be a plurality of transducer/reflector pairs located as appropriate to form planar, multi-dimensional, or combinations of such acoustic standing wave(s).

In particular embodiments, the acoustic standing wave results in an acoustic radiation force having an axial force component and a lateral force component that are of the same order of magnitude.

In other embodiments of the device disclosed herein, the inlet flow path leads from the inlet port downwards towards a bottom end of the device and past the outlet port, and then upwards to the acoustic chamber. Sometimes, the inlet port and the at least one harvest port are both located on a top wall of the device, and the outlet port is located on a front wall of the device. The at least one ultrasonic transducer may be mounted in a rear wall or a front wall of the device. The bottom wall of this acoustic chamber can be a sloped planar surface. The reflector may be made of a transparent material.

The inlet flow path may be shaped to generate a tangential flow path below an acoustic field generated by the acoustic standing wave. In still additional versions seen herein, the inlet flow path enters the acoustic chamber on a first side of the device, and the outlet port is located (i) on the first side of the device or (ii) on a second opposite side. The inlet port can be located on a front side of the device, and the at least one harvest port can be located on a top wall of the device. The at least one transducer can be located on a front side or a rear side of the device. In more particular embodiments, there can be two transducers, one on the front side and one of the rear side. In yet other particular embodiments, there is an ultrasonic transducer on the front or rear side, and a reflector located on the respective rear or front side opposite the transducer.

In additional embodiments, the perfusion device further comprises a recirculation flow path between the inlet port and the outlet port that does not enter the acoustic chamber, and the recirculation flow path is located below the acoustic chamber. In some particular embodiments, the inlet flow path travels through a different passage than the outlet flow path. In yet other embodiments, the inlet flow path and the outlet flow path travel through a common passage.

The device may be attached to a mounting piece having holes for attachment.

Also disclosed are methods for separating cells from a fluid mixture containing the cells. The fluid mixture is flowed through an acoustic perfusion device of the structure described above, having at least one ultrasonic transducer. The at least one ultrasonic transducer is driven to create the acoustic standing wave. A fluid enriched in cells can be collected from the outlet port and a clarified fluid, depleted in cells, can be collected from the at least one harvest port.

In particular embodiments, the flow rate through the collection/harvest flow path is at least one order of magnitude smaller than a flow rate through the inlet flow path. In specific embodiments, a flow rate of the fluid mixture entering the device through the inlet port is about 1 liter per minute and a flow rate of the fluid depleted in cells exiting the device through the at least one collection/harvest port is about 10 milliliters per minute. Alternatively, the ratio of the flow rate entering through the inlet port to the flow rate exiting through the at least one collection/harvest port is such that the acoustic standing wave is not overcome by the main body of cells, or in other words so that a large volume of cells do not begin exiting the device through the collection/harvest port(s).

The methods may further comprise pulling the fluid mixture through the device using a first pump attached to the at least one harvest port of the device and a second pump attached to the outlet port of the device.

Also disclosed herein are flow devices adapted to (i) receive a flowing mixture containing a primary fluid and cells; and (ii) to use a first acoustic standing wave to continuously draw off a harvest fluid stream depleted in cells from the flowing mixture, thereby changing the cell concentration of the flowing mixture. A pressure rise may be generated on the upstream interface region of the acoustic standing wave, along with an acoustic radiation force acting on the incoming suspended particles. This "interface effect", which may also be termed "edge effect", can act as a barrier. In some examples the interface effect is located at the upstream bounding surface of the volume of fluid that is ensonified by the transducer. For example, the flow mixture crosses the interface region to enter the ensonified volume of fluid. The frequency of the acoustic standing wave may be modified such that different contrast factor materials may be held back by or allowed through the acoustic standing wave, or such that particles of one given size range are retained and particles of a second given range are allowed to flow through the standing wave. The acoustic standing waves that form the "edge effect" may also be modulated so as to let selective materials through at different times in the process.

The device may further comprise a secondary flow chamber in which the harvest fluid stream depleted in cells passes through a second acoustic standing wave having a frequency different from, or equal to the first acoustic standing wave. For example, the second acoustic standing wave may have a higher or lower frequency than the first acoustic standing wave. The ratio of the frequency of the two standing waves is, in some embodiments, at least 2:1 (i.e. one of the frequencies is at least twice the other frequency, e.g. 3 MHz and 6 MHz).

Also disclosed herein are flow devices that comprise: at least one inlet for receiving a flowing mixture of a primary fluid and cells, an ultrasonic transducer that produces a first ultrasonic acoustic standing wave and uses a pressure rise and an acoustic radiation force generated on an upstream interface region of the first ultrasonic acoustic standing wave to separate the flowing mixture into a primary high cell concentration fluid stream and a secondary harvest fluid stream; an outlet port for the primary high cell concentration fluid stream; and at least one collection port for the secondary harvest fluid stream. A bleed port can also be present for extracting a concentrated fluid/cell mixture. The fluid mixture may comprise particles such as mammalian cells, bacteria, cell debris, fines, proteins, exosomes, vesicles, viruses, and insect cells.

The device may further comprise a secondary flow chamber in which the secondary harvest fluid stream passes through a second acoustic standing wave having a frequency different from, or equal to, the first ultrasonic acoustic standing wave.

Disclosed in various embodiments herein are processes for separating biomolecules (e.g., therapeutic antibodies) from a fluid mixture. The process comprises flowing a fluid mixture containing biomolecules and cells through an acoustic perfusion device. The acoustic perfusion device includes an acoustic chamber through which the fluid mixture containing the biomolecules and cells flows, and an ultrasonic transducer and a reflector opposite the ultrasonic transducer, the ultrasonic transducer including a piezoelectric material driven to create a multi-dimensional acoustic standing wave in the acoustic chamber. The ultrasonic transducer is driven to create the multi-dimensional acoustic standing wave. In particular, the reflector is set up opposite the ultrasonic transducer, and the ultrasonic transducer is electronically driven to form a multi-dimensional acoustic standing wave in the flow chamber. Alternatively, two opposing ultrasonic transducers may be used to generate the multi-dimensional acoustic standing wave. An ultrasonic transducer may be used to generate an acoustic wave, as well as to reflect an acoustic wave, which can contribute to generating the multi-dimensional acoustic standing wave. Aggregates of the biomolecules, form higher molecular weight species of the monoclonal antibodies or recombinant proteins. The acoustic standing wave may be modified to hold back these aggregated proteins and not separate them from the monomer or pure monoclonal antibody that is the product of the bioreactor process. Aggregated proteins are typically less effective or ineffective at the therapeutic aspects of the monoclonal antibody that is designed to be produced and expressed by the Cho cells.

The separated biomolecules can be subjected to further processing downstream of the acoustic perfusion device. The further processing can include at least one of chromatography and additional filtration (e.g., depth filtration, crossflow filtration, tangential filtration, sterile filtration).

In particular embodiments, the biomolecules are proteins, such as therapeutic antibodies. The mechanism of action of the therapeutic antibodies can include antibody-dependent, cell-mediated cytotoxicity (ADCC). The fucosylation of the therapeutic antibodies can be decreased and the efficacy of the therapeutic antibodies can be increased. The therapeutic antibodies can be non-fucosylated.

The biomolecules can, in certain embodiments, be produced by culturing cells in a bioreactor (e.g., a perfusion bioreactor) prior to flowing the fluid mixture through the acoustic perfusion device. In particular embodiments, a pressure rise and an acoustic radiation force on cells are generated at an interface region of the multi-dimensional acoustic standing wave to clarify the fluid mixture as it passes through the multi-dimensional acoustic standing wave. The acoustic perfusion device can further comprise a recirculating fluid stream that transports away cells that are constantly held back at the interface region of the multi-dimensional acoustic standing wave. The multi-dimensional acoustic standing wave may result in an acoustic radiation force having an axial force component and a lateral force component that are of the same order of magnitude.

The process of the present disclosure are useful for producing desired biomolecules (e.g., monoclonal antibodies, recombinant proteins). In particular embodiments, the biomolecules can be glycoengineered to produce antibodies with predetermined glycoforms.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 19A is at a frequency of 2.218 MHz. FIG. 19B is at a frequency of 2.2465 MHz. FIG. 19C is at a frequency of 2.3055 MHz. For all three graphs, the left-side scale is indicated with text at the top of the scale reading "×10$^{-6}$" or "×10$^{-7}$", and is in units of inches. The right-side scale is indicated with text at the top of the scale reading "×10$^6$", and is in units of Pascals. The y-axis runs from −0.8 to 1.6 in intervals of 0.2. The x-axis runs from −0.5 to 1.5 in intervals of 0.5.

FIG. 25 is a perspective view of an example implementation of an acoustic perfusion device of the present disclosure. This embodiment includes a direct recirculation flow path between the inlet port and the outlet port. An inflow passageway and an outflow passageway join the recirculation flow path to the acoustic chamber, and create a tangential sweeping flow underneath the acoustic field.

FIG. 26 is a front view picture of the device of FIG. 25. The inflow passageway and the outflow passageway are clearly visible, along with the recirculation pipe.

FIGS. 35A-35D illustrate four graphs of metabolism using nutrient uptake markers for both a TFF process and an AWS process according to the present disclosure versus time. The x-axis of all four graphs represents time (in culture days) and runs from 0 to 40 days in intervals of 10. The y-axis of FIG. 35A represents dextrose uptake (expressed in pg/cell/day) and runs from 0 to 250 in intervals of 50. The y-axis of FIG. 35B represents lactate production rate (expressed in pg/cell/day) and runs from −10 to 80 in intervals of 10. The y-axis of FIG. 35C represents glutamine production rate (expressed in pg/cell/day) and runs from −1 to 5 in intervals of 1. The y-axis of FIG. 35D represents glutamate uptake (expressed in pg/cell/day) and runs from 0 to 16 in intervals of 2.

FIGS. 36A-36C illustrate three graphs of ion exchange chromatography (IEX) results of charge variants for both a TFF process and an AWS process according to the present disclosure versus time. The x-axis of all three graphs represents time (in culture days) and runs from 0 to 35 days in intervals of 5. The y-axis of FIG. 36A represents IEX acidic variants (percentage) and runs from 0 to 14 in intervals of 2. The y-axis of FIG. 36B represents IEX basic variants (percentage) and runs from 0 to 35 in intervals of 5. The y-axis of FIG. 36C represents IEX main peak (percentage) and runs from 62 to 76 in intervals of 2.

FIGS. 39A-39C illustrate three additional graphs of glycosylation (N-glycan) results for both a TFF process and an AWS process according to the present disclosure versus time. The x-axis of all three graphs represents time (in culture days) and runs from 0 to 35 days in intervals of 5. The y-axis of FIG. 39A represents galactosylation (percentage) and runs from 0 to 18 in intervals of 2. The y-axis of FIG. 39B represents afucosylation (percentage) and runs from 0 to 7 in intervals of 1. The y-axis of FIG. 39C represents high mannose (percentage) and runs from 0 to 4.5 in intervals of 0.5.

DETAILED DESCRIPTION

Figure 1:
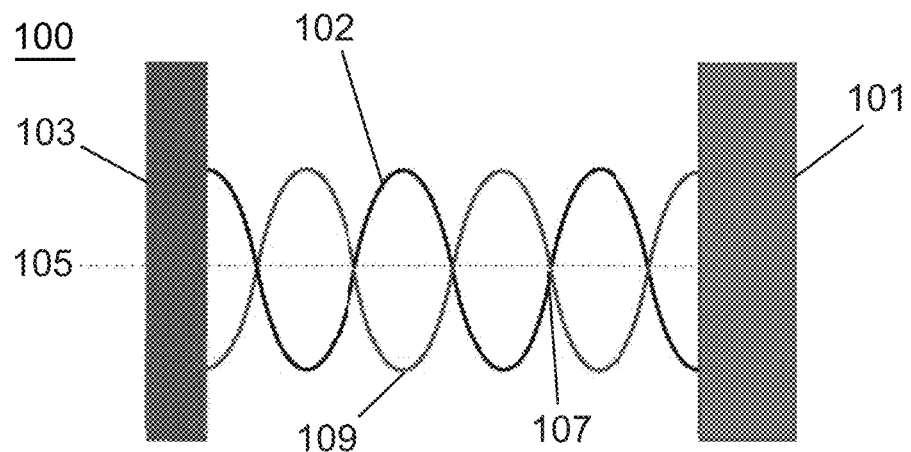
FIG. 1 illustrates a single standing acoustic wave generated by an ultrasonic transducer and a reflector.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The present application refers to "the same order of magnitude." Two numbers are of the same order of magnitude if the quotient of the larger number divided by the smaller number is a value of at least 1 and less than 10.

The acoustic devices discussed herein may operate in a multimode or planar mode. Multimode refers to generation of acoustic waves by an acoustic transducer that create acoustic forces in three dimensions. The multimode acoustic waves, which may be ultrasonic, are generated by one or more acoustic transducers, and are sometimes referred to herein as multi-dimensional or three-dimensional acoustic standing waves. Planar mode refers to generation of acoustic waves by an acoustic transducer that create acoustic forces substantially in one dimension, e.g. along the direction of propagation. Such acoustic waves, which may be ultrasonic, that are generated in planar mode are sometimes referred to herein as one-dimensional acoustic standing waves.

The acoustic transducers may be composed of piezoelectric material. Such acoustic transducers can be electrically excited to generate planar or multimode acoustic waves. The three-dimensional acoustic forces generated by multimode acoustic waves include radial or lateral forces that are unaligned with a direction of acoustic wave propagation. The lateral forces may act in two dimensions. The lateral forces are in addition to the axial forces in multimode acoustic waves, which are substantially aligned with the direction of acoustic wave propagation. The lateral forces can be of the same order of magnitude as the axial forces for such multimode acoustic waves. The acoustic transducer excited in multimode operation may exhibit a standing wave on its surface, thereby generating a multimode acoustic wave. The standing wave on the surface of the transducer may be related to the mode of operation of the multimode acoustic wave. When an acoustic transducer is electrically excited to generate planar acoustic waves, the surface of the transducer may exhibit a piston-like action, thereby generating a one-dimensional acoustic standing wave. Compared to planar acoustic waves, multimode acoustic waves exhibit significantly greater particle trapping activity on a continuous basis with the same input power. One or more acoustic transducers may be used to generate combinations of planar and multi-dimensional acoustic standing waves. In some modes of operations, multimode acoustic waves generate an interface effect that can hold back or retain particles of a certain size, while smaller particles can flow through the multimode acoustic waves. In some modes of operation, planar waves can be used to deflect particles at certain angles that are characteristic of the particle size.

Bioreactors are useful for making biomolecules such as recombinant proteins or monoclonal antibodies. Very generally, cells are cultured in a bioreactor vessel with media in order to produce the desired product, and the desired product is then harvested by separation from the cells and media in an acoustic perfusion device, such as the device of the present disclosure. The acoustic filtering device permits the withdrawal of some desired product, a small portion of the media, and cellular fragments/debris smaller than the cells, with the remainder being recycled back to the bioreactor (particularly the cells). The use of mammalian cell cultures including Chinese hamster ovary (CHO), NS0 hybridoma cells, baby hamster kidney (BHK) cells, insect cells, and human cells (e.g. T-cells, B-cells, stem cells, red blood cells), and living/biological cells in general has proven to be a very efficacious way of producing/expressing the recombinant proteins and monoclonal antibodies used in various applications such as pharmaceuticals or vaccines. Two general types of bioreactor processes exist: fed-batch and perfusion.

A perfusion bioreactor may be utilized to generate cells that would be utilized in a cell therapy process. In this type of perfusion bioreactor, biological cells such as CAR T-cells, Jurkat T-cells and the like are cultured in a perfusion bioreactor. The acoustic standing wave used in the perfusion devices of the present disclosure can be used to separate viable and nonviable cells after the transfection process. This allows for improved efficacy of the inoculation of the patient with this T-cell therapy as only viable cells are utilized. The nonviable cells and cell fragments are separated out through the perfusion process, with these materials going into the secondary flow and exiting the bioreactor.

A perfusion bioreactor may also be used for production of exosomes, microvesicles, or vesicles by cells. The acoustic perfusion device can then be used to harvest the exosomes, or other desired cell products. In a similar fashion, a perfusion bioreactor can be used to produce viruses, such as lentivirus, which are used in cell and gene therapy to transfect cells. The acoustic perfusion device can then be used to harvest the virus. In all cases, the device is a cell retention device.

Recent developments in perfusion bioreactor technology also favor its use. Control technology and general support equipment is improving for perfusion bioreactors, increasing the robustness of perfusion processes. The perfusion process can now be scaled up to bioreactors having a volume up to 1000 liters (L). Better cell retention systems for perfusion bioreactors result in lower cell loss and greater cell densities than have been seen previously. Cell densities greater than 50 million cells/mL are now achievable, compared to fed-batch cell densities of around 20 million cells/mL. Lower contamination and infection rates have improved the output of perfusion bioreactors. Higher product concentrations in the harvest and better yields without significant increase in cost have thus resulted for perfusion processes.

Perfusion bioreactors are particularly attractive because of the continuous production of the biomolecules from the expressing cell culture, and shorter residence time of said biomolecules in the process prior to harvest. The target cells are held back by a filtration process, such as tangential flow filtration (TFF) or alternating tangential flow filtration (ATF) while the expressed biomolecules are extracted from the perfusion bioreactor. The cells are then returned to the bioreactor to ensure they receive the nutrition and oxygen to maintain the production of the overall cell culture. In the perfusion reactor process, the cells continue to multiply. Some of the cell culture population may be bled off via a portion or all of the perfusion production process.

The TFF and ATF processes of filtration have several issues, such as clogging/fouling and loss of biomolecule product (particularly at high cell densities), all directly related to the nature of the hollow fiber membranes used in the filtration. It is therefore desirable to find a new filtration process that does not clog and minimizes loss of the desired biomolecule product. In addition, TFF and ATF will retain all cellular debris and fines within the bioreactor, which is not desirable. A process capable of distinguishing between cell retention while allowing for the passing of cell debris and fines may therefore be favorable. Further yet, undesirable protein aggregation during monoclonal antibody production is known to occur in upstream and downstream processing, which is a major concern for therapeutic applications where aggregates influence drug performance and safety. Thus, processes that remove protein aggregates are desirable. Such processes are especially desirable for multiple reasons including that protein aggregates are typically non-functional and are a problem for the efficacy of therapeutic drugs, which makes their removal even more desirable.

Briefly, the present disclosure relates to acoustic perfusion devices capable of generating multi-dimensional acoustic standing wave(s) from one or more piezoelectric transducers, where the transducers are electrically excited such that they move in a multimode displacement pattern rather than a "piston" mode of vibration. Through this manner of acoustic standing wave generation, a higher lateral trapping force is generated than if the piezoelectric transducer is excited in a "piston" mode where only one large standing wave is generated. Thus, with the same input power to a piezoelectric transducer, the multi-dimensional acoustic standing waves can have a higher lateral trapping force compared to a planar acoustic standing wave. The input power is tunable for a controlled flow. This can be used to facilitate proteinaceous fluid purification of a fluid stream coming from a bioreactor. Alternatively, the acoustic standing wave may also be a planar standing wave where the piezoelectric transducer is excited in the piston mode, generating a planar wave. The acoustic standing wave(s) may also be a combination of planar and multi-dimensional acoustic standing waves. All of these standing waves generate an "interface effect" such that the cells from the bioreactor are held back and the biomolecule product expressed from the cells, cell fragments and small debris are allowed to pass through.

Acoustophoresis is a low-power, no-pressure-drop, no-clog, solid-state approach to particle separation from fluid dispersions (i.e., it is used to achieve separations that are more typically performed with porous filters, but it has none of the disadvantages of filters). In particular, the acoustic perfusion devices of the present disclosure are suitable for use with macro-scale bioreactors for separations in flowing systems with high flow rates. The acoustic perfusion device is designed to create a high intensity multi-dimensional ultrasonic standing wave that results in an acoustic radiation force that can overcome the combined effects of fluid drag and buoyancy or gravity at certain flow rates. As a result, the radiation force acts as a filter that prevents targeted particles (e.g., biological cells) from crossing through the standing wave. As explained above, the trapping capability of a standing wave may be varied as desired, for example by varying the flow rate of the fluid, the acoustic radiation force, and the shape of the acoustic filtering device to maximize cell retention through trapping and settling. This technology offers a green and sustainable alternative for separation of secondary phases with a significant reduction in cost of energy. Excellent particle separation efficiencies have been demonstrated for particle sizes as small as one micron.

Generally, the scattering of the acoustic field off the particles results in a three-dimensional acoustic radiation force, which acts as a three-dimensional trapping field. The acoustic radiation force is proportional to the particle volume (e.g., the cube of the radius) when the particle is small relative to the wavelength. It is proportional to frequency and the acoustic contrast factor. It also scales with acoustic energy (e.g., the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the lateral and axial acoustic forces on the trapped particles results in formation of tightly packed clusters through concentration, clustering, clumping, agglomeration and/or coalescence of particles that, when reaching a critical size, settle continuously through enhanced gravity for particles heavier than the host fluid or rise out through enhanced buoyancy for particles lighter than the host fluid. Additionally, secondary inter-particle forces, such as Bjerkness forces, aid in particle agglomeration.

Most biological cell types present a higher density and lower compressibility than the medium in which they are suspended, so that the acoustic contrast factor between the cells and the medium has a positive value. As a result, the axial acoustic radiation force (ARF) drives the cells towards the standing wave pressure nodes. The axial component of the acoustic radiation force drives the cells, with a positive contrast factor, to the pressure nodes, whereas cells or other particles with a negative contrast factor are driven to the pressure anti-nodes. The radial or lateral component of the acoustic radiation force is the force that traps the cells. The radial or lateral component of the ARF is larger than the combined effect of fluid drag force and gravitational force. Desirably, the ultrasonic transducer(s) generates a multi-dimensional standing wave in the fluid that exerts a lateral force on the suspended particles to accompany the axial force. Typical results published in literature state that the lateral force is two orders of magnitude smaller than the axial force. In contrast, the technology disclosed in this application provides for a lateral force to be of the same order of magnitude as the axial force. However, in certain embodiments described further herein, the device use both transducers that produce multi-dimensional acoustic standing waves and transducers that produce planar acoustic standing waves. For purposes of this disclosure, a standing wave where the lateral force is not the same order of magnitude as the axial force is considered a "planar acoustic standing wave." The lateral force component of the total acoustic radiation force (ARF) generated by the ultrasonic transducer(s) of the present disclosure is significant and is sufficient to overcome the fluid drag force at linear velocities of up to 1 cm/s, and to create tightly packed clusters, and is of the same order of magnitude as the axial force component of the total acoustic radiation force.

Figure 24:
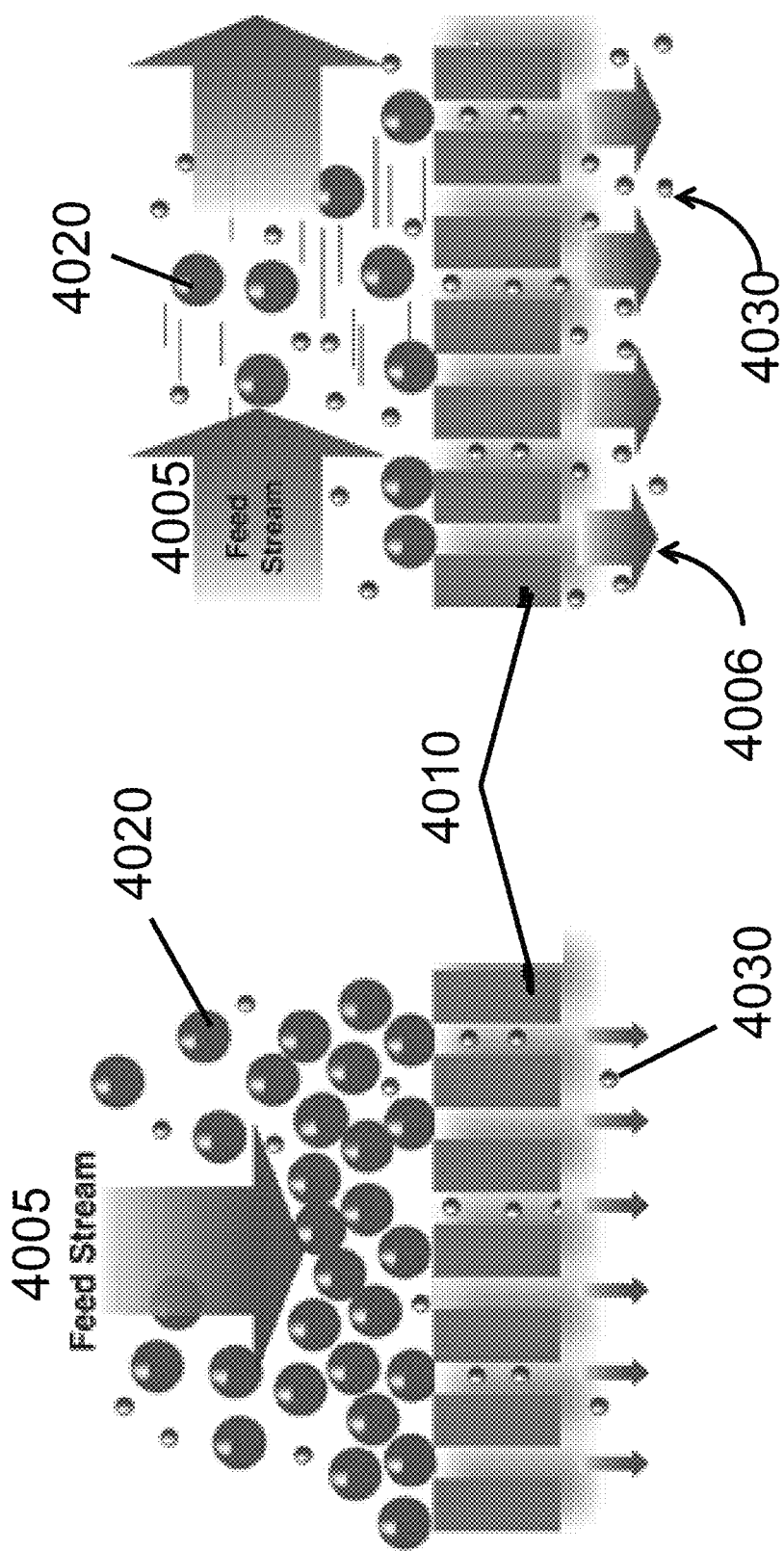
FIG. 24 is a prior art illustration showing depth flow filtration (DFF) and tangential flow filtration (TFF).

It may be helpful to contrast the technology of the present disclosure with that of prior filtration technology. FIG. 24 shows two prior art filtration methods. The left-hand side of FIG. 24 illustrates depth flow filtration (DFF). In DFF, the entire feed stream 4005 of fluid and particles is directed towards the filter. The filter 4010 holds back the particles 4020 that are larger than the filter's pore size, whereas smaller particles 4030 and the fluid pass through the filter. The right-hand side of FIG. 24 illustrates tangential flow filtration (TFF). In TFF, the feed stream is not directed towards the filter. Rather, the feed stream is directed tangentially to the filter, such that a majority of the feed stream passes tangentially over the filter surface. Typically, this feed stream is recirculated to pass by the filter more than once. A much smaller filtrate stream 4006 is pulled through the filter membrane containing the smaller particles 4030. One advantage of TFF over DFF is that the tangential stream reduces the clogging and fouling of the filter and the formation of a gel layer that sits on top of the filter.

In the devices of the present disclosure, during startup, the fluid ensonified by the acoustic standing wave is clarified by the process of trapping cells and growing them into tightly packed clusters, such that continuous gravitational separation of the clusters of cells takes place. Since there is a limited amount of new cells flowing into this volume, this results in a rapid clarification of the fluid subjected to the acoustic standing wave. When this state is reached, the system can be described as including two fluids: a first fluid containing the desired product and small cell fragments/debris (which have passed through the acoustic standing wave), and a second fluid containing the bioreactor fluid and all of the cells (which are held back by the acoustic standing wave). The two fluids may be of different effective acoustic properties, such as density and speed of sound, with a well-defined interface between these two fluids. The acoustic standing wave is a three-dimensional acoustic field, which, in the case of excitation by a rectangular transducer, can be described as occupying a roughly rectangular prism volume of fluid. Typically, two opposing faces are the transducer and reflector, an adjacent pair of opposing faces are the walls of the device, and the final opposing pair of faces, the upstream and downstream faces of the cube, extend through the fluid. The interface between the two fluids is generally located near the upstream face of the acoustic standing wave field, generating an "acoustic barrier or edge effect". This location is also referred to as an upstream interface region. The first fluid (i.e., the fluid that has been clarified and contains the product, some cells, and cell fragments) is downstream of the interface and represents the harvest flow and occupies the volume of fluid ensonified by the acoustic standing wave field. The second fluid (i.e., the fluid containing the bioreactor fluid and most of the cells) is upstream of the interface. During operation at increased flow rates, the interface effect location may move downstream and is then located within the volume of fluid ensonified by the transducer.

The acoustic standing wave field exerts an acoustic radiation pressure (i.e. a pressure rise) and an acoustic radiation force on the cells at the interface region between the two fluids, thereby keeping the upstream cells from entering the acoustic field. The occurrence of the radiation pressure and the force on the interface allows for the first fluid containing the product to pass through the interface while retaining the cells in the upstream fluid. The cells that are held back by the effect of the acoustic radiation force at the interface between the two fluids can be continuously returned to the bioreactor to ensure they receive the nutrition and oxygen to maintain the production of the overall cell culture.

The circulating motion of the flow field underneath the interface transports the cells that are retained by the acoustic field back to the bioreactor. The circulating flow motion is driven by the primary recirculation stream and can be optimized with acoustic chamber geometry variations for maximum system efficiency.

During perfusion, the acoustic perfusion devices of the present disclosure have multiple possible modes of operation. One of these modes may be dominant in the device or they may occur concurrently depending on the distribution of cells and fluid within the device. In a first mode of operation (Mode 1), the fluid containing cells enters the acoustic standing wave field, which is produced between the transducer and the reflector. A multi-dimensional acoustic standing wave traps the cells at specific points, packs the cells into tightly packed clusters, and continuously separates the clusters through enhanced gravitational settling. The cell clusters settle out, enter the tangential flow path and are redirected to the bioreactor by the recirculation stream. Smaller particles 4030 are not trapped by, and pass through, the acoustic standing wave, to be harvested. The orientation of this device is significant due to the use of gravitational settling.

In the second mode of operation (Mode 2), the acoustophoretic system creates a strong barrier for cells at the interface between the two fluids and prevents cells from entering the acoustic field. Here, a barrier of cells is established between the two fluids through the interface effect of the acoustic standing wave. A first clarified fluid stream contains the smaller particles/desired byproducts within the acoustic standing wave field and the harvest stream. A second fluid stream contains the retained cells upstream of the acoustic standing wave field. In this mode of operation, an acoustic interface effect is realized in the interface region between the two fluids, clarified fluid downstream and flow mixture and cells on the upstream side. Very generally, the acoustic interface effect holds the cells back and prevents them from entering the acoustic field while a portion of the fluid stream containing the produced biomolecules and cell fragments is permitted to pass through this barrier. The tangential flow path underneath the acoustic interface (arrow) collects the retained cells and flows them back into the main recirculation stream and back to the bioreactor.

Figure 17:
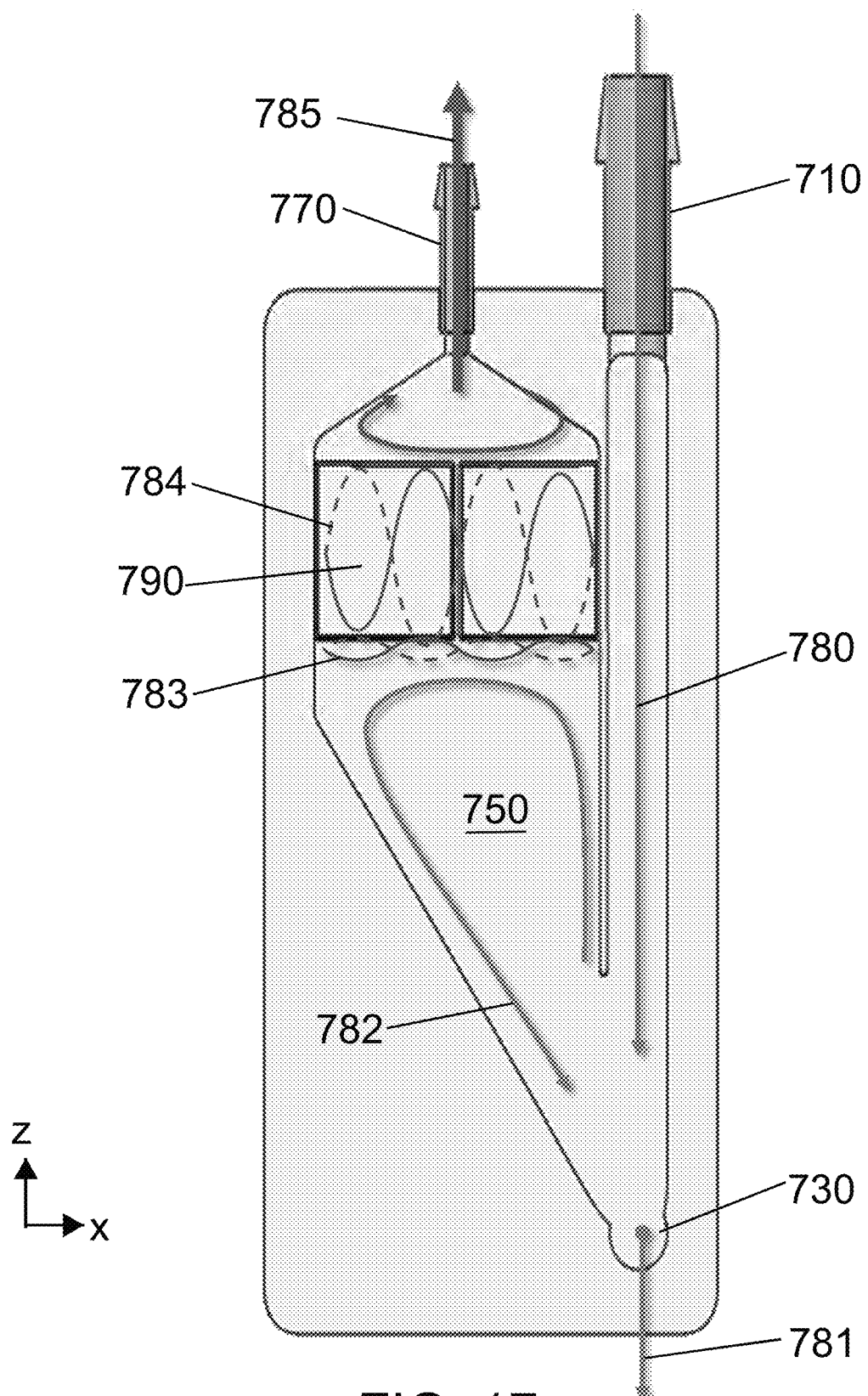
FIG. 17 is a front view of the device of FIG. 7, showing the flow paths, acoustic field, and acoustic interface effect.

In perfusion applications, the setup of the acoustophoretic device is similar to that of TFF. A feed stream containing the cells, cell debris, fines, and product, i.e., protein, flows from the bioreactor into the perfusion system. A portion of the stream flows in a tangential fashion along the upstream/lower interface region of the acoustic standing wave and is recirculated back to the bioreactor. A smaller portion of the feed stream is harvested, i.e., diverted and flows through the acoustic standing wave. Here the acoustic standing wave functions very similarly to the filter in TFF, preventing the cells from entering the acoustic field. The harvest stream contains smaller particles such as cell debris and fines as well as the desired biomolecule product. The cells that are retained by the acoustic standing wave are transported by the recirculation stream back to the bioreactor. FIG. 17, discussed further herein, also illustrates a perfusion device that uses a tangential flow stream.

Perfusion applications typically entail high cell densities, e.g., >50 million cells/m L, and lower harvest velocities contrary to cell clarification or oil/water applications. The two fluid streams also have different effective acoustic properties, i.e., speed of sound and density of the media/cell mixture. As cell density increases, the difference in acoustic properties of the two fluid streams will be more pronounced as well. The acoustic standing wave field will now exert an acoustic radiation pressure, i.e., a pressure rise, on the second fluid stream, enriched with cells, as well as acoustic radiation forces on the cells suspended in the fluid. This radiation pressure and radiation force act at the interface between the two fluids which coincides with the upstream bounding surface of the acoustic field. When this "acoustic interface" effect of acoustic radiation force is sufficiently strong, it will prevent the cells from entering the acoustic field. Equally important is a tangential flow path to collect the retained cells and transport them back to the bioreactor.

Figure 20:
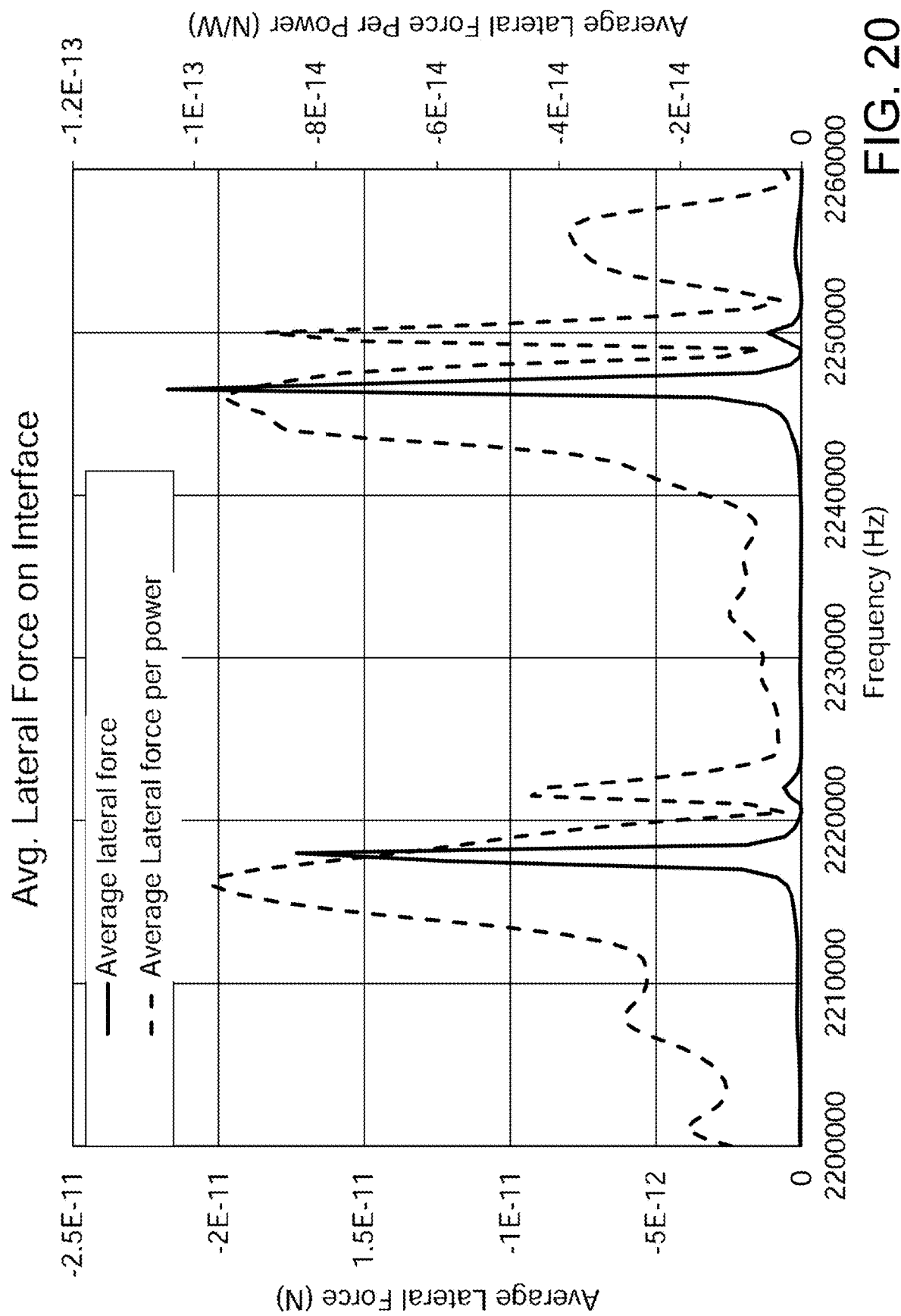
FIG. 20 is a graph showing the average lateral force (N) and the average lateral force normalized by power (N/W) acting on suspended CHO cells at several frequencies of operation.

The acoustic interface effect may also be referred to as an acoustic wall effect and results from the interface of the acoustic field exerting a strong lateral force (i.e., in the opposite direction to the harvest flow and perpendicular to the axis of the acoustic standing wave) on the suspended particles, thereby keeping the relatively larger sized particles from entering the acoustic field and allowing only clarified fluid (i.e., the fluid containing the smaller-sized product) to enter the acoustic field, thereby creating an acoustic perfusion cell retention device. In this way, only the clarified fluid can escape and the cells are held down by the radiation force. This force is never positive, meaning that it always holds the cells down at the interface, i.e., the force is acting in the upstream flow direction, not allowing the cells to pass through the acoustic interface. The multiple peaks in the power curve (see discussion of FIG. 20 below) show the existence of multiple modes of operation including planar resonance modes and multi-dimensional modes of operation, indicating that this type of operation can be generated through utilization of planar and multi-dimensional standing waves alike. In systems having 1"×1" dimensions, there exists a planar resonance about every 30 kHz. FIG. 20 shows evidence of additional peaks indicating the existence of the multi-dimensional modes. Per unit power, these modes can be equally or even more effective as the planar resonance modes. As explained above, the cells that are held back by the acoustic radiation force may then picked up by the scrubbing motion of the fluid flow field (i.e., the recirculating flow underneath the interface), and be continuously returned to the bioreactor to ensure they receive the nutrition and oxygen to maintain the production of the overall cell culture.

The clarified fluid contains both the desired products and cell fragments, all of which are smaller than whole viable cells. In this way, the media that is returned to the bioreactor is clarified of cell fragments. Cell fragments absorb media without producing desired product, making the perfusion process less efficient. Thus, there is an efficiency gain and a cost savings obtained by removing these cell fragments using the acoustic perfusion devices of the present disclosure. Further clarification of the clarified fluid may be achieved downstream using a second device or a secondary flow chamber that contains another transducer-reflector pair that operates at a different frequency. This traps, clumps, clusters, or agglomerates particles having a size of about 10 microns or less that may have passed through the original acoustic standing wave, in the same manner as described before. A third transducer-reflector pair operating at another frequency, 3 MHz to 20 MHz, or higher, may be utilized to trap, clump, cluster, or agglomerate and drop out the small cell fragments and debris that passed through the initial acoustic standing wave and the "interface effect". This triple-clarified fluid containing the desired biomolecules can then directly enter a sterile filter. For example, the original acoustic perfusion device may operate at frequencies up to about 4 MHz. The frequency of this second and third acoustic standing wave field may be from about 6 MHz to about 20 MHz, and possibly higher, to trap smaller sized cell fragments.

During startup of a bioreactor at low cell density, e.g., 2 million cells/mL, the first described mode of operation dominates (Mode 1). As cell density in the bioreactor increases over time, the mode of operation gradually switches from mode 1 to mode 2, and both modes may coexist at the same time.

When an acoustic standing wave is employed for perfusion in a bioreactor with an already high cell density, e.g., 50 million cells/mL, the device typically starts in the first mode of operation, until the volume of fluid within the acoustic standing wave is clarified, at which point the operation gradually switches to the second described mode of operation. At times, during operation, an instability, usually manifested as a perturbation or oscillation of the interface between the two fluids, may grow sufficiently strong such that cells enter the volume of fluid within the acoustic standing wave, at which point, for a short period of time, the device acts in a combined mode of operation, where both modes are active (i.e., the interface effect prevents cells from entering the acoustic field as explained above, while the acoustic field clarifies the cells that have entered the volume of fluid within the acoustic standing wave field). Once the tightly packed cell clusters have settled out (i.e., once the volume of fluid within the acoustic standing wave has been sufficiently clarified), the mode of operation is then again that of the second described mode of operation, namely, the acoustic interface effect. It is important to note that the device can operate in both/either of the modes of operation, as described above, without external switching. In other words, the properties of the fluid streams, e.g., cell concentrations in the streams, and acoustic field dictate which mode dominates.

The acoustic standing wave(s) perfusion devices of the present disclosure are operated differently compared to prior acoustic filter usages, previously described in literature. Previously, acoustophoresis was operated such that the protein-producing materials, such as Chinese hamster ovary cells (CHO cells), the most common host for the industrial production of recombinant protein therapeutics, were trapped within a planar ultrasonic standing wave (i.e., remain in a stationary position). Cells were retained in an acoustic field by causing individual cells to migrate towards the pressure nodal planes of the planar acoustic standing wave. There, as the cells were retained in the standing wave, there was also a physical scrubbing of the cell culture media flowing past, whereby more cells were trapped as they came in contact with the cells that were already held within the standing wave. The standing wave and harvest fluid flow were then intermittently shut off to allow the cells to drop out of the standing wave and return to the bioreactor.

In contrast, in the present disclosure, the ultrasonic standing waves are used as a blanket or selector or "force field". Rather than just trapping and retaining the biological cells within the standing wave, fluid flows through the perfusion device in a manner such that gravity first operates on the biological cells, causing them to sink. The standing wave is created near the top of the filtering device and acts like a filter to prevent the cells from entering the acoustic field and exiting through the top of the filtering device (i.e., acting similar to a force field holding the cells back from entering the acoustic field). Thus, two output streams are created, one output stream retaining the cells and exiting through a port at the bottom of the device, and the other output stream being depleted in cells and exiting through a port at the top of the device (the cell concentration in the two output streams being compared to each other). In this mode of operation, there is almost no reliance on clustering, clumping, or agglomeration of the cells within the acoustic field. This mode may be particularly advantageous in certain applications as it does not necessarily rely on retention time of the cells in the acoustic filtering device.

Described another way, the acoustic perfusion device has two fluid streams flowing at different rates. The main fluid stream, carrying the expressing cell culture, culture media, product, and other bioreactor constituents, enters the device and is partially diverted into a secondary, lower volume, lower flow fluid stream. This secondary fluid stream passes through the multi-dimensional acoustic standing wave, where the multi-dimensional acoustic standing wave (or generally the interface effect created by the acoustic standing wave) holds back the main cell culture and allows the expressed biomolecules, the monoclonal antibodies and recombinant proteins, along with other small particles such as submicron and micron-sized cell debris, to pass through and be further collected and processed outside/downstream of the bioreactor. The main fluid stream, containing the main cell culture, is then recycled back to the bioreactor. The acoustic standing wave and its "interface effect" can be considered to act as a filter, preventing large cells, other particles or bodies, from exiting the bioreactor.

In another application, the acoustic perfusion devices can act as a retention device and cell washing device for cell therapy applications. In continuous cell-culture applications, such as autologous and allogeneic cell therapy, cells may be purified, isolated, and/or proliferated that are initially harvested at a very low cell-density. Relatively few cells can be used to seed a bioreactor, with the intention of increasing the number of cells. Further processing steps such as concentrating, washing, and/or media exchange may be used for various applications. These applications may include operations to continuously circulate, add, and/or remove media while retaining cells in a bioreactor (which may be traditional or single-use) with little or no effect to their viability. The acoustic cell retention systems described herein operate over a range of cell recirculation rates, efficiently retain cells over a range of perfusion (or media removal rates), and can be tuned to fully retain or selectively pass some percentage of cells through fluid flow rate, transducer power or frequency manipulation. Power and flow rates can all be monitored and used as feedback in an automated control system. Specialty flow paths may also be used such that a small volume of the main fluid flow is "sipped" off and the expressed biomolecules are separated from the main cell culture.

One advantage of acoustophoresis is that the acoustic radiation force does not harm or negatively affect the biological cells or the desired biomolecule product. Moreover, perfusion is continuous, such that the cell culture is kept viable and desired products can be continually recovered therefrom.

In a perfusion bioreactor system, it is desirable to be able to filter and separate the viable biological cells from the expressed materials that are in the fluid stream (i.e., cell culture media) and cellular debris. As previously mentioned, such biological cells may include Chinese hamster ovary (CHO) cells, whose cell genome is manipulated to express large biomolecules. Such biomolecules can include recombinant proteins or monoclonal antibodies, and are the desired product to be recovered.

The acoustic perfusion devices of the present disclosure are designed to maintain a high intensity multi-dimensional acoustic standing wave that can act as a filter, permitting smaller particles (such as recombinant proteins or cellular debris) to pass through while excluding larger particles (such as viable cells). In some examples, the device is driven by an oscillator and amplifier (not shown), and the device performance is monitored and controlled by a computer (not shown). Acoustic streaming can be controlled by modulating the frequency or amplitude of the standing wave. The modulation or control may be implemented by amplitude modulation, including voltage and/or current amplitude modulation, and/or by frequency modulation, which may include phase angle modulation. The duty cycle of the propagation of the standing wave may also be utilized to achieve certain results (i.e. the acoustic beam may be turned on and shut off at different time periods or rates).

FIG. 1 illustrates a single standing wave system 100 that is comprised of a reflector plate 101 and an ultrasonic transducer 103 that is set to resonate so as to form a standing wave 102. Excitation frequencies typically in the range from 100 kHz to 100 MHz are applied by the transducer 103. One or more multi-dimensional standing waves are created between the transducer 103 and the reflector 101. An ideal standing wave is the sum of two propagating waves that are equal in frequency and intensity and that are traveling in opposite directions, i.e. from the transducer to the reflector and back. The propagating waves constructively interfere with each other and thus generate the standing wave. A dotted line 105 is used to indicate the zero-amplitude of the wave. A node is a point where the wave has minimum amplitude, and is indicated with reference numeral 107. An anti-node is a point where the wave has maximum amplitude, and is indicated with reference numeral 109.

Figure 2:
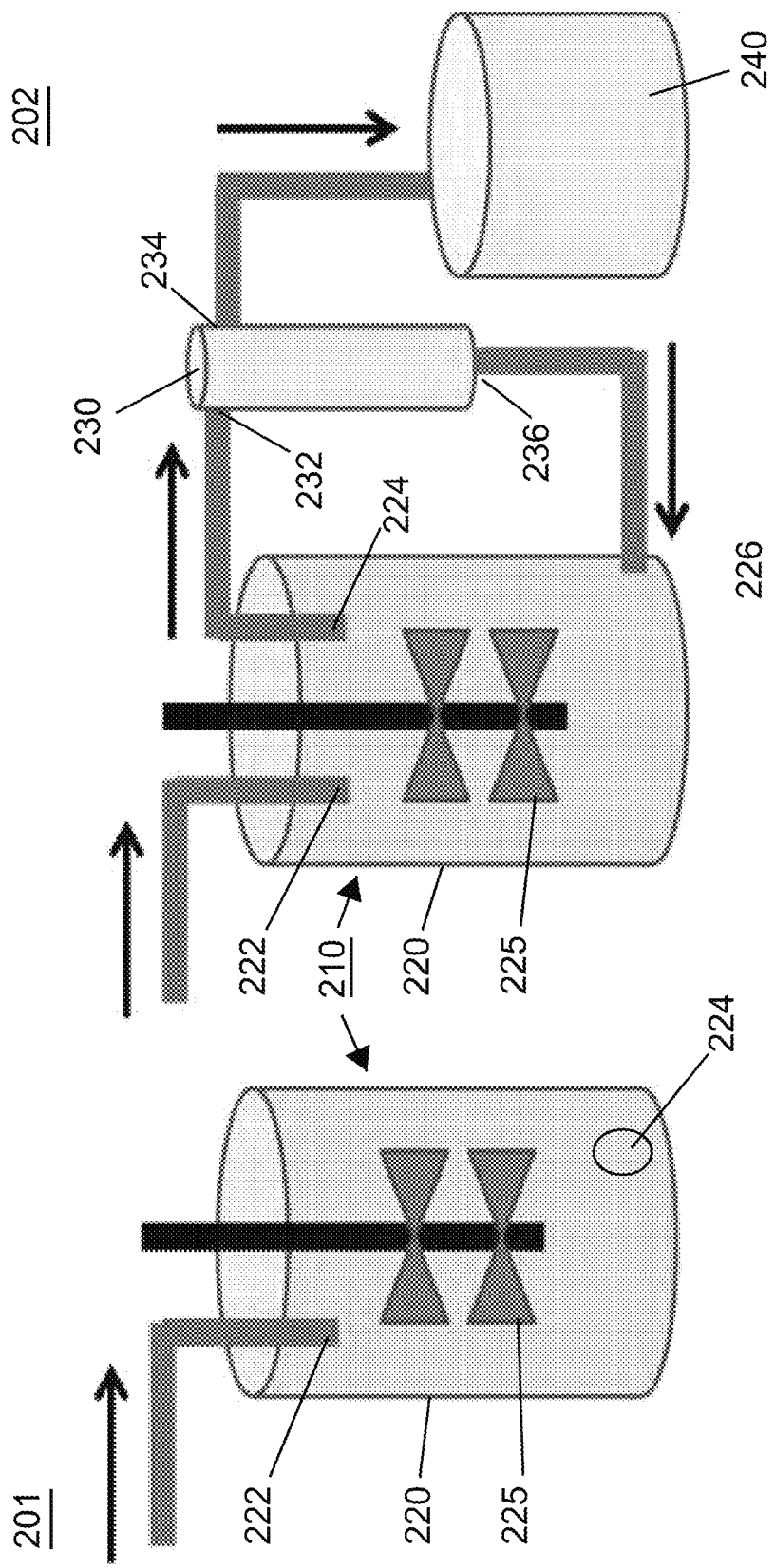
FIG. 2 is an illustration comparing a fed-batch bioreactor system with a perfusion bioreactor system.

FIG. 2 is a schematic diagram that compares a fed-batch bioreactor system 201 (left side) with a perfusion bioreactor system 202 (right side). Beginning with the fed-batch bioreactor on the left, the bioreactor 210 includes a reaction vessel 220. The cell culture media is fed to the reaction vessel through a feed inlet 222. An agitator 225 is used to circulate the media throughout the cell culture. Here, the agitator is depicted as a set of rotating blades, though any type of system that causes circulation may be used. The bioreactor permits growth of a seed culture through a growth/production cycle, during which time debris, waste and unusable cells will accumulate in the bioreactor and the desired product (e.g. biomolecules such as monoclonal antibodies, recombinant proteins, hormones, etc.) will be produced as well. Due to this accumulation, the reaction vessel of a fed-batch process is typically much larger than that in a perfusion process. The desired product is then harvested at the end of the production cycle. The reaction vessel 220 also includes an outlet 224 for removing material.

Turning now to the perfusion bioreactor 202 on the right-hand side, again, the bioreactor includes a reaction vessel 220 with a feed inlet 222 for the cell culture media. An agitator 225 is used to circulate the media throughout the cell culture. An outlet 224 of the reaction vessel is fluidly connected to the inlet 232 of an acoustic perfusion device 230 of the present disclosure, and continuously feeds the bioreactor contents (containing cells and desired product) to the filtering device. The perfusion device is located downstream of the reaction vessel, and separates the desired product from the cells. The acoustic perfusion device 230 has two separate outlets, a product outlet 234 and a recycle outlet 236. The product outlet 234 fluidly connects the acoustic perfusion device 230 to a containment vessel 240 downstream of the perfusion device, which receives the flow of the desired product (plus media) from the perfusion device. From there, further processing/purification can occur to isolate/recover the desired product. For example, further downstream of this acoustic perfusion device may be additional filters such as an ATF, TFF, depth filter, centrifuge, etc. The recycle outlet 236 fluidly connects the acoustic perfusion device 230 back to a recycle inlet 226 of the reaction vessel 220, and is used to send the cells and cell culture media back into the reaction vessel for continued growth/production. Put another way, there is a fluid loop between the reaction vessel and the perfusion device. The reaction vessel 220 in the perfusion bioreactor system 202 has a continuous throughput of product and thus can be made smaller. The filtering process is critical to the throughput of the perfusion bioreactor. A poor filtering process will allow for only low throughput and result in low yields of the desired product.

Figure 3:
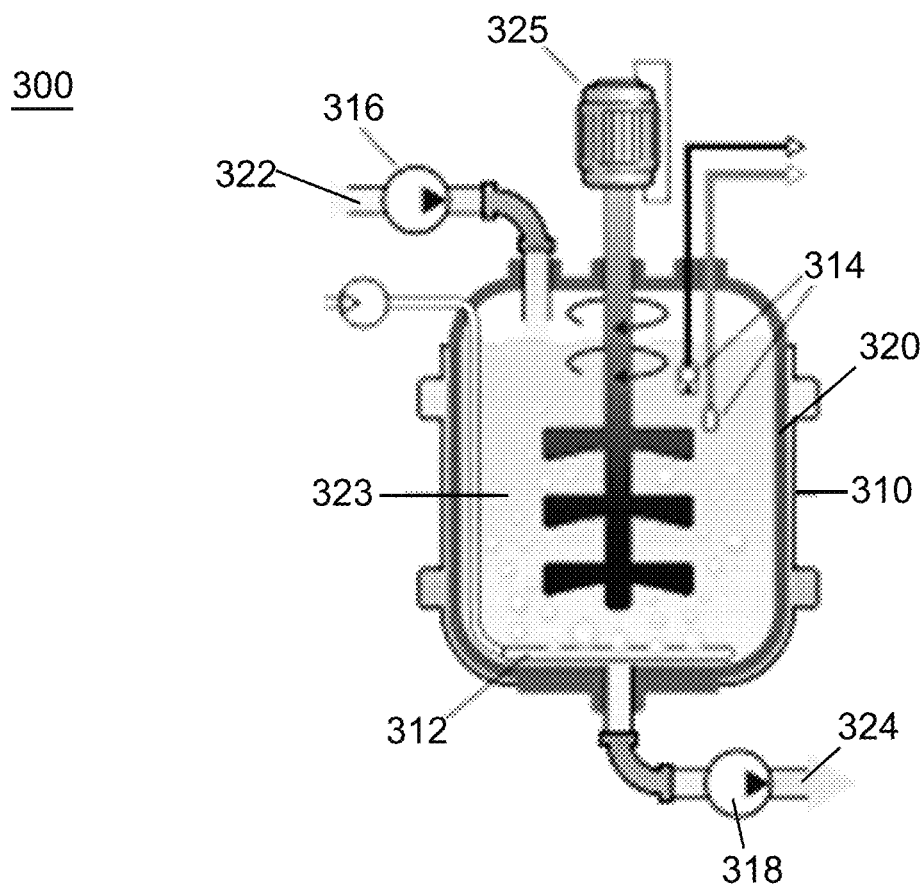
FIG. 3 is a cross-sectional view that shows the various components of a stirred-tank bioreactor.

FIG. 3 is a cross-sectional view of a generic bioreactor 300 that is useful for the systems of the present disclosure. As illustrated here, the bioreactor includes a reaction vessel 320 having an internal volume 323. A feed inlet 322 at the top of the vessel is used to feed cell culture media into the vessel. An agitator 325 is present. An outlet 324 is shown at the bottom of the vessel. A thermal jacket 310 surrounds the reaction vessel, and is used to regulate the temperature of the cells/media. An aerator 312 is located on the bottom of the vessel for providing gas to the internal volume. Sensors 314 are shown at the top right of the vessel. A pump 316 is illustrated for feeding the cell culture media into the vessel, as is another pump 318 for removing cell culture media from the vessel.

The perfusion systems described above use an acoustic perfusion device of the present disclosure. The contents of the bioreactor are continuously flowed through the acoustic perfusion device to capture the desired products.

In some embodiments, the acoustic perfusion device includes an inlet port, an outlet port, a first collection port, a bottom wall, and an acoustic chamber. The acoustic chamber can also be referred to as a fluid cell.

The inlet port is located at a first end of the device. Generally, the inlet port is fluidly connected to an associated bioreactor and serves as the inlet through which the fluid mixture with cells, fines, and product is introduced to the device. An inlet flow path leads from the inlet port to the acoustic chamber, which contains an internal volume. An upper wall can be present above the inlet flow path leading from the inlet port to the acoustic chamber, the upper wall having a substantially horizontal orientation. The inlet flow path has a cross-sectional area.

The inlet port is located at a first height above the outlet port, which defines a bottom end of the device. Put another way, the outlet port is located below the acoustic chamber or below the inlet port, or at the bottom end of the device. The placement of the outlet port below the inlet port ensures that fluid flow through the device is passively urged by gravity towards the outlet port, and that a hydraulic head is created within the device. The outlet port may also be referred to as a fluid recycle port because the host fluid is recycled or returned from the device to the associated bioreactor through the outlet port. The outlet port is also located at a second end of the device, opposite the first end. The first end and second end can be considered as being opposite ends of an x-axis, while the bottom end and top end can be considered as being opposite ends of a z-axis.

The first collection port is located above the acoustic chamber at the top end of the device, and is fluidly connected to the acoustic chamber. The device may include additional collection ports, such as second collection port, which is spaced apart from the first collection port. The first and second collection ports, are generally used to harvest and recover a portion of the desired biomolecule byproducts from the device. A collection or harvest flow path leads from the acoustic chamber to the collection ports. The collection flow path has a cross-sectional area. In some particular embodiments, the cross-sectional area of the collection flow path is greater than the cross-sectional area of the inlet flow path. This is one method by which the flow rate of fluid through the collection ports, can be made much lower than the incoming flow rate of fluid. When used in perfusion biomanufacturing, the collection ports can also be referred to as perfusion or harvest ports. Because fluid depleted in cells and enriched in desired biomolecule products, cell debris, and other fines is harvested, the collection ports can also be referred to as harvest ports, and the collection flow path can also be referred to as the harvest flow path.

In some embodiments, the bottom wall extends from the inlet port to the outlet port of the device. The exact shape of the bottom wall can vary to obtain the desired fluid flow. The bottom wall can curve in a concave fashion from the inlet port to the outlet port of the device. An outlet flow path leads from the acoustic chamber to the outlet port.

A first ultrasonic transducer can be located on a sidewall of the device at a second height that is above the first height (i.e. closer to the top end of the device) and below the collection ports. This volume above the acoustic chamber and below the collection ports can be identified as a harvest or collection zone. The first ultrasonic transducer includes a piezoelectric material that can be driven (e.g. by a voltage signal) to create a multi-dimensional standing wave in the acoustic chamber across the collection flow path. An acoustic radiation force field thus separates the acoustic chamber from the collection ports.

The acoustic perfusion device may include a reflector located on a wall opposite from the first ultrasonic transducer. The reflector is also located at the second height (i.e. the same height as the transducer). Together, the transducer and reflector generate a multi-dimensional acoustic standing wave, as illustrated in FIG. 1.

In some embodiments, the inlet port, outlet port, and the collection ports may all be located on a front wall of the device. The ports can face in any other direction, as desired. The front wall can have a flat or planar face, and has a constant thickness. However, the shape of the front wall may also vary if desired, for example to change the cross-sectional areas. Finally, the rear wall of the device is attached to a mounting piece, which contains holes for attaching the perfusion device to a surface for operation.

The flow rate through the collection or harvest flow path is, in various embodiments, at least one order of magnitude smaller than the flow rate through the inlet flow path. In more particular embodiments, the flow rate of the fluid mixture entering the device through the inlet port is about 1 liter per minute (L/min) and the flow rate of the fluid depleted in cells exiting the device through the collection port(s) is about 10 milliliters per minute (mL/min). In some tests, bioreactors having a size of 2 liters to 10 liters have been tested with solutions containing up to 10% yeast and up to 50 million cells/mL. The flow rate through the inlet port has been from about 0.75 L/min to about 3 L/min, with the flow rate through the collection flow path (i.e. all collection ports together) being about 1 mL/min to about 30 mL/min. A 95% cell recovery rate has been achieved.

The acoustic perfusion devices of the present disclosure can filter very high cell densities, around 100 million cells per mL and possibly in the range of about 20 million to about 120 million cells per mL, whereas other filtering technologies such as ATF can only filter at densities less than 80 million cells per mL. Unlike hollow fiber membranes, the acoustic standing wave(s) can also be tuned to allow passage of cells if desired, as well as allow the passage of fines/debris. This can act as a cleaning operation for the bioreactor. Continuous, steady-state operation is possible without pressure fluctuations, and the product stream does not accumulate in the bioreactor or the filtering device.

The acoustic perfusion device can be made of appropriate materials, such as, for example, high density polyethylene (HDPE), other plastics, metals and/or glasses. It has been found very convenient for the device to be transparent, so that fluid flow and ultrasonic transducer operation can be visually confirmed.

Figure 4:
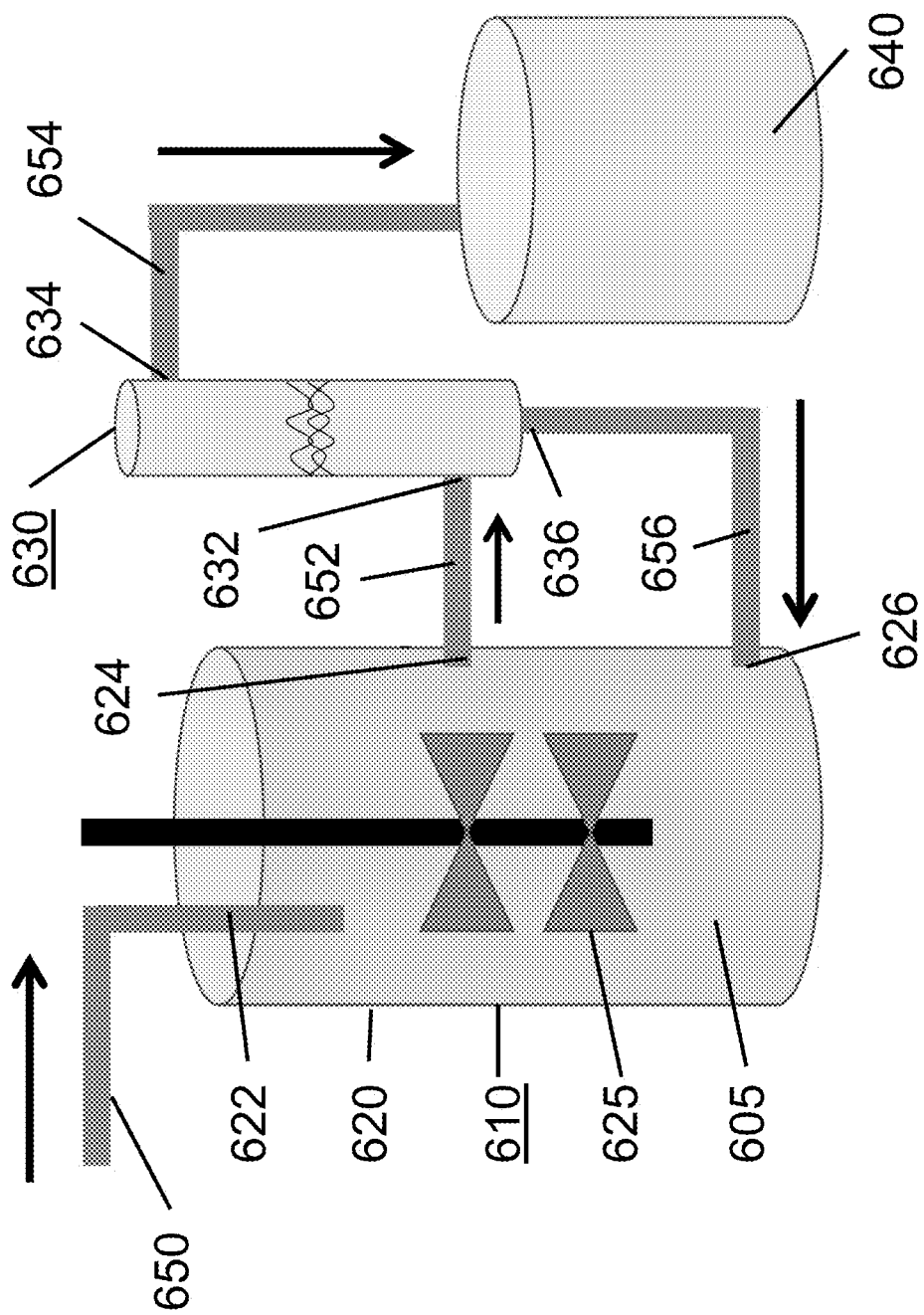
FIG. 4 is a schematic view illustrating a perfusion bioreactor coupled with an acoustic perfusion device of the present disclosure, and a recycle path.

Turning now to FIG. 4, a processing system is shown including an associated bioreactor 610 and an acoustic perfusion device 630 of the present disclosure. The system is set up for use as a perfusion bioreactor. The bioreactor 610 includes a reaction vessel 620 having a feed inlet 622, an outlet 624, and a recycle inlet 626. Fresh media is added into the feed inlet 622 by an addition pipe 650. Some reactors will also include an outlet or bleed port (not shown here) to remove or "bleed" cells in order to maintain a constant cell density within a reactor. The contents of the reaction vessel (reference numeral 605) are mixed with an agitator 625. The desired product (e.g., recombinant proteins) is continuously produced by cells located within the vessel 620, and are present in the media of the bioreactor. The product and the cells in the perfusion bioreactor are drawn from the reaction vessel through pipe 652, and enter the acoustic perfusion device 630 through inlet port 632. Therein, a portion of the desired product is separated from the cells. The desired product can be drawn off through a first collection port 634 (which is a product recovery port) and pipe 654 into a containment vessel 640, or in the case of a truly continuous production system, some other downstream purification process. The cells are returned to the perfusion bioreactor after separation, passing from outlet port 636 (which is a fluid recycle port) of the acoustic perfusion device through pipe 656 to recycle inlet 626 of the reaction vessel, which form a recycle path. The multi-dimensional standing wave(s) of the acoustic perfusion device are used to create a separation barrier between the fluid cell of the device and the collection port, so that a highly reduced number of biological cells are collected in collection port 634.

Figure 5:
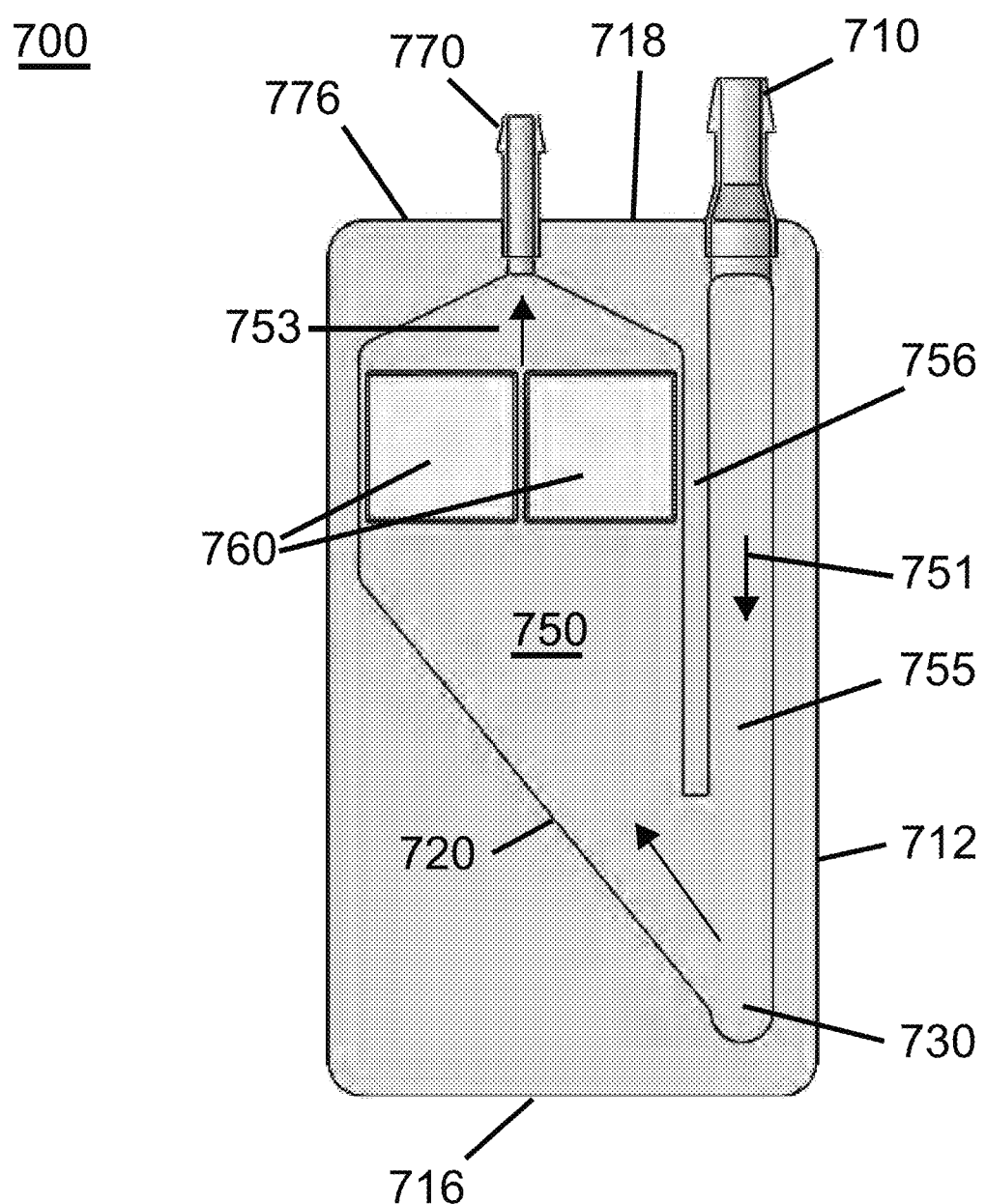
FIG. 5 is a front cross-sectional view of an example implementation of an acoustic perfusion device of the present disclosure.
Figure 6:
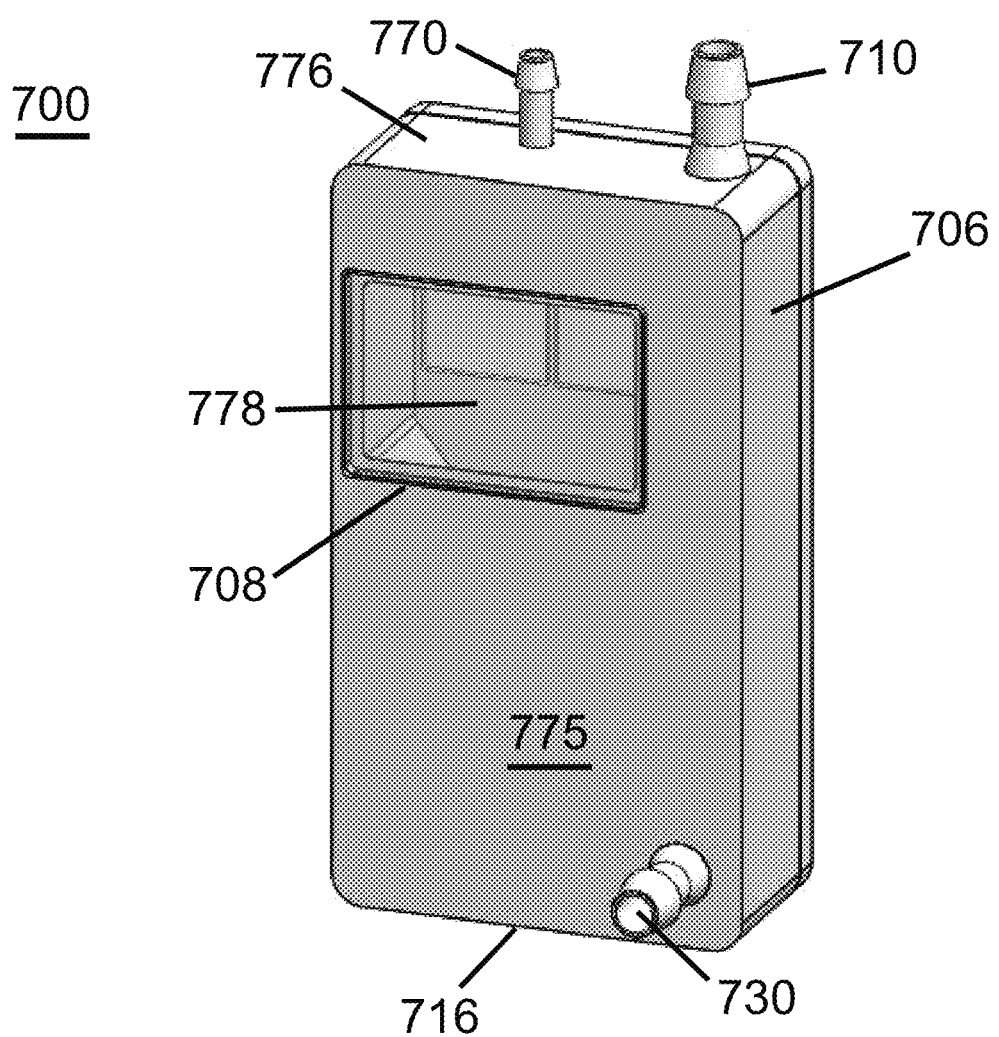
FIG. 6 is an exterior perspective view of the acoustic perfusion device of FIG. 5.

FIG. 5 and FIG. 6 are views of another exemplary embodiment of an acoustic perfusion device. FIG. 5 is a front cross-sectional view, and FIG. 6 is an exterior perspective view. Notably, this embodiment is specifically designed such that it can be fabricated with clean machining techniques, using Class VI materials (medical device grade HDPE, for example), or even as single or welded injection molded part. In this manner, this embodiment is an example of a single-use device, which is gamma-stable. The devices are flushed to remove bioburden and then gamma-irradiated (generally from 25-40 kGy) to sterilize any potential contamination that could destroy a healthy cell culture, such as that present in a perfusion bioreactor.

Referring first to FIG. 5, in this device 700, the inlet port 710 and the collection port 770 are both located at the top end 718 of the device, or on the top wall 776 of the device. The outlet port 730 is located at a bottom end 716 of the device. Here, the inlet port 710 and the outlet port 730 are both on a first side 712 of the device. The inlet flow path 751 is in the form of a channel 755 that runs from the inlet port downwards towards the bottom end and past the outlet port, the channel being separated from the acoustic chamber 750 (here, the separation occurring by an internal wall 756). Fluid will flow downwards in the channel, then rise upwards into the acoustic chamber 750. The bottom wall 720 of the acoustic chamber is a sloped planar surface that slopes down towards the outlet port 730. The location of the ultrasonic transducers 760 are shown here as two squares, between the top end and the bottom end of the device. The collection flow path 753 is located above the transducers.

Referring now to FIG. 6, the device 700 is shown as being formed within a three-dimensional rectangular housing 706. It can be seen that the outlet port 730 at the bottom end 716 of the device is located on a front wall 775. Again, the collection port 770 and the inlet port 710 are located on a top wall 776. A viewing window 708 made of a transparent material is present in the front wall. Through that viewing window, it can be seen that the ultrasonic transducers are mounted in the rear wall 778 of the device housing. The viewing window acts as a reflector to generate the multi-dimensional acoustic standing waves.

Figure 7:
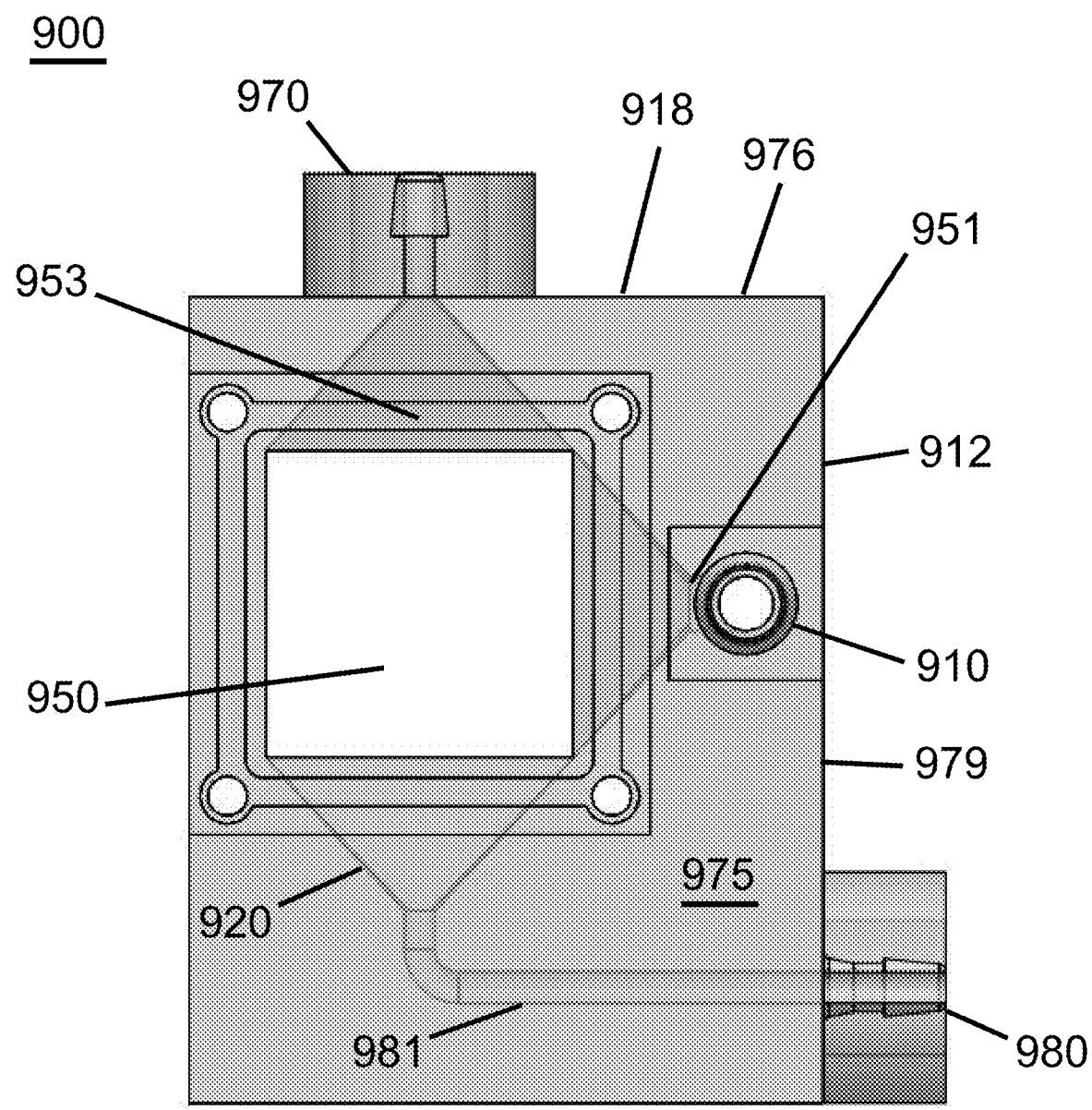
FIG. 7 is a front cross-sectional view of another example implementation of an acoustic perfusion device of the present disclosure.
Figure 8:
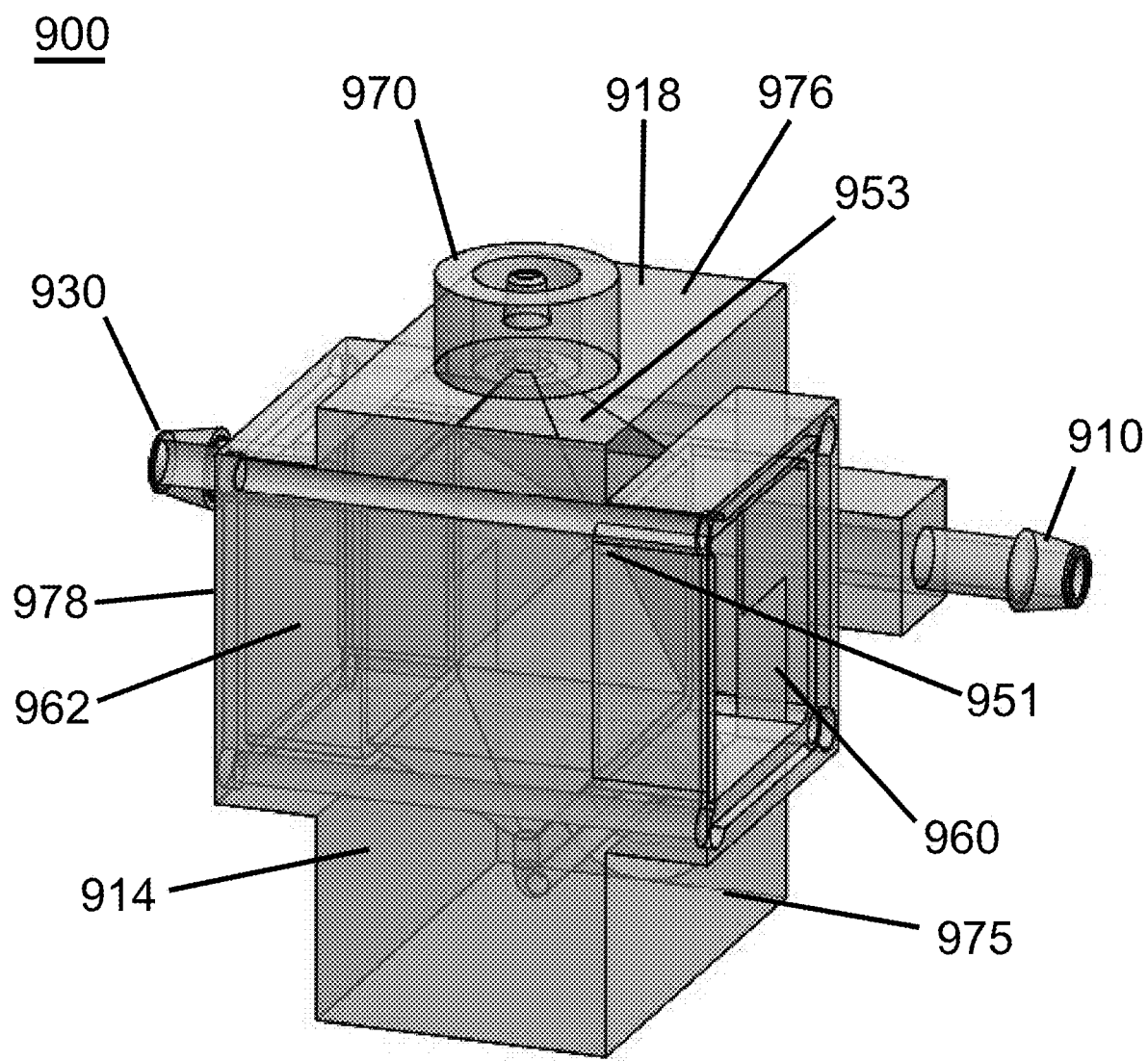
FIG. 8 is a perspective view of the acoustic perfusion device of FIG. 7.

FIG. 7 and FIG. 8 are views of yet another exemplary embodiment of an acoustic perfusion device. FIG. 7 is a front cross-sectional view, and FIG. 8 is a perspective view.

Referring first to FIG. 7, in this device 900, there is an inlet port 910 present on a front side 975 of the device along the first side 912 of the device. An outlet port 930 (best seen in FIG. 8) is located directly opposite and at the same height as the inlet port 910, and is also located on first side 912. In this embodiment, there is a main fluid stream that flows almost directly from the inlet port 910 to the outlet port 930, and the inlet flow path 951 diverts only a small side flow into the acoustic chamber 950 from the first side 912 of the device. The collection port 970 is located at the top end 918 of the device, or on the top wall 976 of the device. A secondary outlet port 980 is located on the first side 912 of the device as well, extending from first side wall 979, and located below the inlet port 910, and can act as a bleed port. The bottom wall 920 of the acoustic chamber is shaped in a pyramid-like fashion to taper downwards to a vertex. A drain line 981 runs from the bottom of the acoustic chamber 950 to the secondary outlet port 980. The secondary outlet port can be used to capture a small flow of highly concentrated cells, which can either be discarded (cell bleed) or can also be returned back to the bioreactor.

Referring now to FIG. 8, the front wall 975 of the device has a rectangular space 960, and the rear wall 978 of the device has a rectangular space 962. One transducer and one reflector can be placed in these two rectangular spaces 960/962 in either orientation, or that two transducers could be placed in the two rectangular spaces. The inlet port 910 and outlet port 930 are both visible in this view. The inlet port 910 is located on the front side of the device, and the outlet port 930 is located on the rear side of the device (though this could be reversed if desired). The clarification flow path 953 is located above the transducers. Although not depicted here, a mounting piece similar to that in FIG. 4 could be attached to the second side 914 of the device.

Figure 27:
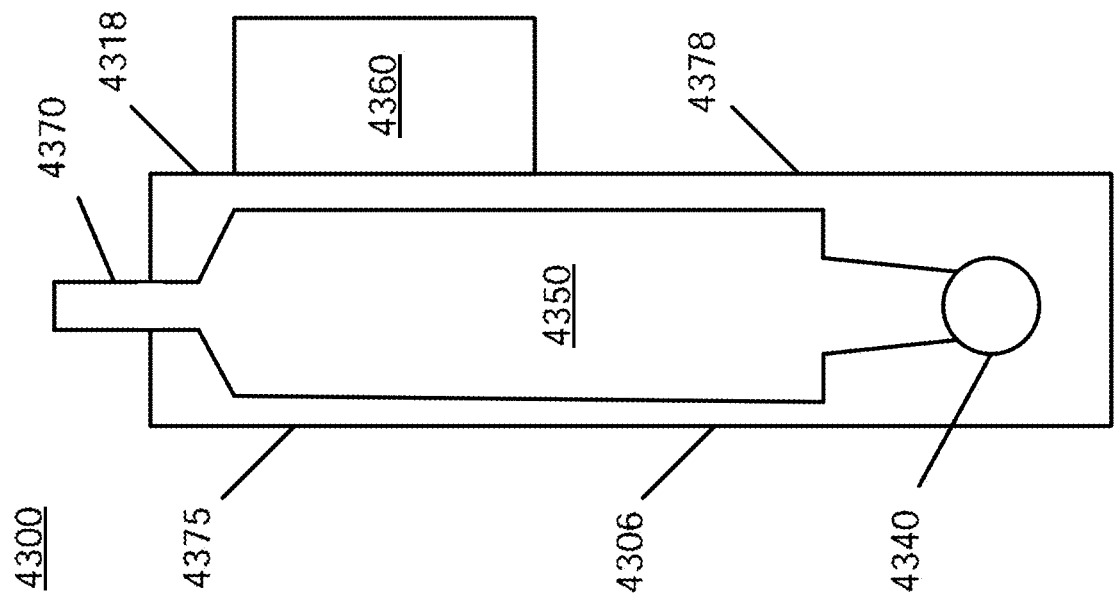
FIG. 27 is a diagrammatic side view of the device of FIG. 25.

FIGS. 25-27 are views of yet another exemplary embodiment of an acoustic perfusion device. FIG. 25 is a perspective view, FIG. 26 is a picture showing a front view, and FIG. 27 is a side view.

Referring now to FIGS. 25-27, in this device 4300, the inlet port 4310 and the outlet port 4330 are both located at the bottom end 4316 of the device, and the collection port 4370 is located at the top end 4318 of the device. The inlet port 4310 is located on a first side 4312 of the device, and the outlet port 4330 is located on a second side 4314 of the device. In FIG. 25, the outlet port 4330 is attached to a pump 4305, which creates flow through the device 4300. A viewing window 4308 is present on the front wall 4375 of the device. The front wall 4375, top wall 4376, rear wall 4378, and first side wall 4379 are part of the housing 4306 that surrounds the interior of the device.

Referring now to FIG. 25 and FIG. 27, the ultrasonic transducer 4360 is located on the rear wall 4378 at the top end 4318 of the device. The viewing window 4308 acts as a reflector to generate the multi-dimensional acoustic standing waves.

In this embodiment, a recirculation pipe 4340 connects the inlet port 4310 directly to the outlet port 4330, and forms a recirculation flow path (arrow 4356) through which cell culture media containing cells and other materials can be continuously recirculated through the perfusion device without entering the acoustic chamber 4350. The recirculation pipe 4340 and the recirculation flow path 4356 are located below the acoustic chamber 4350.

An inflow passageway 4380 and an outflow passageway 4390 connect the acoustic chamber 4350 to the recirculation pipe 4340, and split off a portion of the flow of cell culture media from the recirculation pipe into the acoustic chamber. Arrow 4351 indicates the inlet flow path, and arrow 4355 indicates the outlet flow path. These two passageways are particularly visible in FIG. 26. Put another way, the inlet flow path travels through a different passage than the outlet flow path. This creates a secondary recirculating flow that is tangential to the acoustic interface, and allows for constant recirculation of cells beneath this acoustic interface, traveling in the same net direction as the recirculation flow path 4356.

All of the components of the acoustic perfusion devices of the present disclosure (i.e. housing, acoustic chamber, transducer, reflector) can be made of materials that are stable when exposed to gamma radiation (typically used for sterilization prior to usage). Examples of such gamma-stable materials can include plastics such as polyethylene, polypropylene, polycarbonates, and polysulfones, and potentially metals and glasses. The devices of the present disclosure can be operated as single-use, consumable, disposable devices. This prevents contamination of subsequent cell culture batches by previous cell culture batches.

Figure 9:
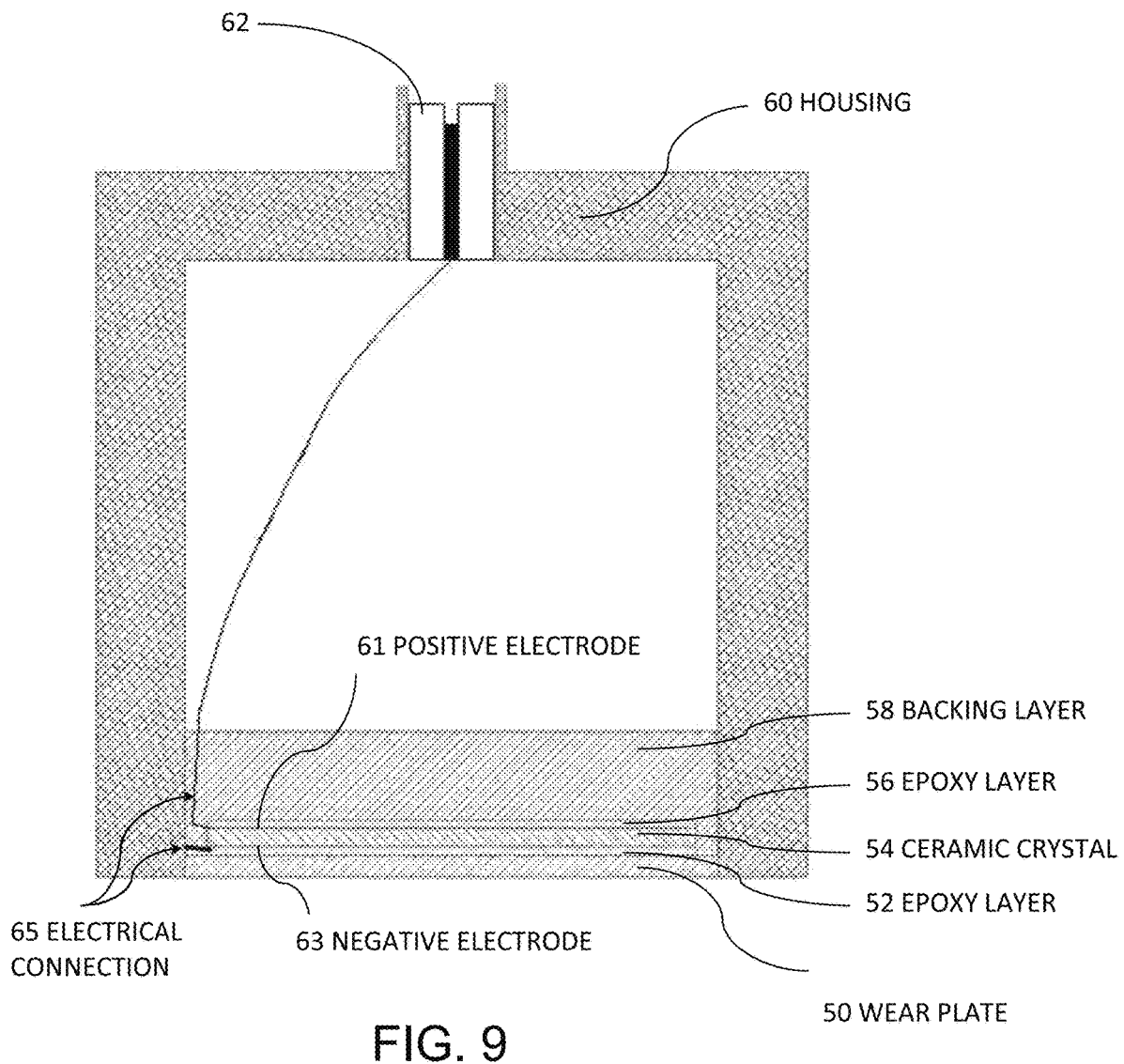
FIG. 9 is a cross-sectional diagram of a conventional ultrasonic transducer.

It may be helpful now to describe the ultrasonic transducer(s) used in the acoustic filtering device in more detail. FIG. 9 is a cross-sectional diagram of a conventional ultrasonic transducer. This transducer has a wear plate 50 at a bottom end, epoxy layer 52, ceramic piezoelectric element 54 (made of, e.g. Lead Zirconate Titanate (PZT)), an epoxy layer 56, and a backing layer 58. On either side of the ceramic piezoelectric element, there is an electrode: a positive electrode 61 and a negative electrode 63. The epoxy layer 56 attaches backing layer 58 to the piezoelectric element 54. The entire assembly is contained in a housing 60 which may be made out of, for example, aluminum. The housing is used as the ground electrode. An electrical adapter 62 provides connection for wires to pass through the housing and connect to leads (not shown) which attach to the piezoelectric element 54. Typically, backing layers are designed to add damping and to create a broadband transducer with uniform displacement across a wide range of frequency and are designed to suppress excitation of particular vibrational eigen-modes of the piezoelectric element. Wear plates are usually designed as impedance transformers to better match the characteristic impedance of the medium into which the transducer radiates.

Figure 10:
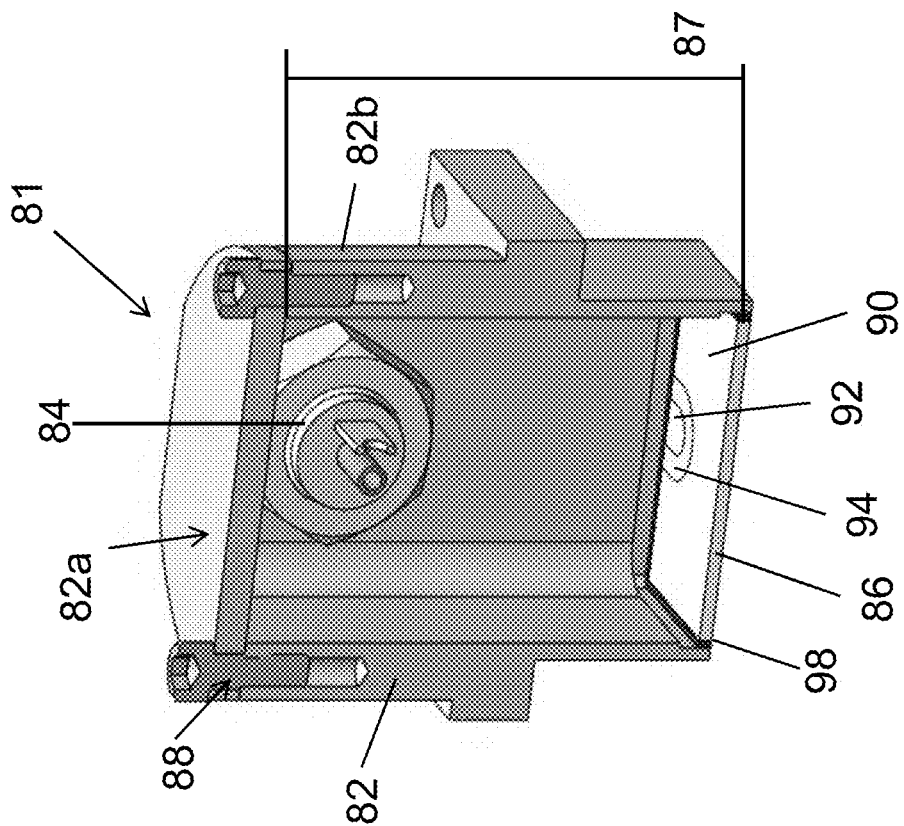
FIG. 10 is a cross-sectional diagram of an ultrasonic transducer of the present disclosure. An air gap is present within the transducer, and no backing layer or wear plate are present.

FIG. 10 is a cross-sectional view of an ultrasonic transducer 81 of the present disclosure, which is used in the acoustic filtering device of the present disclosure. Transducer 81 is shaped as a square, and has an aluminum housing 82. The aluminum housing has a top end and a bottom end. The transducer housing may also be composed of plastics, such as medical grade HDPE or other metals. The piezoelectric element is a mass of perovskite ceramic, each consisting of a small, tetravalent metal ion, usually titanium or zirconium, in a lattice of larger, divalent metal ions, usually lead or barium, and $O^{2-}$ ions. As an example, a PZT (lead zirconate titanate) piezoelectric element 86 defines the bottom end of the transducer, and is exposed from the exterior of the bottom end of the housing. The piezoelectric element is supported on its perimeter by a small elastic layer 98, e.g. epoxy, silicone or similar material, located between the piezoelectric element and the housing. Put another way, no wear plate or backing material is present. However, in some embodiments, there is a layer of plastic or other material separating the piezoelectric element from the fluid in which the acoustic standing wave is being generated. The piezoelectric material/element/crystal has an exterior surface (which is exposed) and an interior surface as well.

Figure 11:
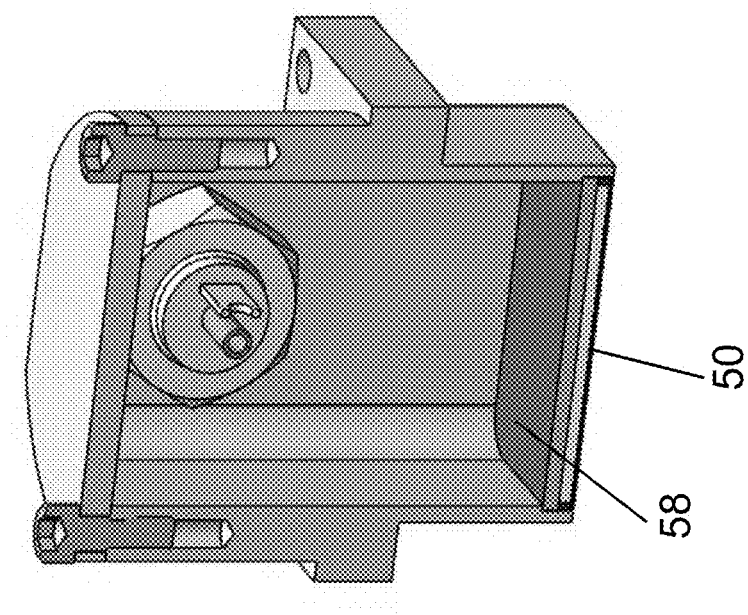
FIG. 11 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT piezoelectric element 86 is connected to a positive electrode 90 and a negative electrode 92, which are separated by an insulating material 94. The electrodes can be made from any conductive material, such as silver or nickel. Electrical power is provided to the PZT piezoelectric element 86 through the electrodes on the piezoelectric element. Note that the piezoelectric element 86 has no backing layer or epoxy layer. Put another way, there is an interior volume or an air gap 87 in the transducer between aluminum top plate 82a and the piezoelectric element 86 (i.e. the air gap is completely empty). A minimal backing 58 and/or wear plate 50 may be provided in some embodiments, as seen in FIG. 11.

The transducer design can affect performance of the system. A typical transducer is a layered structure with the ceramic piezoelectric element bonded to a backing layer and a wear plate. Because the transducer is loaded with the high mechanical impedance presented by the standing wave, the traditional design guidelines for wear plates, e.g., half-wavelength thickness for standing wave applications or quarter wavelength thickness for radiation applications, and manufacturing methods may not be appropriate. Rather, in one embodiment of the present disclosure the transducers, there is no wear plate or backing, allowing the piezoelectric element to vibrate in one of its eigenmodes with a high Q-factor, or in a combination of several eigenmodes. The vibrating ceramic piezoelectric element/disk is directly exposed to the fluid flowing through the fluid cell.

Removing the backing (e.g. making the piezoelectric element air backed) also permits the ceramic piezoelectric element to vibrate at higher order modes of vibration with little damping (e.g. higher order modal displacement). In a transducer having a piezoelectric element with a backing, the piezoelectric element vibrates with a more uniform displacement, like a piston. Removing the backing allows the piezoelectric element to vibrate in a non-uniform displacement mode. The higher order the mode shape of the piezoelectric element, the more nodal lines the piezoelectric element has. The higher order modal displacement of the piezoelectric element creates more trapping lines, although the correlation of trapping line to node is not necessarily one to one, and driving the piezoelectric element at a higher frequency will not necessarily produce more trapping lines.

In some embodiments of the acoustic filtering device of the present disclosure, the piezoelectric element may have a backing that minimally affects the Q-factor of the piezoelectric element (e.g. less than 5%). The backing may be made of a substantially acoustically transparent material such as balsa wood, foam, or cork which allows the piezoelectric element to vibrate in a higher order mode shape and maintains a high Q-factor while still providing some mechanical support for the piezoelectric element. The backing layer may be a solid, or may be a lattice having holes through the layer, such that the lattice follows the nodes of the vibrating piezoelectric element in a particular higher order vibration mode, providing support at node locations while allowing the rest of the piezoelectric element to vibrate freely. The goal of the lattice work or acoustically transparent material is to provide support without lowering the Q-factor of the piezoelectric element or interfering with the excitation of a particular mode shape.

Placing the piezoelectric element in direct contact with the fluid also contributes to the high Q-factor by avoiding the dampening and energy absorption effects of the epoxy layer and the wear plate. Other embodiments of the transducer(s) may have wear plates or a wear surface to prevent the PZT, which contains lead, contacting the host fluid. This may be desirable in, for example, biological applications such as separating blood, biopharmaceutical perfusion, or fed-batch filtration of mammalian cells. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface. Thin films, such as a PEEK film, can also be used as a cover of the transducer surface exposed to the fluid with the advantage of being a biocompatible material. In one embodiment, the PEEK film is adhered to the face of the piezomaterial using pressure sensitive adhesive (PSA). Other films can be used as well.

In some embodiments, for applications such as oil/water emulsion splitting and others such as perfusion, the ultrasonic transducer has a nominal 2 MHz resonance frequency. Each transducer can consume about 28 W of power for droplet trapping at a flow rate of 3 GPM. This translates to an energy cost of 0.25 kW hr/$m^3$. This is an indication of the very low cost of energy of this technology. Desirably, each transducer is powered and controlled by its own amplifier. In other embodiments, the ultrasonic transducer uses a square piezoelectric element, for example with 1"×1" dimensions. Alternatively, the ultrasonic transducer can use a rectangular piezoelectric element, for example with 1"×2.5" dimensions. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired multi-dimensional acoustic standing wave patterns.

The size, shape, and thickness of the transducer determine the transducer displacement at different frequencies of excitation, which in turn affects separation efficiency. Typically, the transducer is operated at frequencies near the thickness resonance frequency (half wavelength). Gradients in transducer displacement typically result in more trapping locations for the cells/biomolecules. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

To investigate the effect of the transducer displacement profile on acoustic trapping force and separation efficiencies, an experiment was repeated ten times using a 1"×1" square transducer, with all conditions identical except for the excitation frequency. Ten consecutive acoustic resonance frequencies, indicated by circled numbers 1-9 and letter A on FIG. 12, were used as excitation frequencies. The conditions were experiment duration of 30 min, a 1000 ppm oil concentration of approximately 5-micron SAE-30 oil droplets, a flow rate of 500 ml/min, and an applied power of 20 W. Oil droplets were used because oil is less dense than water, and can be separated from water using acoustophoresis.

Figure 12:
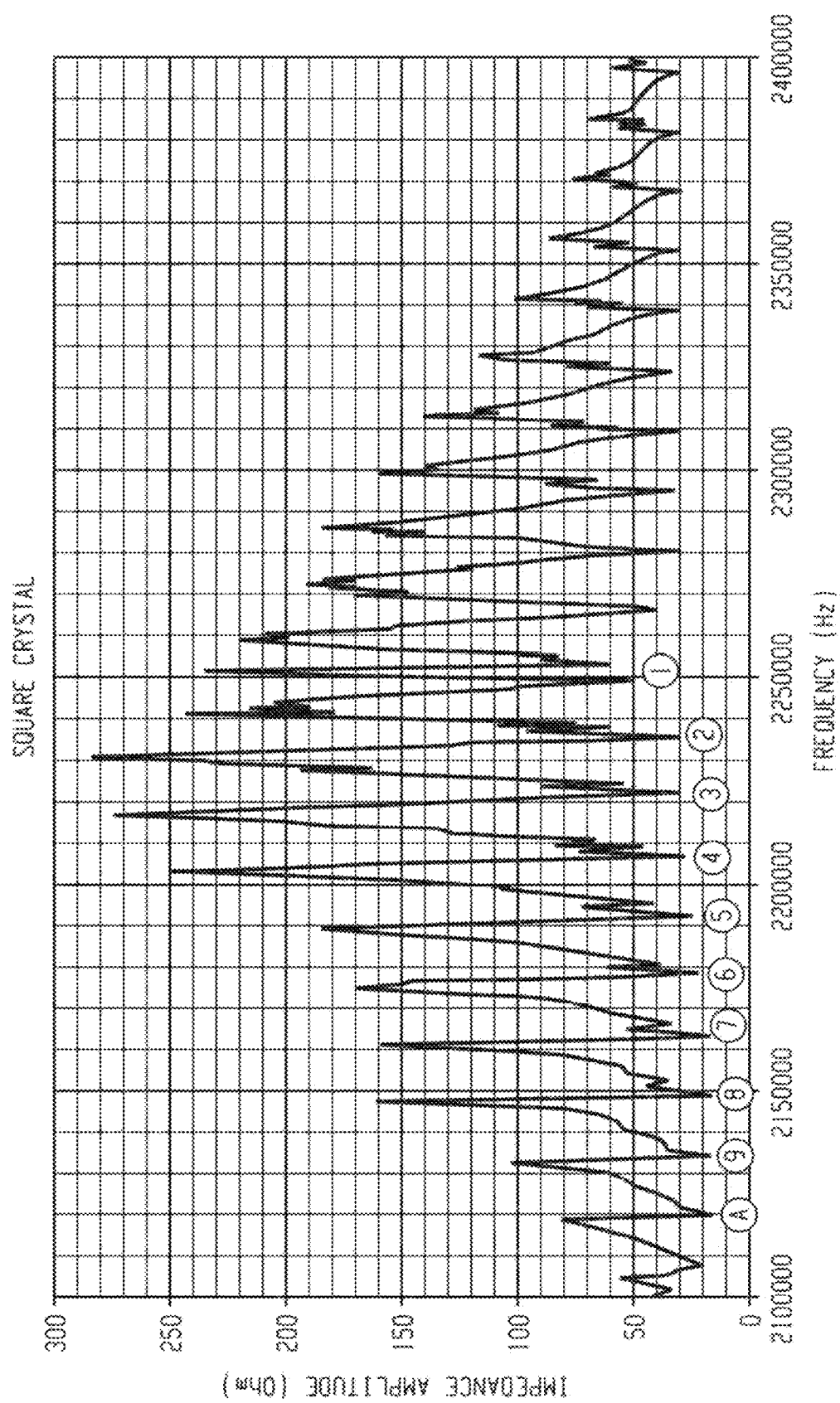
FIG. 12 is a graph of electrical impedance amplitude versus frequency for a square transducer driven at different frequencies.

FIG. 12 shows the measured electrical impedance amplitude of a square transducer as a function of frequency in the vicinity of the 2.2 MHz transducer resonance. The minima in the transducer electrical impedance correspond to acoustic resonances of the water column and represent potential frequencies for operation. Additional resonances exist at other frequencies where multi-dimensional standing waves are excited. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

Figure 13:
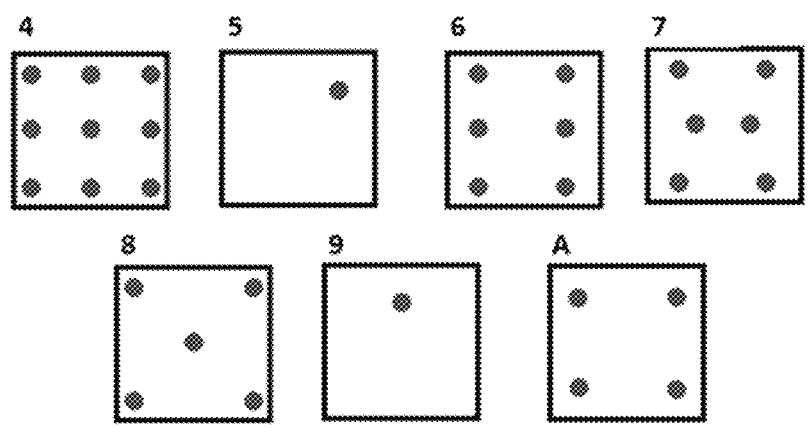
FIG. 13 illustrates the trapping line configurations for seven of the resonance frequencies (minima of electrical impedance amplitudes) of FIG. 12 from the direction orthogonal to fluid flow.

As the oil-water emulsion passed by the transducer, the trapping lines of oil droplets were observed and characterized. The characterization involved the observation and pattern of the number of trapping lines across the fluid channel, as shown in FIG. 13, for seven of the ten resonance frequencies identified in FIG. 12. Different displacement profiles of the transducer can produce different (more) trapping lines in the standing waves, with more gradients in displacement profile generally creating higher trapping forces and more trapping lines.

Figure 14:
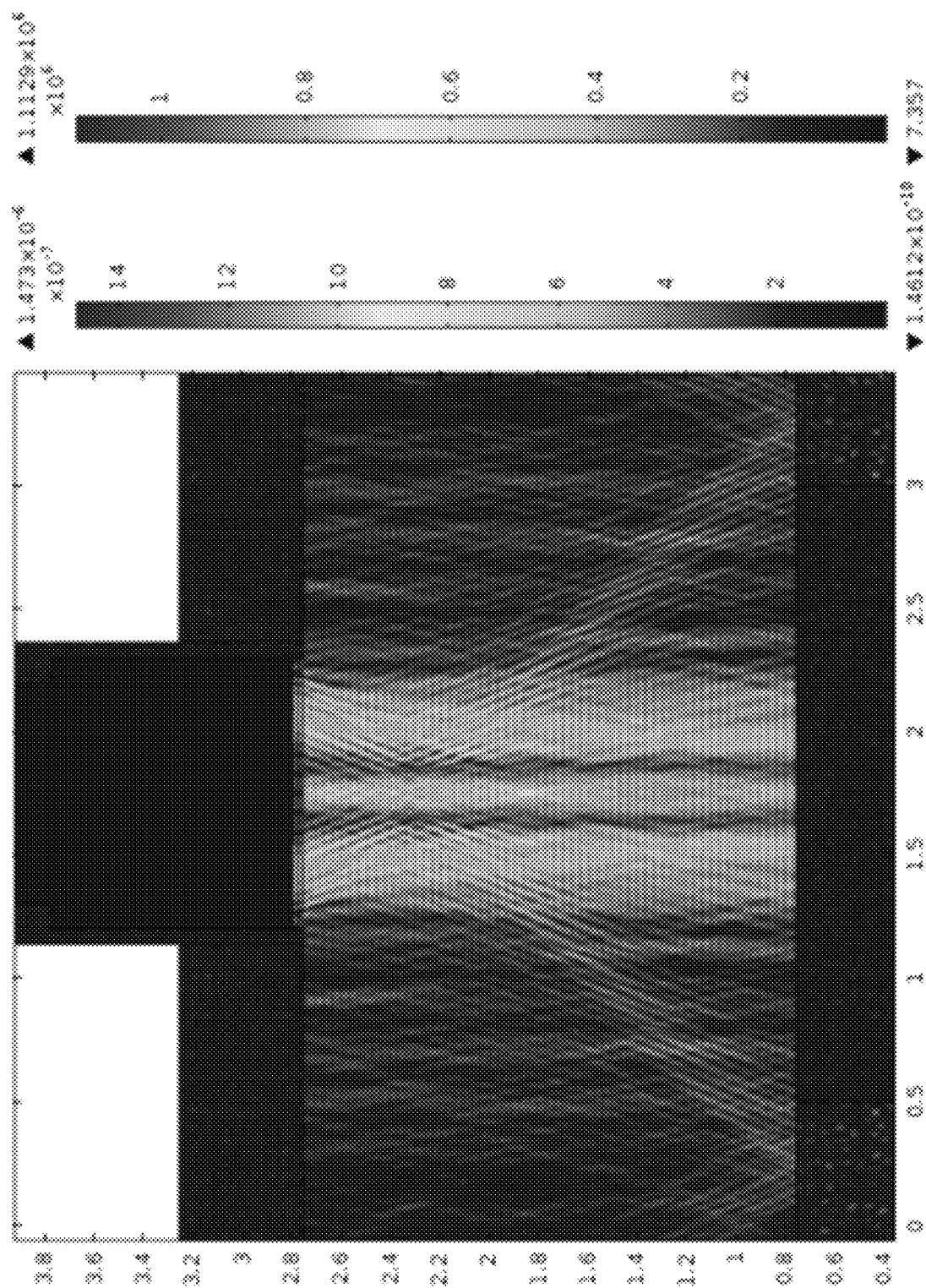
FIG. 14 is a computer simulation of the acoustic pressure amplitude (right-hand scale in Pa) and transducer out of plane displacement (left-hand scale in meters). The text at the top of the left-hand scale reads "×10$^{-7}$". The text at the top of the left-hand scale by the upward-pointing triangle reads "1.473×10$^{-6}$". The text at the bottom of the left-hand scale by the downward-pointing triangle reads "1.4612×10$^{-10}$". The text at the top of the right-hand scale reads "×10$^6$". The text at the top of the right-hand scale by the upward-pointing triangle reads "1.1129×10$^6$". The text at the bottom of the right-hand scale by the downward-pointing triangle reads "7.357". The triangles show the maximum and minimum values depicted in this figure for the given scale. The horizontal axis is the location within the chamber along the X-axis, in inches, and the vertical axis is the location within the chamber along the Y-axis, in inches.

FIG. 14 is a numerical model showing a pressure field that matches the 9 trapping line pattern. The numerical model is a two-dimensional model; and therefore only three trapping lines are observed. Two more sets of three trapping lines exist in the third dimension perpendicular to the plane of the page.

The lateral force of the acoustic radiation force generated by the transducer can be increased by driving the transducer in higher order mode shapes, as opposed to a form of vibration where the piezoelectric material (e.g., a piezoelectric crystal) effectively moves as a piston having a uniform displacement. The acoustic pressure is proportional to the driving voltage of the transducer. The electrical power is proportional to the square of the voltage. The transducer is typically a thin piezoelectric plate, with electric field in the z-axis and primary displacement in the z-axis. The transducer is typically coupled on one side by air (i.e., the air gap within the transducer) and on the other side by the fluid mixture of the cell culture media. The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Lamb waves exist in thin plates of infinite extent with stress free conditions on its surfaces. Because the transducers of this embodiment are finite in nature, the actual modal displacements are more complicated.

Figure 15:
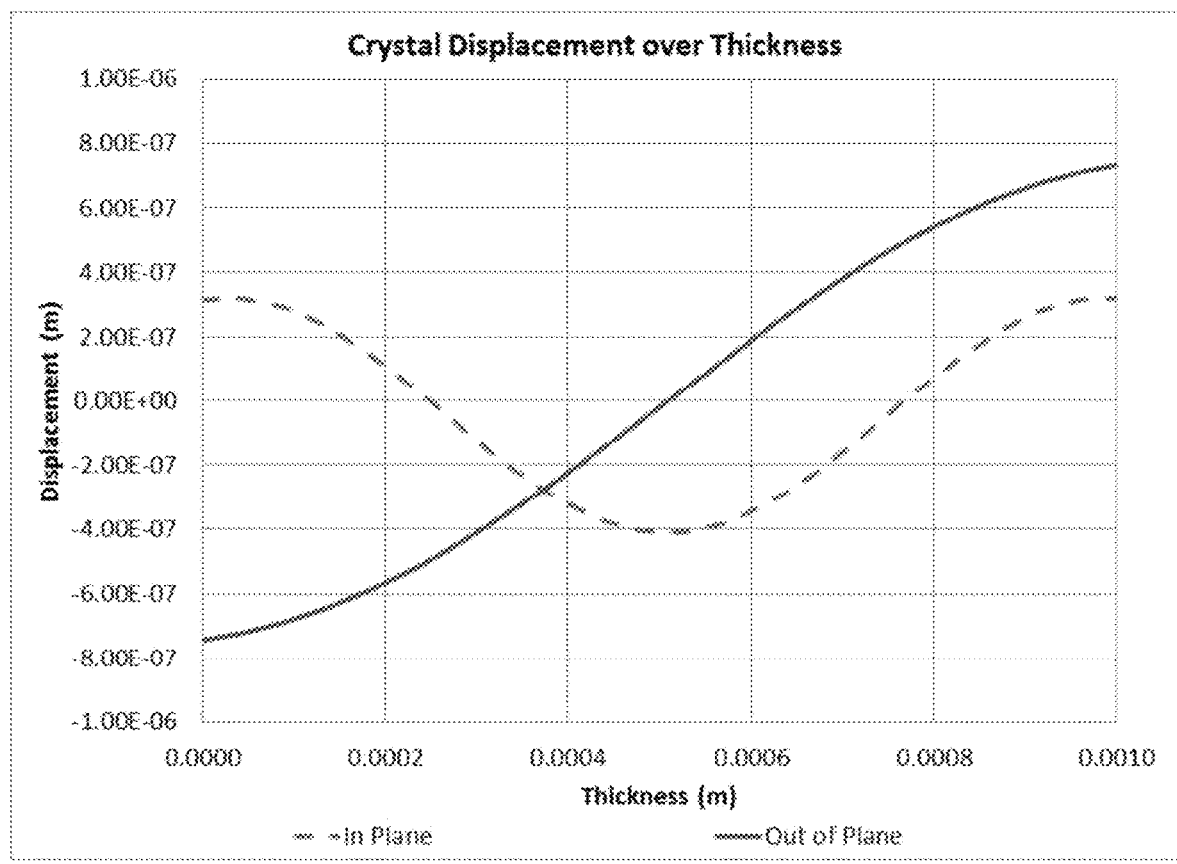
FIG. 15 shows the In-Plane and Out-of-Plane displacement of a crystal where composite waves are present.

FIG. 15 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. In general, a (m,n) mode is a displacement mode of the transducer in which there are m undulations in transducer displacement in the width direction and n undulations in the length direction, and with the thickness variation as described in FIG. 15. The maximum number of m and n is a function of the dimension of the piezoelectric material (e.g., a piezoelectric crystal) and the frequency of excitation. Additional three-dimensional modes exist that are not of the form (m,n).

The transducers are driven so that the piezoelectric element vibrates in higher order modes of the general formula (m, n), where m and n are independently 1 or greater. Generally, the transducers will vibrate in higher order modes than (2,2). Higher order modes will produce more nodes and antinodes, result in three-dimensional standing waves in the water layer, characterized by strong gradients in the acoustic field in all directions, not only in the direction of the standing waves, but also in the lateral directions. As a consequence, the acoustic gradients result in stronger trapping forces in the lateral direction.

Generally, the ultrasonic transducer(s) may be driven by an electrical signal, which may be controlled based on voltage, current, phase angle, power, frequency or any other electrical signal characteristic. In particular, the driving signal for the transducer may be based on voltage, current, magnetism, electromagnetism, capacitive or any other type of signal to which the transducer is responsive. In embodiments, the signal driving the transducer can have a sinusoidal, square, sawtooth, pulsed, or triangle waveform; and have a frequency of 500 kHz to 10 MHz. The signal can be driven with pulse width modulation, which produces any desired waveform. The signal can also have amplitude or frequency modulation start/stop capability to eliminate streaming.

The transducers are used to create a pressure field that generates acoustic radiation forces of the same order of magnitude both orthogonal to the standing wave direction and in the standing wave direction. When the forces are roughly the same order of magnitude, particles of size 0.1 microns to 300 microns will be moved more effectively towards "trapping lines", so that the particles will not pass through the pressure field and continue to exit through the collection ports of the filtering device. Instead, the particles will remain within the acoustic chamber to be recycled back to the bioreactor.

In biological applications, some or all of the parts of the system (i.e., the bioreactor, acoustic filtering device, tubing fluidly connecting the same, etc.) can be separated from each other and be disposable. Avoiding centrifuges and filters can permit better separation of the CHO cells without lowering the viability of the cells. The transducers may also be driven to create rapid pressure changes to prevent or clear blockages due to agglomeration of CHO cells. The frequency of the transducers may also be varied to obtain optimal effectiveness for a given power.

The acoustic perfusion/filtering devices of the present disclosure can be used in a filter "train," in which multiple different filtration steps are used to clarify or purify an initial fluid/particle mixture to obtain the desired product and manage different materials from each filtration step. Each filtration step can be optimized to remove a particular material, improving the overall efficiency of the clarification process. An individual acoustophoretic device can operate as one or multiple filtration steps. For example, each individual ultrasonic transducer within a particular acoustophoretic device can be operated to trap materials within a given particle range. The acoustophoretic device can be used to remove large quantities of material, reducing the burden on subsequent downstream filtration steps/stages. Furthermore, additional filtration steps/stages can be placed upstream or downstream of the acoustophoretic device, such as physical filters or other filtration mechanisms, such as depth filters (e.g., polymeric morphology, matrix media adsorption), sterile filters, crossflow filters (e.g., hollow fiber filter cartridges), tangential flow filters (e.g., tangential flow filtration cassettes), adsorption columns, separation columns (e.g., chromatography columns), or centrifuges. Multiple acoustophoretic devices can be used as well. Desirable biomolecules or cells can be recovered/separated after such filtration/purification, as explained herein.

The outlets of the acoustophoretic separators/filtering devices of the present disclosure (e.g., product outlet, recycle outlet) can be fluidly connected to any other filtration step or filtration stage. Similarly, the inlets of the acoustophoretic separators/filtering devices of the present disclosure could also be fluidly connected to any other filtration step or filtration stage. The additional filtration steps/stages could be located either upstream (i.e., between the acoustophoretic separators(s) and the bioreactor), downstream, or both upstream and downstream of the acoustophoretic separators(s). In particular, it is to be understood that the acoustophoretic separators of the present disclosure can be used in a system with as few or as many filtration stages/steps located upstream or downstream thereof as is desired. The present systems can include a bioreactor, an acoustophoretic separator/filtering device, and multiple filtrations stages/steps located upstream and downstream of the acoustophoretic separator, with the filtrations stage(s) and acoustophoretic separator(s) generally serially arranged and fluidly connected to one another.

For example, when it is desired that the system include a filtration stage (e.g., a porous filter) located upstream of the acoustophoretic separator, the outlet of the bioreactor can lead to an inlet of the porous filter and the outlet of the porous filter can lead to an inlet of the acoustophoretic separator, with the porous filter pre-processing the fluid therein. As another example, when it is desired that the system include a filtration stage (e.g., a separation column) located downstream of the acoustophoretic separator, the outlet of the bioreactor can lead to an inlet of the acoustophoretic separator and the outlet of the acoustophoretic separator can lead to an inlet of the separation column, with the separation column further processing the fluid therein.

Filtration steps/stages can include or implement various methods such as an additional acoustophoretic separator/filtering device, or physical filtration, such as depth filtration, sterile filtration, size exclusion filtration, or tangential filtration. Depth filtration uses physical porous filtration mediums that can retain material through the entire depth of the filter. In sterile filtration, membrane filters with extremely small pore sizes are used to remove microorganisms and viruses, generally without heat or irradiation or exposure to chemicals. Size exclusion filtration separates materials by size and/or molecular weight using physical filters with pores of given size. In tangential filtration, the majority of fluid flow is across the surface of the filter, rather than into the filter.

Chromatography can also be used, including cationic chromatography columns, anionic chromatography columns, affinity chromatography columns, mixed bed chromatography columns. Other hydrophilic/hydrophobic processes can also be used for filtration purposes.

The techniques and implementations described herein may be used for integrated continuous automated bioprocessing. As a non-limiting example, CHO mAb processing may be carried out using the techniques and apparatuses described herein. Control can be distributed to some or all units involved in the bioprocessing. Feedback from units can be provided to permit overview of the bioprocess, which may be in the form of screen displays, control feedbacks, reporting, status reports and other information conveyance. Distributed processing permits a high degree of flexibility in achieving a desired process control, for example by coordinating steps among units and providing a batch executive control.

The bioprocessing can be achieved with commercially available components, and obtain 100% cell retention. Cell density can be controlled via an external cell bleed based on a capacitance signal. The perfusion device utilizing an acoustic wave system can be implemented with biocompatible materials, and may include gamma sterilized and single use components. The processing system also permits ultrasonic flow measurement, which is noninvasive, and is capable of operating with high viscosity fluids. The system can be implemented with single use sterile the septic connectors and a simple graphical user interface (GUI) for control.

The acoustic wave system includes a sweeping flow that is induced below the acoustic chamber. An acoustic standing wave can act as a barrier for particulates in the fluid to permit a clarified stream to be passed and extracted. The recirculation loop can be implemented with high fluid velocity and with a low shear rate. The fluid velocity through the acoustic field can be lower than the fluid velocity through the recirculation loop, which may help to improve separation with low shear forces.

Cell SE is dominated by harvest to recirculation flow ratio. Particle size distribution is shown in the figures, where a parent size-based separation occurs. The system passes fines and smaller cells in the harvest, e.g. Greater than 90% cell separation can be achieved, with 30% of the power and a 1.25% harvest to recirculation ratio with the disclosed system compared to previous systems. In addition, the acoustic wave system separation does not appear to affect quality between the bioreactor and the harvest. The quality is comparable between the acoustic wave system and tangential flow filtering. The acoustic wave system may have negligibly higher HMW species, and a similar charge of variance profile compared to a 0.22 μm membrane tangential flow filter.

The disclosed acoustic wave separator is a viable perfusion technology capable of supporting greater than 50 MVC/m L. The productivity of the acoustic wave be significantly improved, and the acoustic wave separator is scalable. For example, a relatively small unit is capable of operation at 2 L to 50 L scale. The perfusion device can be used with depth filtration or other upstream or downstream filtering or processing components, including chromatography.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the scope of the disclosure.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system. Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the scope of the disclosure. For example, the above elements may be components of a larger system, wherein other structures or processes may take precedence over or otherwise modify the application of the invention. Also, a number of operations may be undertaken before, during, or after the above elements are considered. Accordingly, the above description does not bound the scope of the claims.

The following examples are provided to illustrate the devices, components, and methods of the present disclosure. The examples are merely illustrative and are not intended to limit the disclosure to the materials, conditions, or process parameters set forth therein.

EXAMPLES

Example 1

Figure 16:
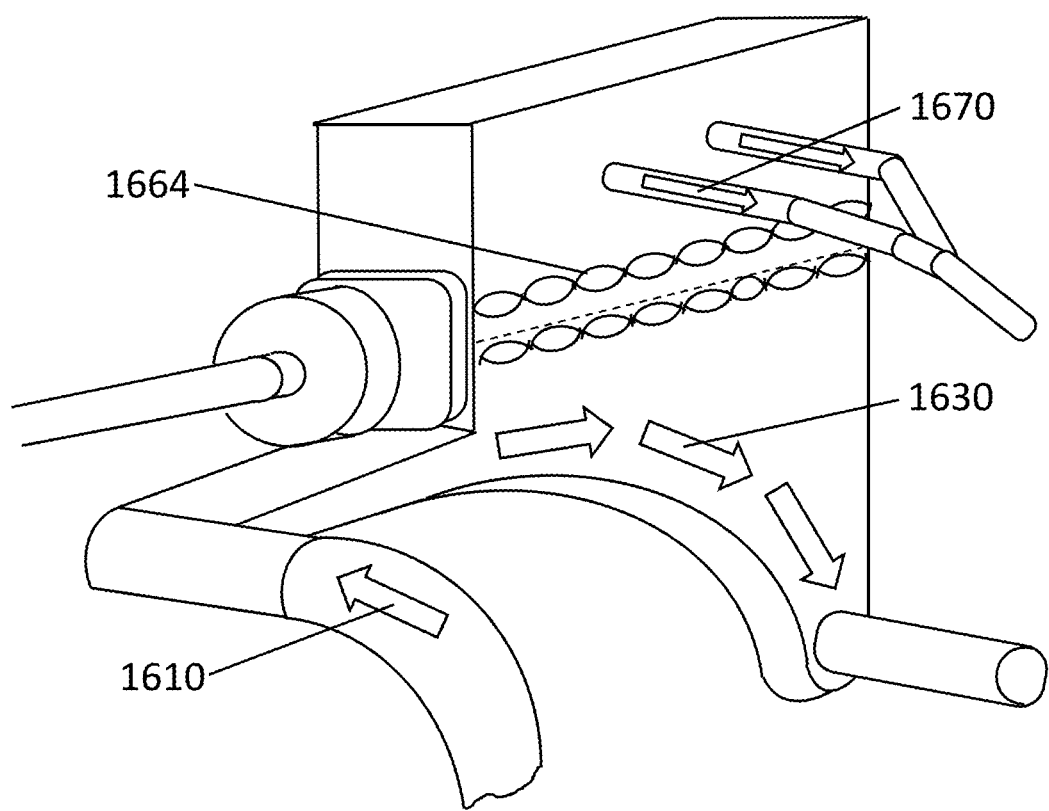
FIG. 16 is a view of an acoustic perfusion device, showing a reflector in the acoustic chamber between first and second transducers. The device is fluidly connected to an associated bioreactor. A fluid mixture is also present in the device and arrows are shown indicating the direction of flow in addition to waves indicating the acoustic field between the reflector and first and second transducers.

FIG. 16 is a picture of another acoustic perfusion device of the present disclosure, having two ultrasonic transducers and a concave bottom wall leading from the inlet port to the outlet port at the bottom end of the device. A cell containing fluid mixture is also present in the device. In this picture, acoustic standing waves are created in the collection zone between the reflector and first and second transducers as described above. The acoustic field generated thereby is indicated by waves and reference numeral 1664. The flow pattern of the fluid mixture through the device from the inlet port to the outlet port is shown with an arrow (reference numeral 1610) indicating the direction of fluid flow into the device and arrows (reference numeral 1630) indicating the direction of fluid flow through the device towards the outlet port. Finally, the general flow pattern of the desired product out of the device through the first and second collection ports is shown with arrows (reference numeral 1670) indicating the direction of flow.

Acoustophoretic separation has been tested using the acoustic perfusion device of FIG. 16 and the methods of separation of the present disclosure on different lines of Chinese hamster ovary (CHO) cells. FIGS. 20-28 show various test results varying different parameters and measuring different values using a Beckman Coulter Cell Viability Analyzer.

The perfusion flow rates with the acoustic filtering device were from about 2 mL/min to about 10 mL/min, or the flow rates were about 1 VVD to about 5 VVD for a 2.7 L working volume bioreactor. The VVD refers to the "vessel volume per day", or how many times the volume of the bioreactor vessel is cycled through the acoustic filtering device in one day. The perfusion flow rate (Qp) was collected through the perfusion ports. In contrast, the feed flow rates (Qf) were from about 40 mL/min to about 200 mL/min.

The feed solution had a starting CHO cell density of 50×10$^6$ cells/mL. The reactor size was 2.7 L and the feed volume of the host fluid was 1.5 L. In total, a series of seven tests (T1-T7) were performed to study the effect of varying the VVD and flow split in a 2.7 L volume reactor. The parameters for the tests are shown in Table 1 below.

TABLE 1

System results for a 2.7 L reactor and feed volume of 1.5 L

|  | Flow Split | Qp | | | |
|---|---|---|---|---|---|
|  | (Qp/Qf) | 1 VVD | 1.5 VVD | 2 VVD | 5.2 VVD |
| Qf | 5.0% | T1 | T2 | T3 | T7 |
|  | 2.5% | T4 | T5 | T6 |  |

The results included a cell clarification efficiency between 89-93% at a DC voltage of 45V, regardless of the flow rate. It is noted that the DC voltage for T1 was fixed at 60V, whereas for tests T2-T7 the DC voltage was reduced to a fixed amount of 45V. The transducer voltage amplitude is estimated to be about half of these values.

The results further included a perfusate turbidity reduction of 90-94% compared to the feed. The feed entered the inlet port, the recirculated fluid exited the outlet port and was recirculated, and the perfusate exited the perfusion port of the acoustic filtering device. It is noted that the turbidity measurements for tests T1 and T2 resulted in a hardware error, so only tests T3-T7 were used, which equated to a 6-10% turbidity in the perfusion stream relative to the feed stream, regardless of flow rate.

The tests revealed a cell viability for each flow rate that was within the error of instrument (i.e., ±6%), with the control ranging from 79-84% over all tests.

Further testing was performed using a solution designated "CHO Line A". The solution had a starting cell density of 50×10$^6$ cells/mL, a turbidity of 2,400 NTU, and cell viability of roughly 80%. The solution was separated using a device of the present disclosure in a system having a reactor size of 2.7 L. The volume of the feed fluid was between 1.5 L and 2.0 L. The perfused flow rates were from 2 mL/min to 10 mL/min, or from 1 to 5 VVD. A series of six tests were performed to study the effect of varying the VVD and flow split on acoustic filtration performance for the 2.7 L volume reactor. The parameters for the tests are shown in Table 2 below.

The bioreactor cell retention for the tests shows an approximately 90% perfusion efficiency. There was no significant change in measured cell viability across the tests.

Next, additional testing was performed using a solution designated "CHO Line B". The solution had a starting cell density of 75×10$^6$ cells/mL, a turbidity of 2,300 NTU, and cell viability of roughly 80%. The solution was separated using a device of the present disclosure in a system having a reactor size of 2.7 L. Four tests were performed (T1-T4). Two of the tests (T1, T3) used a device having a single transducer. The other two tests (T2, T4) used a device having two transducers in series (such that the fluid ran through both standing waves). The parameters for the tests are shown in Table 3 below.

TABLE 3

System results for a 2.7 L reactor and feed volume from 1.5 L-2.0 L

| T1 | | T2 | |
|---|---|---|---|
| Transducers | 1 | Transducers | 2 |
| VVD | 1 | VVD | 1 |
| Perfused Flow (mL/min) | 1.9 | Perfused Flow (mL/min) | 1.9 |
| Feed Flow (mL/min) | 75 | Feed Flow (mL/min) | 75 |
| T3 | | T4 | |
| Transducers | 1 | Transducers | 2 |
| VVD | 2 | VVD | 2 |
| Perfused Flow (mL/min) | 3.8 | Perfused Flow (mL/min) | 3.8 |
| Feed Flow (mL/min) | 150 | Feed Flow (mL/min) | 150 |

The bioreactor cell retention for the tests shows a perfusion efficiency greater than 90%. The results further evidenced an approximately 3-5% greater efficiency when using two transducers rather than a single transducer. There was no significant change in measured cell viability across the tests. Practically speaking, operating at low VVD offers a number of advantages, such as media cost reduction.

Example 2

Another experimental setup included an acoustic perfusion device similar to that illustrated in FIG. 5. Tubes are connected to the inlet port, outlet port, and the collection port.

The device was tested at a transducer voltage of 40V peak to peak, a perfused flow rate of 15-30 mL/min, and a recirculation flow rate of 2 L/min. Samples were taken every 45-60 minutes, and the cell retention rate was determined.

TABLE 2

System results for a 2.7 L reactor and feed volume from 1.5 L-2.0 L

| T1 | | T2 | | T3 | |
|---|---|---|---|---|---|
| VVD | 1.5 | VVD | 2 | VVD | 1 |
| Flow Split | 5.00% | Flow Split | 5.00% | Flow Split | 2.50% |
| Perfused Flow (ml/min) | 2.8 | Perfused Flow (ml/min) | 3.8 | Perfused Flow (ml/min) | 1.9 |
| Feed Flow (ml/min) | 56 | Feed Flow (ml/min) | 75 | Feed Flow (ml/min) | 75 |
| T4 | | T5 | | T6 | |
| VVD | 1.5 | VVD | 2 | VVD | 5.2 |
| Flow Split | 2.50% | Flow Split | 2.50% | Flow Split | 5.00% |
| Perfused Flow (ml/min) | 2.8 | Perfused Flow (ml/min) | 3.8 | Perfused Flow (ml/min) | 10 |
| Feed Flow (ml/min) | 112.5 | Feed Flow (ml/min) | 150 | Feed Flow (ml/min) | 194.2 |

The cell retention efficiency remained above 95% for perfused flow rates over about 12 mL/min and up to 20 mL/min, and remained above 90% up to about 25 mL/min.

Next, experiments were performed to determine what factors would affect cell retention. The perfused flow rate was varied, as was the transducer voltage. When the perfused flow rate was varied, the transducer voltage was maintained at 40V peak to peak and the recirculation flow rate was maintained at 2 L/min. When the transducer voltage was varied, the perfused flow rate was maintained at 20 mL/min and the recirculation flow rate was maintained at 2 L/min. The results indicated that, for this particular embodiment, a perfused flow rate of about 15 mL/min to about 28 mL/min was optimum, and a transducer voltage of about 15V peak to peak to about 28V peak to peak was optimum.

A computational fluid dynamics (CFD) model was made of this device. As expected, the highest velocities were found in the channel leading downwards from the inlet port to the outlet port. The velocity was near zero in the fluid cell and out through the collection port. This is important for two reasons: the acoustic field is more effective in a flow with a lower, more uniform velocity, and because the cells used in biomanufacturing are sensitive to flow, and the induced shear rate.

FIG. 17 is a diagram illustrating several aspects of this embodiment. Fluid flows into the device through the inlet port 710 (arrow 780) and into the acoustic chamber 790. The volume of fluid 750 below the acoustic chamber contains the tangential flow path, indicated by arrow 782. Fluid with a relatively high amount of viable cells will exit through the outlet port 730, as indicated by arrow 781. The acoustic interface effect/region created by the standing waves is marked with reference numeral 783, and is upstream of the acoustic standing wave field 784. The acoustic interface roughly coincides with an x-y plane in this diagram. This interface effect separates large cells from smaller cell fragments, particulate debris, desired biomolecules, etc., which can pass through the interface 783 and the acoustic standing wave field 784. By way of comparison, the cell aggregates that arise within the acoustic standing wave field 784 during the first mode of operation (see FIG. 41) can be described as being aligned in the y-z plane. In operation, the separation caused by the interface effect occurs at the interface region 783 as any large cells are held back by the "interface" or "barrier" effect. The harvest flow stream 785 containing the smaller fragments, particulate debris, desired biomolecules, etc. then exits through harvest port 770. The tangential flow path is part of the inlet flow path, and is located below the interface region 783 generated by the acoustic standing wave. The tangential flow path will transport away both the clusters of cells that drop from the acoustic standing wave field 784 due to gravity effects and the cells that are retained by the acoustic interface effect.

Example 3

Another way of explaining the operation of the acoustic perfusion device can be understood by looking at the results of a numerical study. In the numerical study, two fluids with differing effective acoustic properties (i.e., speed of sound and density), were modeled with an interface between them in COMSOL, a numerical simulation software. The acoustic field is calculated and therefrom the lateral radiation force acting on a particle in the direction of the fluid velocity is calculated using Gorkov's equation.

Figure 18:
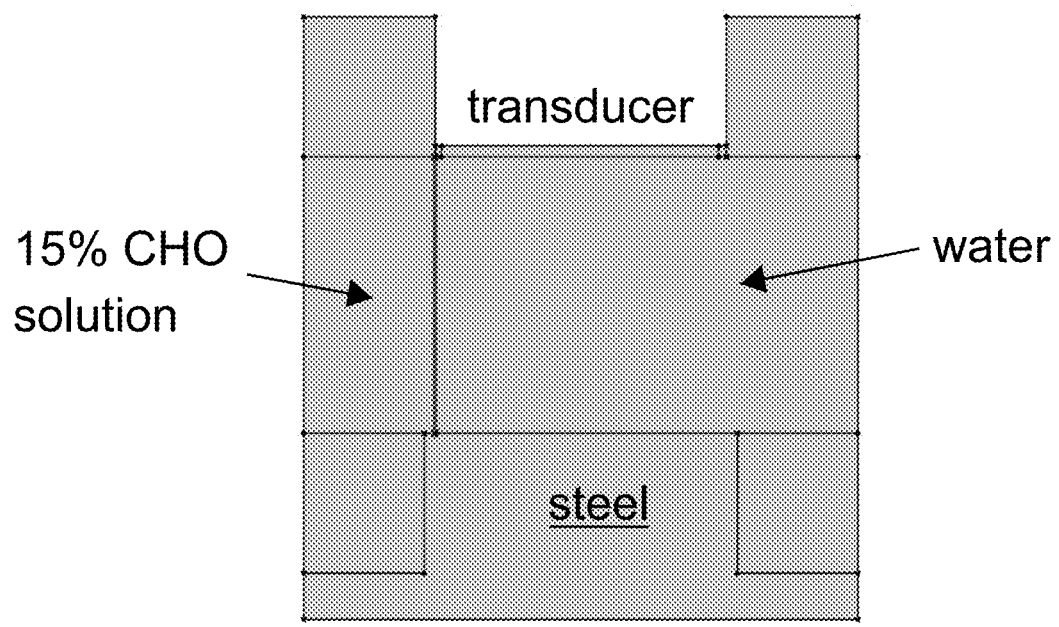
FIG. 18 shows the geometry of a model simulation of the acoustic device used for cell retention. The model contains two fluids, one a clarified fluid within the acoustic field, the other a high cell density fluid to the left of the acoustic field, a piezoelectric transducer, a steel reflector, and an aluminum housing. The first fluid was water within the acoustic field and the second fluid was a 15% concentration of CHO cells in water solution outside (to the left) of the acoustic field. The blue solid line in the model indicates the separation line between the two fluids.

FIG. 18 shows the geometry of the simulation, utilizing a piezoelectric transducer, steel reflector, aluminum housing, and two fluids: the first fluid being water within the acoustic field, simulating the clarified fluid, and the second fluid being a 15% concentration of CHO cells in water solution outside of the acoustic field, the second fluid having a higher density and higher speed of sound than the water fluid and simulating the bioreactor fluid containing the cells.

The two fluids were separated as indicated by the solid line in the model of FIG. 18. In this setup, the fluid velocity through the system was in a horizontal direction from left to right. In such a configuration, the acoustic field is implemented to obtain a retention device. The acoustic field generates a force on the cells that acts in the negative x-direction (i.e, opposite the fluid velocity). Water was modeled with a fluid density of 1000 kg/m$^3$ and a speed of sound of 1500 m/s. CHO cells were modeled having a density of 1050 kg/m$^3$ and a speed of sound of 1550 m/s. A coupled multi-physics numerical simulation that included a full piezoelectric simulation of the piezoelectric material, an acoustic simulation of the two fluids, and a linear elastic simulation in the steel and aluminum bodies was performed at various frequencies of excitation. The transducer was driven at a peak voltage of 40 V.

Figure 19A:
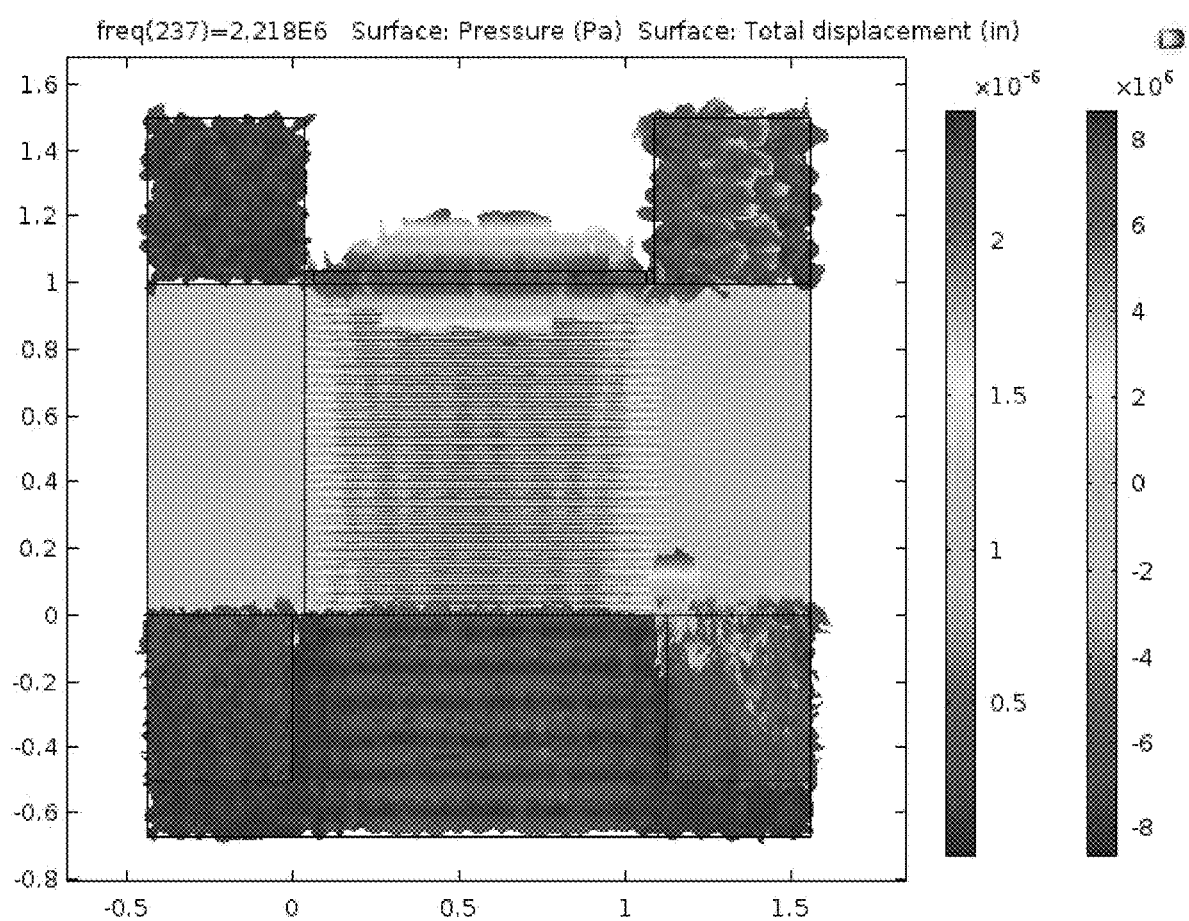
FIGS. 19A, 19B, and 19C are graphs showing the displacement of the piezoelectric material, the aluminum housing, and the steel reflector (left-side scale); and the acoustic pressure in the two fluids (right-side scale) of the model simulation of FIG. 18 at several frequencies of operation.
Figure 19B:
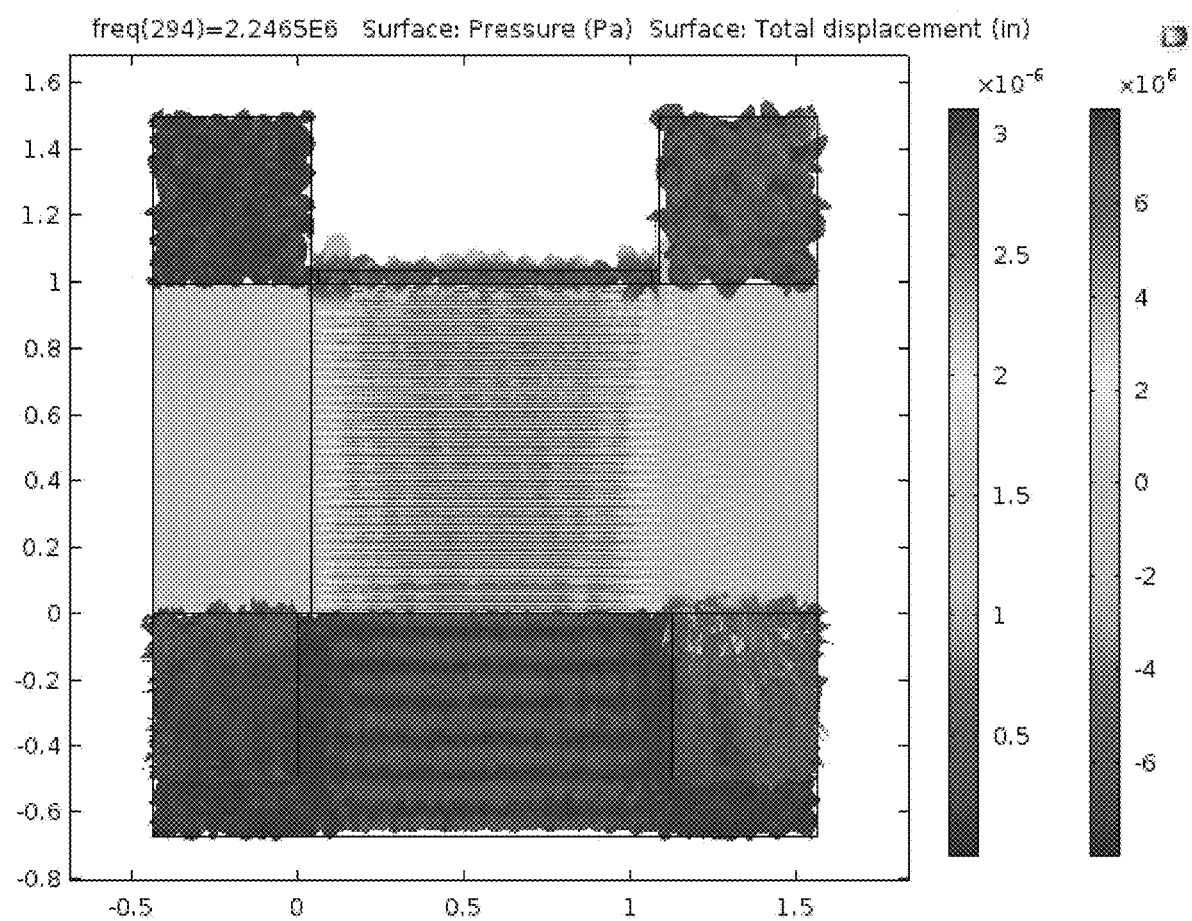
Figure 19C:
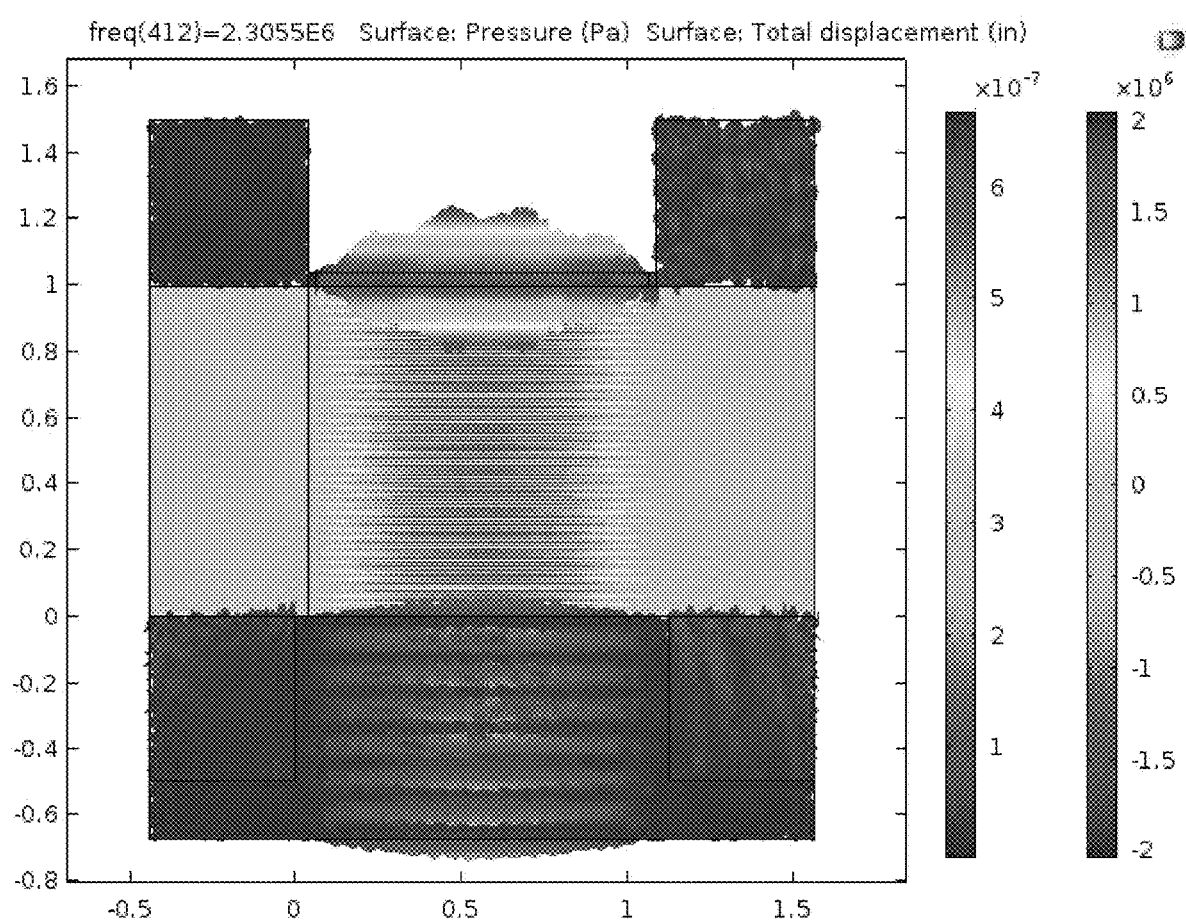

FIGS. 19A-19C show the acoustic pressure in the two fluids and the displacement of the piezoelectric material, the aluminum housing, and the steel reflector of the model at frequencies of operation of 2.218 MHz, 2.2465 MHz, and 2.3055 MHz. The lateral radiation force (i.e., horizontally in the direction of the fluid flow), was calculated at the interface between the two fluids along with real electrical power consumed by the transducer. The structural displacement of the transducer and steel are shown, along with the acoustic pressure in the fluid.

FIG. 20 shows the lateral radiation force (N) and the lateral radiation force normalized by power (N/W) versus frequency acting on the suspended CHO cells. This graph shows that at the resonance frequencies (i.e., local maxima in power), the average lateral radiation force on the interface is negative, meaning that it is in the negative-x direction. The result is the creation of an acoustic barrier effect or an acoustic interface effect. That is, the acoustic field at the interface between the two fluids exerts a strong lateral force on the suspended particles in a direction opposite to the fluid flow, thereby keeping the larger particles from entering the acoustic field and allowing only the first fluid (i.e., fluid containing only smaller particles, such as the desired product, and excluding whole cells) to enter the acoustic field, thereby creating an acoustic perfusion cell retention device. In this way, only the clarified fluid can escape and the cells are held back by the radiation force. This force is never positive, meaning that it always holds the cells back at the interface, not allowing them to cross the interface. The multiple peaks in the power curve show the existence of multiple modes of operation including planar resonance modes and multi-dimensional modes of operation, indicating that this type of operation can be generated through utilization of planar and multi-dimensional standing waves alike. In systems having 1"×1" dimensions, there exists a planar resonance about every 30 kHz. The graph shows evidence of additional peaks indicating the existence of the multi-dimensional modes. Per unit power, these modes can be equally or even more effective as the planar resonance modes. As explained above, the cells that are held back by the acoustic radiation force may then be picked up by the scrubbing motion of the flow field (i.e., the recirculating flow underneath the interface), and be continuously returned to the bioreactor to ensure they receive the nutrition and oxygen to maintain the production of the overall cell culture.

Example 4

Figure 21:
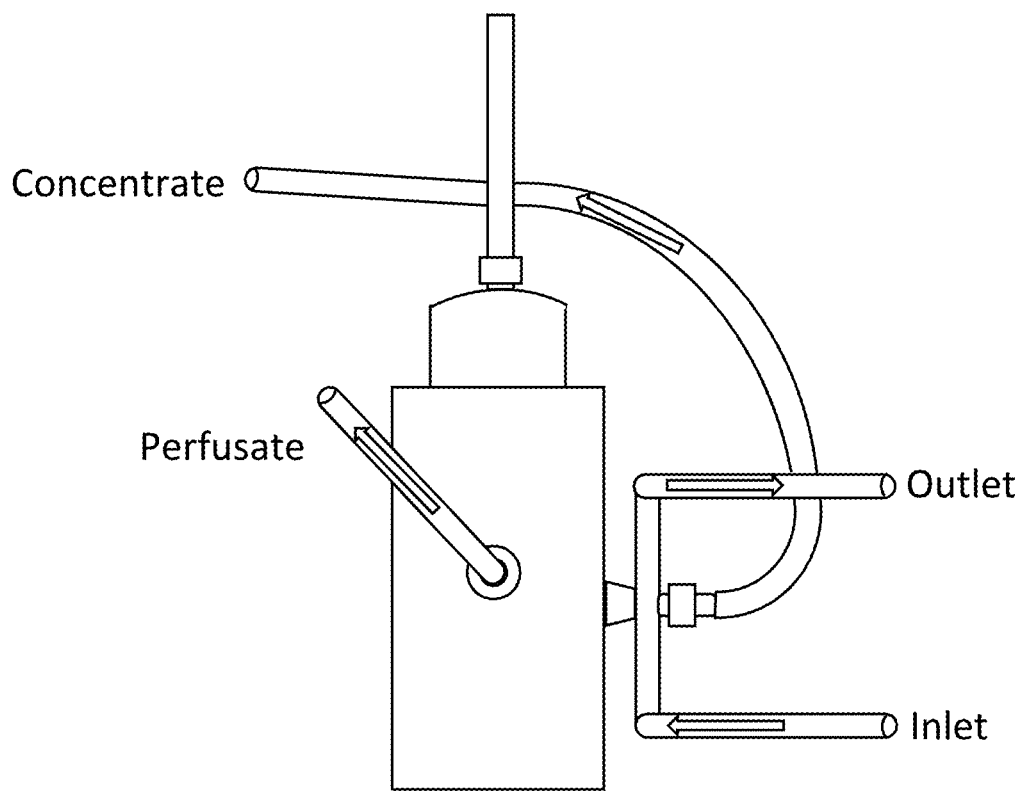
FIG. 21 is a picture (top view) of an acoustic perfusion device of the present disclosure. Arrows indicate the flow into the inlet port; the flow out of the outlet port; the clarified fluid flow out the top of the device and the flow of concentrate out the bottom of the device.
Figure 22:
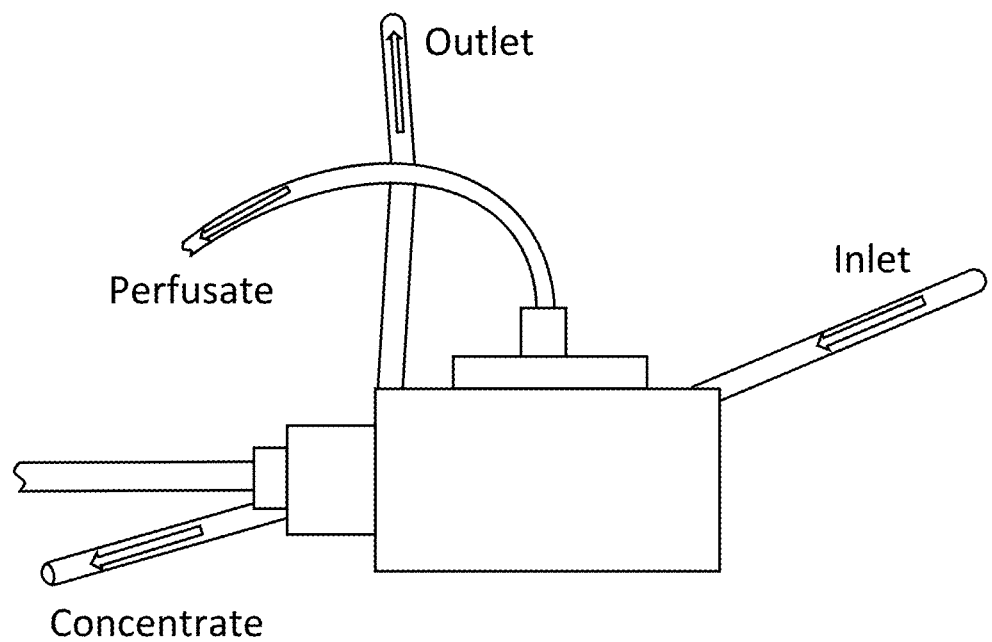
FIG. 22 is a picture (side view) of the acoustic perfusion device of FIG. 21.

FIG. 21 and FIG. 22 show another experimental setup for an acoustic perfusion device similar to that illustrated in FIG. 7. Tubes are connected to the inlet port, outlet port, the collection port, and the secondary outlet port (for a flow concentrated cells). Arrows are included to illustrate fluid flow. Arrows indicate the flow into the inlet port; the flow out of the outlet port; the perfusate flow out the top of the device and the flow of concentrate out the bottom of the device. The flow through the inlet port to the outlet port is the recirculation flowrate. The perfusate flow out the top of the device is the perfused flowrate containing clarified fluid depleted in cells and containing desired product. The flow of concentrate out the bottom of the device is the concentrated cell flow. The concentrated cell flow can be used for a cell bleed operation or if desired, the cells can be returned to the bioreactor.

Figure 23:
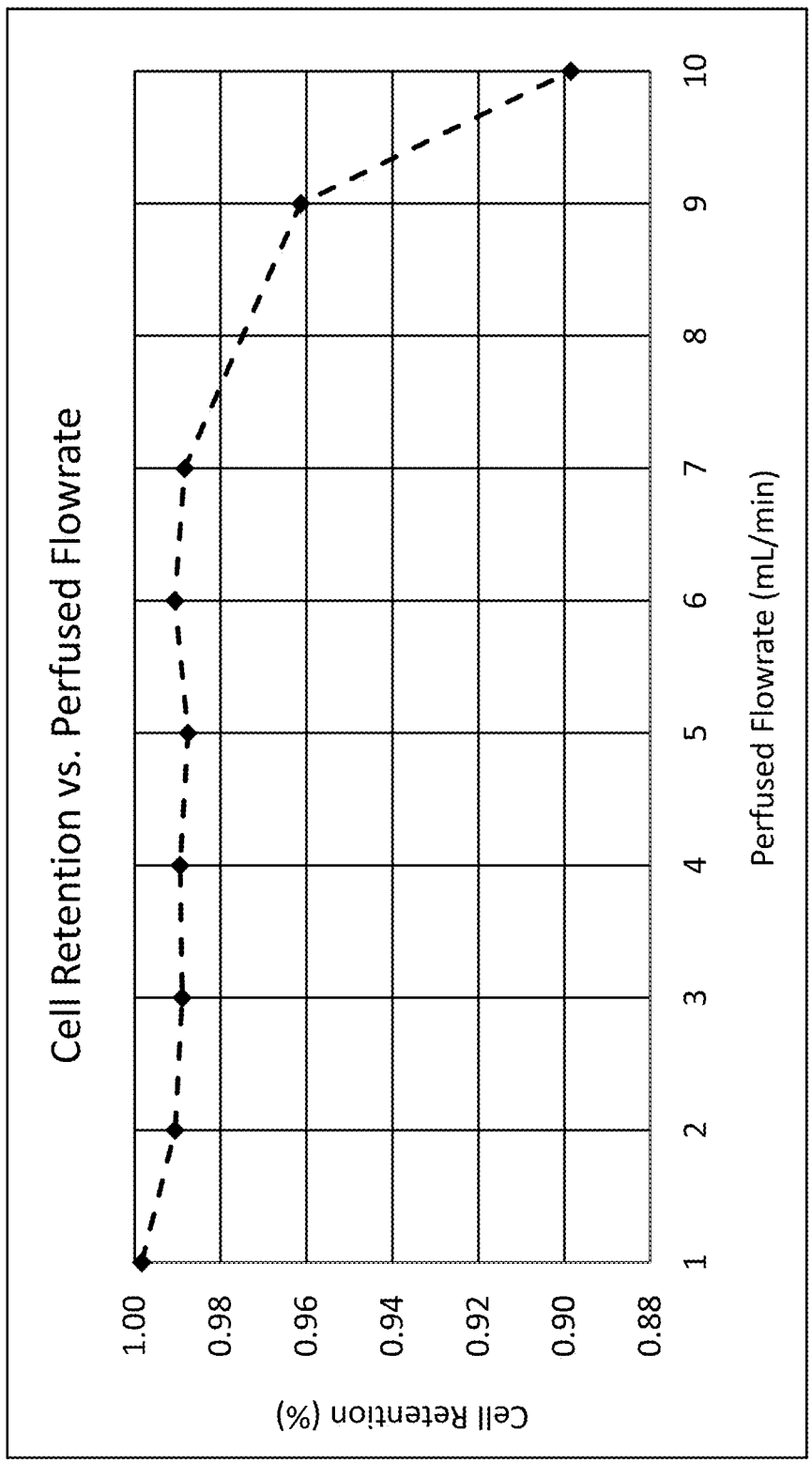
FIG. 23 is a graph of cell retention vs. perfusate flowrate for the device of FIG. 21.

The device was tested at a transducer voltage of 40V peak to peak, a perfused flow rate (out the top) of 1-10 mL/min, a recirculation flow rate of 0.75-1 L/min, and a concentrate flow rate (out the bottom) of 15 mL/min. The cell retention rate was determined for different perfused flowrates. FIG. 23 shows the results. The y-axis is the retention with 1.00 indicating 100% retention. The cell retention efficiency remained above 98% for perfused flow rates up to 7 mL/min, and was just below 90% at 10 mL/min.

Example 5

The device of FIG. 5 and FIG. 6 was tested at different flowrates (5 mL/min, 1.5 mL/min, 8 mL/min) on two different days. Higher values are more desirable, and most values were over 95% at flowrates ranging from 1.5 mL/min to 8 mL/min. The perfusate cell density (million cells/mL) versus time was also measured. Lower values are more desirable (indicating successful cell separation). As expected, results were better at lower flowrates.

Example 6

A computational fluid dynamics (CFD) model was made of the device with the internal structure of FIG. 26. As expected, the highest velocities were found in the inflow passageway into the acoustic chamber. The velocity is near zero in the acoustic chamber, and near the collection port at the top thereof. This is a desirable velocity profile.

Next, the device with the internal structure of FIG. 26 was tested at different flowrates (1.5 mL/min, 0.37 mL/min). Higher values are more desirable, and most values were over 97% at flowrates ranging from 0.37 mL/min to 1.5 mL/min. The perfusate cell density (million cells/mL) versus time was also measured. Here, lower values are more desirable (indicating successful cell separation). As expected, results were better at lower flowrates.

The device was then tested using two different operating frequencies for the ultrasonic transducer, 1 MHz or 2 MHz, and at different flowrates. The cell retention (%) versus time was measured. Higher values are more desirable. At 2 MHz, the values were close to 100% for flow rates of 1.5 mL/min to 3 mL/min. At 1 MHz, the values stayed over 90% for flow rates of 1.5 mL/min to 3 mL/min. The frequency of 2 MHz generally performed better. The perfusate cell density (million cells/mL) versus time was also measured. Again, results were better for 2 MHz operating frequency.

Example 7

A comparative evaluation between an AWS (acoustic wave separation) process according to the present disclosure and a TFF (tangential flow filtration) process (similar to that shown in FIG. 24) was performed using an acoustic perfusion device as described herein. FIGS. 28-39C include graphs illustrating this comparative evaluation for a variety of parameters. For both evaluations, a cell mixture was cultured in a bioreactor for 30 days. TFF or AWS was used for the separation of desired product from the cell culture, with the cells continuously returned to the bioreactor throughout the culture period. In the AWS process, the desired product was continuously obtained due to the nature of the AWS process. In both the TFF and AWS process, chromatography columns were used for further filtration/processing of the desired product downstream of the TFF/AWS process.

Figure 28:
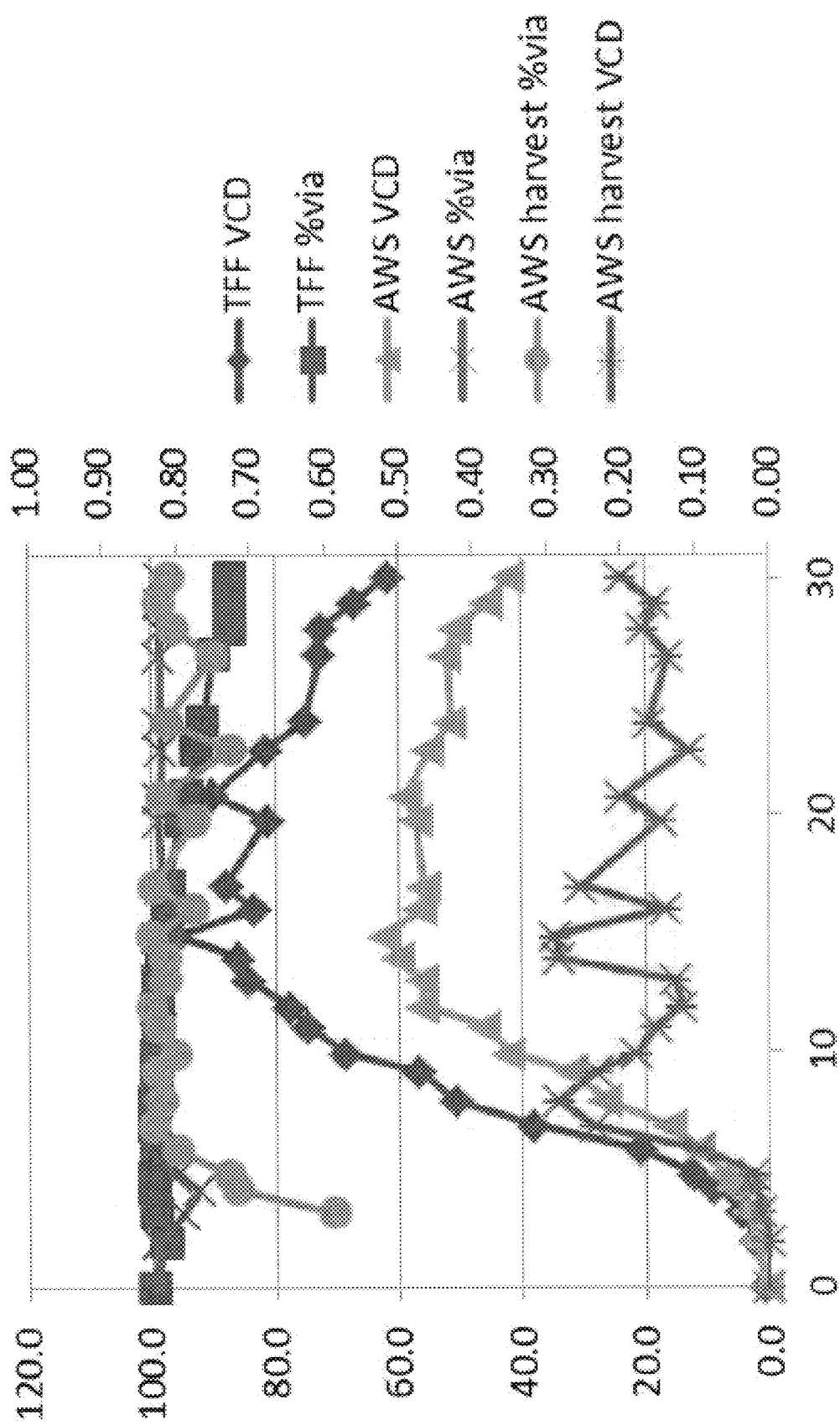
FIG. 28 is a graph of viable cell density versus time for both a tangential flow filtration (TFF) process and an acoustic wave separation (AWS) process according to the present disclosure. The left y-axis represents VCD in units of cells/mL and runs from 0 to 120 in intervals of 10. The right y-axis represents viability (% via) and runs from 0% to 100% in intervals of 10%. The x-axis represents time (in culture days) and runs from 0 to 30 days in intervals of 10.

FIG. 28 graphically illustrates the viable cell density (VCD) (expressed as cells/mL) and viability (expressed as a percentage) versus time for both a tangential flow filtration (TFF) process and an acoustic wave separation (AWS) process according to the present disclosure. In FIG. 28, the line having diamond-shaped data points represents the VCD of the TFF process; the line having square-shaped data points represents the viability of the TFF process in the bioreactor; the line having triangle-shaped data points represents the VCD of the AWS process; the line having x-shaped data points represents the viability of the AWS process in the bioreactor; the line having circular-shaped data points represents the viability of the AWS process in the harvest stream (i.e., after acoustic wave separation); and the line having *-shaped data points represents the viability of the TFF process in the permeate stream (i.e., after tangential flow filtration). As can be seen in FIG. 28, the harvest % viability was near 100% after day 8, and generally remained at this high level.

Figure 29:
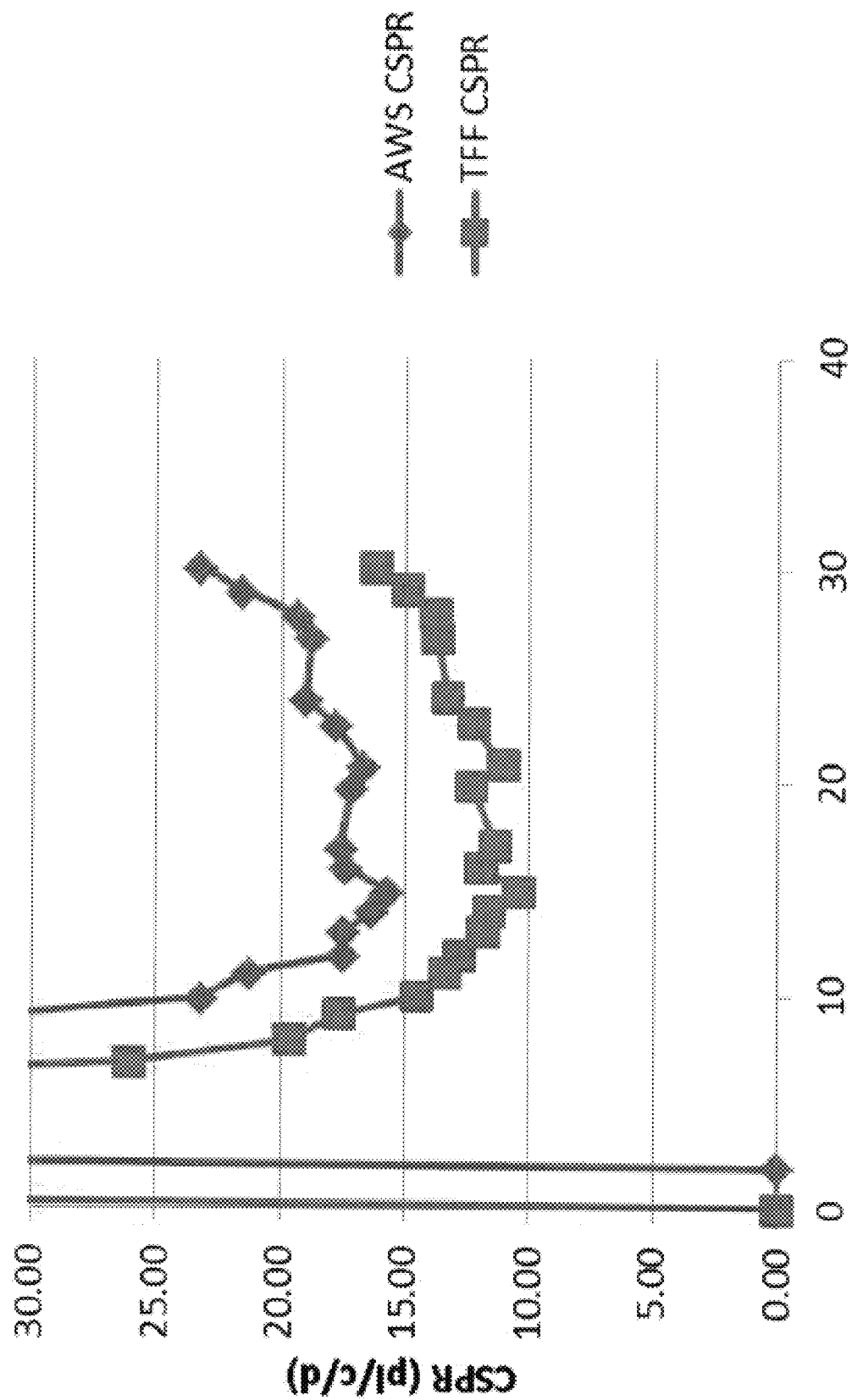
FIG. 29 is a graph of cell specific perfusion rate (CSPR) versus time for both a TFF process and an AWS process according to the present disclosure. The y-axis represents CSPR in units of pico liters per cell per day (pl/c/d) and runs from 0 to 30 in intervals of 5. The x-axis represents time (in culture days) and runs from 0 to 40 days in intervals of 10.

FIG. 29 graphically illustrates the cell specific perfusion rate (CSPR) (expressed as picoliters per cell per day) for both a TFF process and an AWS process according to the present disclosure. In FIG. 29, the line having diamond-shaped data points represents the CSPR of the AWS process, and the line having square-shaped data points represents the CSPR of the TFF process. The offset between the lines is due to differences in the cell densities for each process. Even with this offset, it can be seen that the AWS CSPR is improved over the TFF CSPR.

Figure 30:
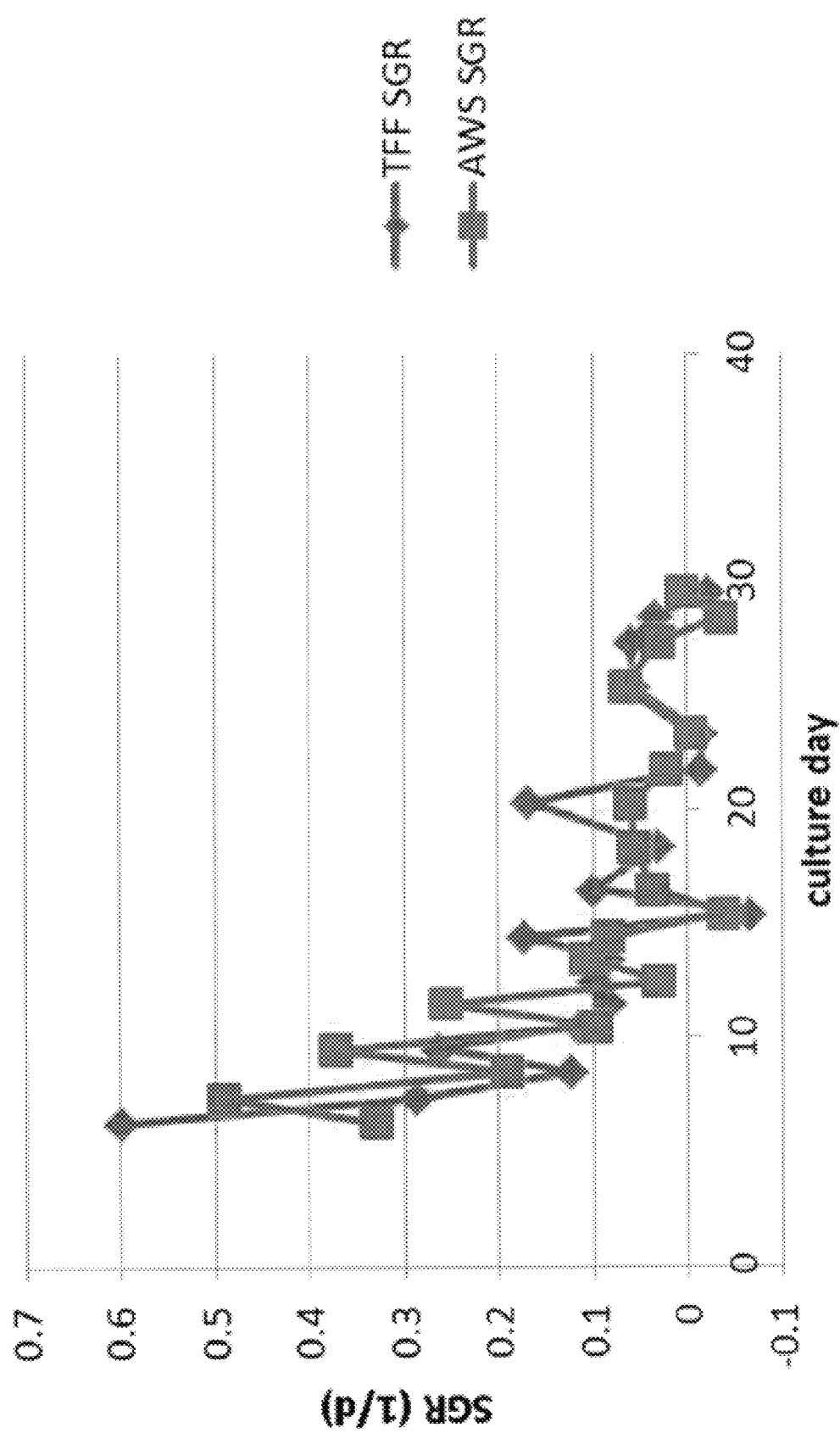
FIG. 30 is a graph of specific growth rate (SGR) in the bioreactor versus time for both a TFF process and an AWS process according to the present disclosure. The y-axis represents SGR in units of 1/day, and runs from −10% to 70% in intervals of 10%. The x-axis represents time (in culture days) and runs from 0 to 40 days in intervals of 10.

FIG. 30 graphically illustrates the specific growth rate (SGR) (per day) in the bioreactor versus time for both a TFF process and an AWS process according to the present disclosure. In FIG. 30, the line having diamond-shaped data points represents the SGR of the TFF process, and the line having square-shaped data points represents the SGR of the AWS process. The specific growth rate accounts for both death and harvest losses. As can be seen in FIG. 30, there is no significant difference between the TFF and AWS processes, which indicates that AWS is a suitable addition to or substitution for TFF in conventional processes.

Figure 31:
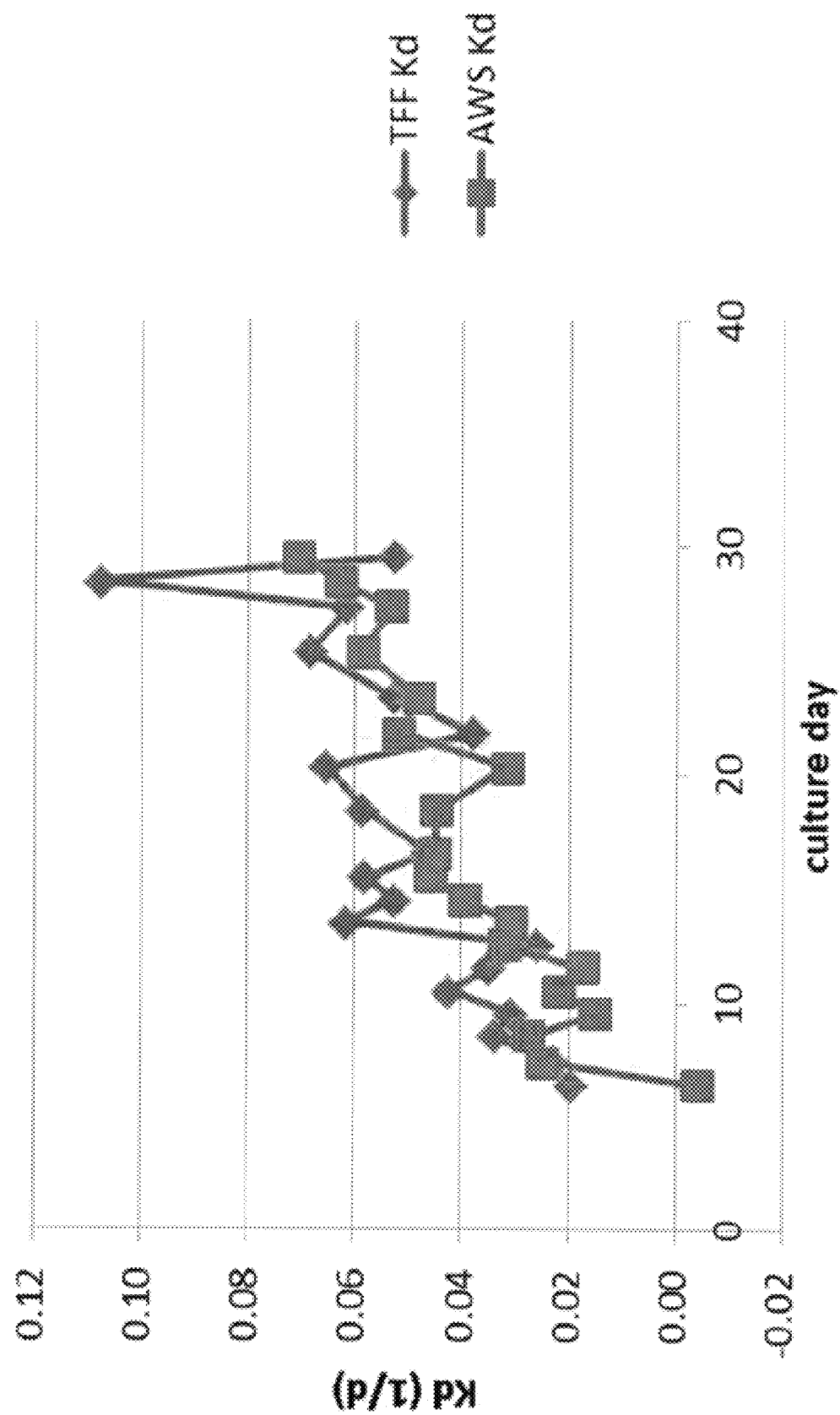
FIG. 31 is a graph of specific death rate (Kd) in the bioreactor versus time for both a TFF process and an AWS process according to the present disclosure. The y-axis represents Kd in units of 1/day, and runs from −2% to 12% in intervals of 2%. The x-axis represents time (in culture days) and runs from 0 to 40 days in intervals of 10.

FIG. 31 graphically illustrates the specific death rate (Kd) (per day) in the bioreactor versus time for both a TFF process and an AWS process according to the present disclosure. In FIG. 31, the line having diamond-shaped data points represents the Kd of the TFF process, and the line having square-shaped data points represents the Kd of the AWS process. As can be seen in FIG. 31, there is no significant difference between the TFF and AWS processes, again indicating that AWS is a suitable addition to or substitution for TFF in conventional processes.

Figure 32:
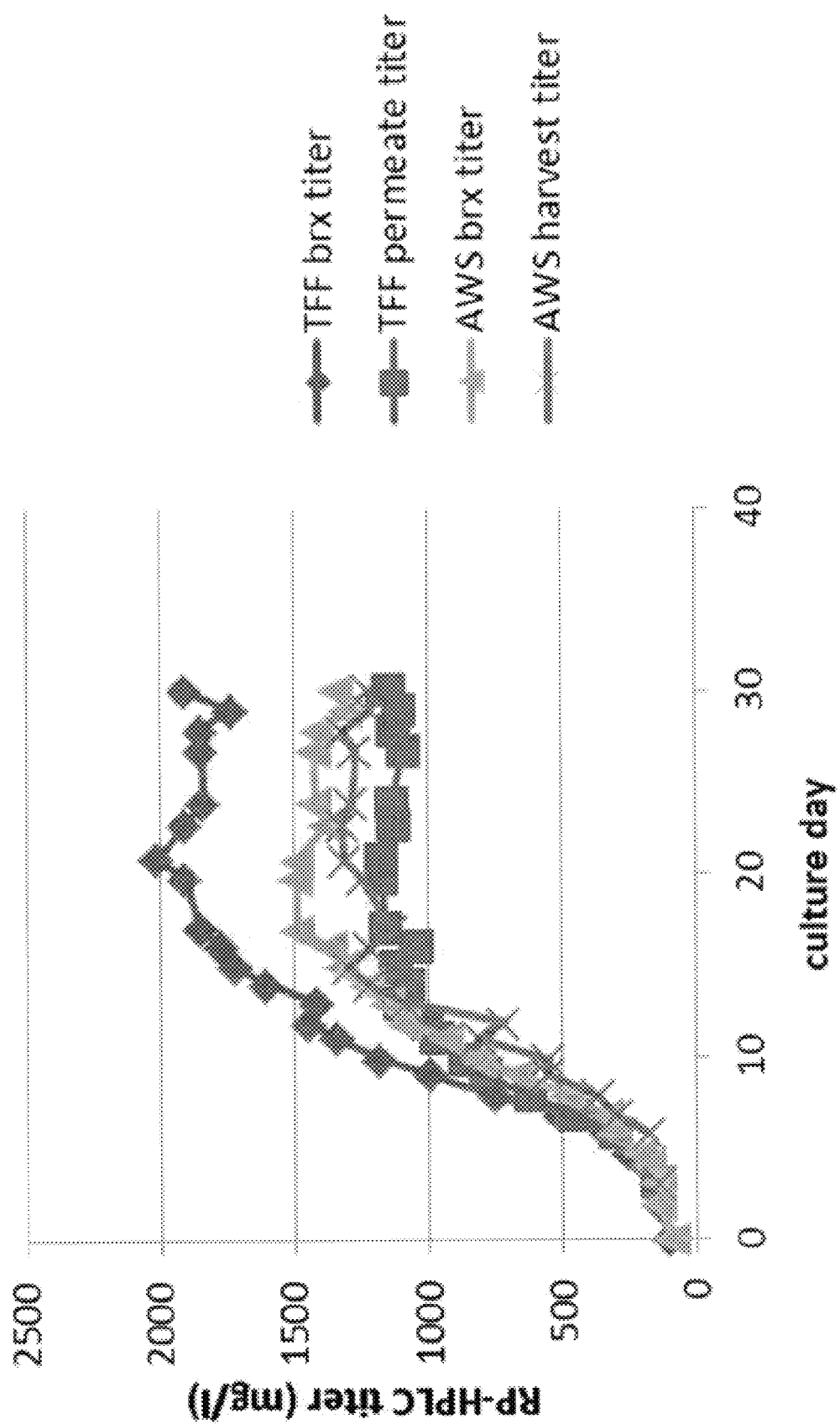
FIG. 32 is a graph illustrating titer in the bioreactor (BRX) versus in the permeate or harvest stream for TFF and AWS. The y-axis represents the reversed-phase high-performance liquid chromatography (RP-HPLC) titers (expressed in mg/L) and runs from 0 to 2500 in intervals of 500. The x-axis represents time (in culture days) and runs from 0 to 40 days in intervals of 10.

FIG. 32 graphically illustrates the titer (i.e., the concentration of protein available) in the bioreactor (BRX) for both a TFF process and an AWS process according to the present disclosure versus in the permeate (TFF) and harvest (AWS) streams of each process. In FIG. 32, the line having diamond-shaped data points represents the titer of the TFF process in the bioreactor; the line having square-shaped data points represents the titer of the TFF process in the permeate stream (i.e., after tangential flow filtration); the line having triangle-shaped data points represents the titer of the AWS process in the bioreactor; and the line having x-shaped data points represents the titer of the AWS process in the harvest stream (i.e., after acoustic wave separation). The large difference between the TFF permeate titer and the TFF bioreactor titer indicates that a low amount of the potential protein that could be harvested is actually harvested in the TFF process. In comparison, the relatively small offset between the AWS harvest titer and the AWS bioreactor titer is consistent with almost 100% efficiency in harvesting of the protein. In this way, FIG. 32 suggests that AWS is advantageous over TFF for capturing the desired protein and separating it from the bioreactor.

Figure 33:
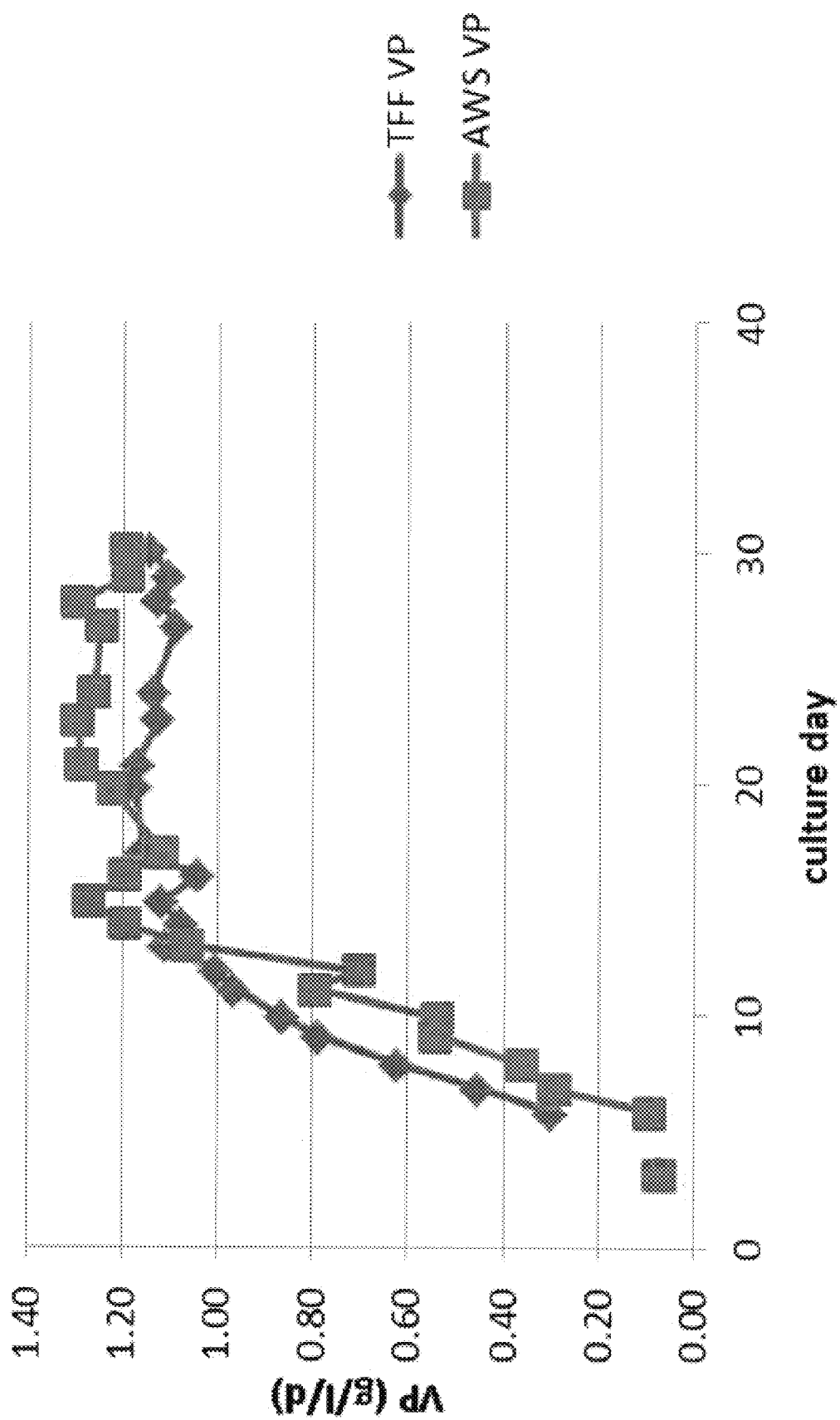
FIG. 33 is a graph of volumetric productivity (VP) versus time for both a TFF process and an AWS process according to the present disclosure. The y-axis represents VP in units of grams/liter/day, and runs from 0 to 1.4 in intervals of 0.2. The x-axis represents time (in culture days) and runs from 0 to 40 days in intervals of 10.

FIG. 33 graphically illustrates the volumetric productivity (VP) (expressed in grams/L/day) (i.e., the amount of protein produced per day) for both a TFF process and an AWS process according to the present disclosure. In FIG. 33, the line having diamond-shaped data points represents the VP of the TFF process, and the line having square-shaped data points represents the VP of the AWS process. As can be seen in FIG. 33, there is again no significant difference between the TFF and AWS processes, yet again indicating that AWS is a suitable addition to or substitution for TFF in conventional processes.

Figure 34:
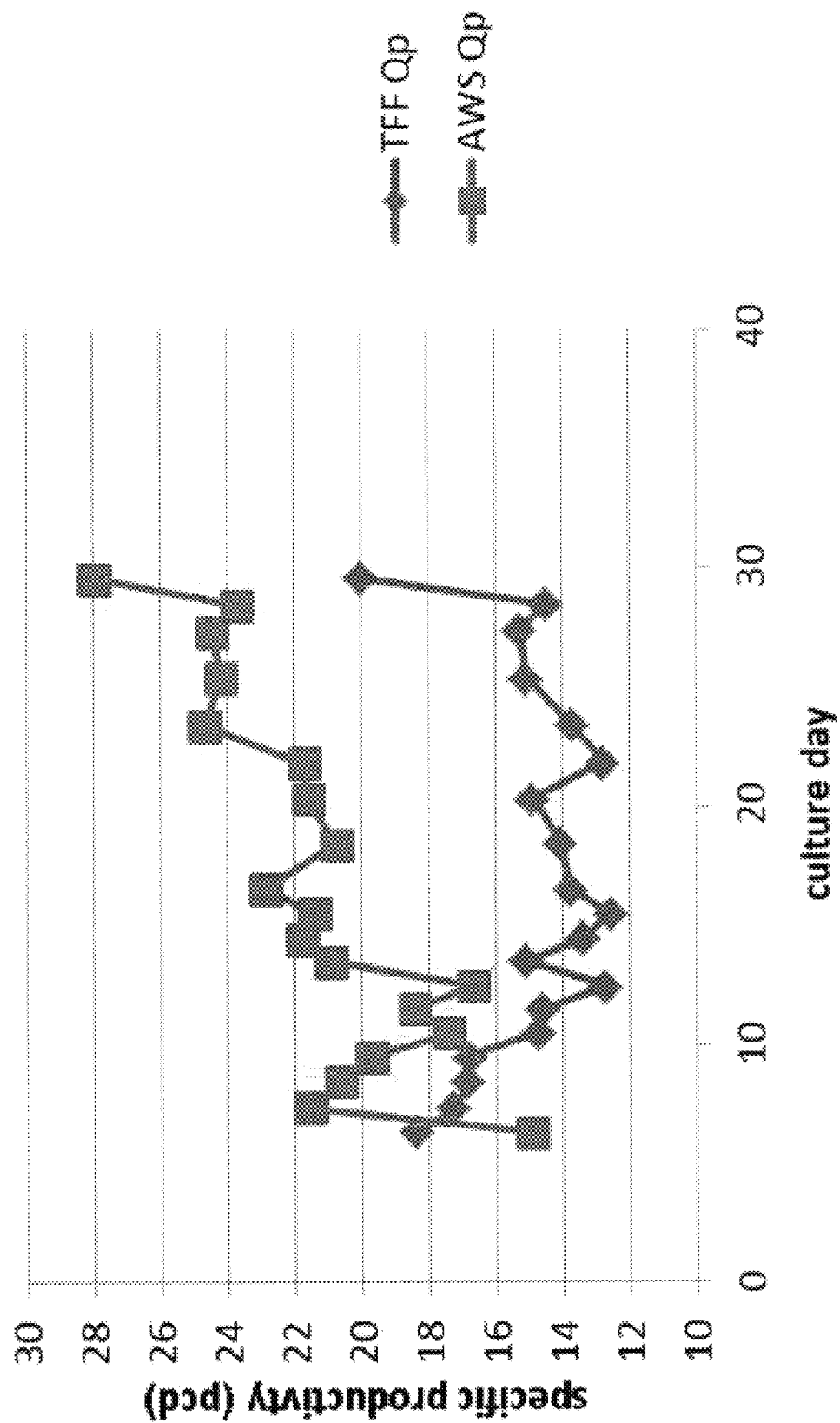
FIG. 34 is a graph of specific productivity (Qp) versus time for both a TFF process and an AWS process according to the present disclosure. The y-axis represents Qp in units of pcd (protein/cell/day), and runs from 10 to 30 in intervals of 2. The x-axis represents time (in culture days) and runs from 0 to 40 days in intervals of 10.

FIG. 34 graphically illustrates the specific productivity (Qp) (expressed in pico grams protein/cell/day) (i.e., the amount of product created by each cell in the bioreactor per day) for both a TFF process and an AWS process according to the present disclosure. In FIG. 34, the line having diamond-shaped data points represents the Qp of the TFF process, and the line having square-shaped data points represents the Qp of the AWS process. As can be seen in FIG. 34, the specific productivity of the AWS process is significantly greater than that for the TFF process, e.g. by thirty percent or more at different days in the culture process. The productivity increase with the AWS process is due to the selection of larger, more productive cells that are returned to the bioreactor. Over time, the cells in the bioreactor of the AWS process are thus selected to be more productive. The increase in productivity is believed to be due to the AWS process effectively selecting the cells that produce more protein. The selection of the more productive cells through the perfusion process tends to change the population of cells in the bioreactor over time, such that cells with greater ribosomal content, or larger cells, are retained over time, while nonproductive cells or lower productive cells are culled out of the system. In addition, or alternatively, cells that are in the process of mitosis, or reproduction, tend to be larger as well as more productive producers of biomolecules. Such cells tend to have greater ribosomal content as well. These cells are selected by the AWS process for return to the bioreactor, leading to a trend of cells that tend to be larger in the bioreactor population. Accordingly, over time, the AWS process tends to make the cells more productive, especially when compared to the TFF process, which does not posses these advantages, as illustrated in FIG. 34.

FIGS. 35A-35D graphically illustrate nutrient uptake markers for metabolism for both a TFF process and an AWS process according to the present disclosure versus time. In each graph, the line having diamond-shaped data points represents the AWS process, and the line having square-shaped data points represents the TFF process. As can be seen in FIGS. 35A-35D, there is no significant difference between the TFF and AWS processes, indicating that AWS is a suitable addition to or substitution for TFF in conventional processes.

FIGS. 36A-36C graphically illustrate ion exchange chromatography (IEX) results of charge variants for both a TFF process and an AWS process according to the present disclosure versus time. In FIGS. 36A-36C, the line having diamond-shaped data points represents the AWS process, and the line having square-shaped data points represents the TFF process. It is noted that while there was some increase in the basic variant (FIG. 36B), this increase is believed to have been caused by a discrepancy in the media used between the tests. Otherwise, there is no significant difference between the TFF and AWS processes as provided in FIGS. 36A-36C.

Figure 37A:
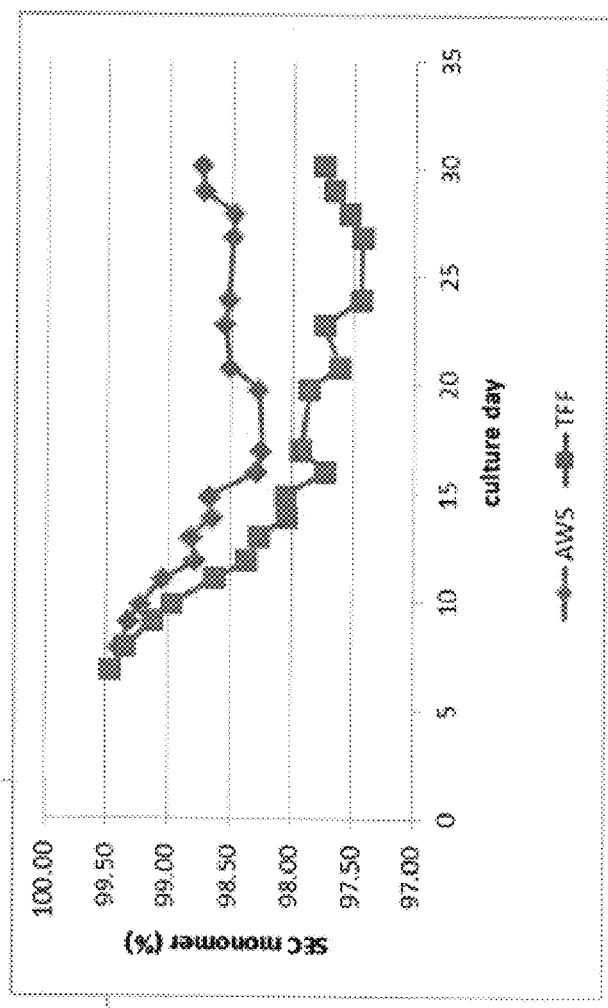
FIGS. 37A-37B illustrate two graphs of size exclusion chromatography (SEC) results for both a TFF process and an AWS process according to the present disclosure versus time. The x-axis of both graphs represents time (in culture days) and runs from 0 to 35 days in intervals of 5. The y-axis of FIG. 37A represents SEC HMW (high molecular weight) species (percentage) and runs from 0 to 3 in intervals of 0.5. The y-axis of FIG. 37B represents SEC monomer (percentage) and runs from 97 to 100 in intervals of 0.5.
Figure 37B:
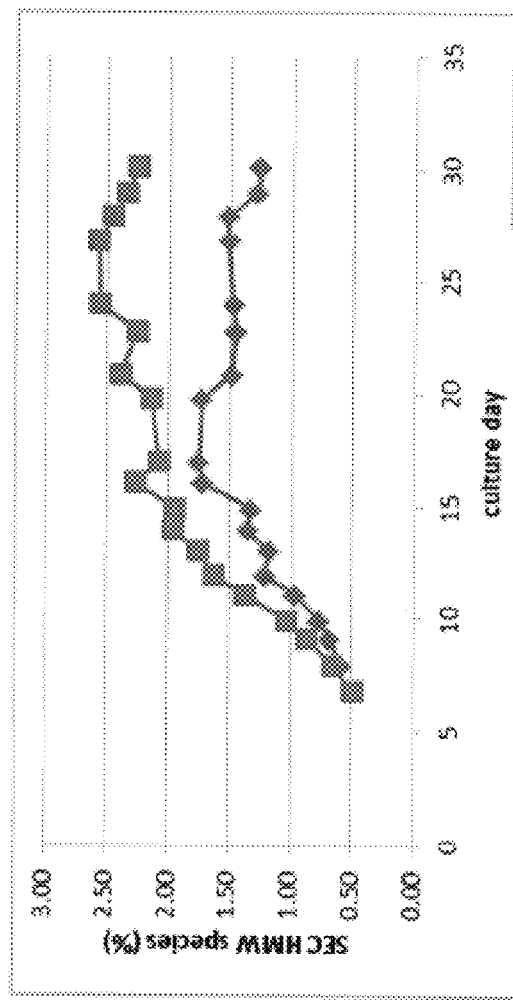

FIGS. 37A-37B graphically illustrate size exclusion chromatography (SEC) results for both a TFF process and an AWS process according to the present disclosure versus time. In FIGS. 37A-37B, the line having diamond-shaped data points represents the AWS process, and the line having square-shaped data points represents the TFF process. A decrease in HMW species is observed in FIG. 37A, and an increase in the monomer percent is observed in FIG. 37B for the AWS process versus the TFF process. Undesirable protein aggregation during monoclonal antibody production is known to occur in upstream and downstream processing, which is a major concern for therapeutic applications where aggregates influence drug performance and safety. These graphs suggest that the AWS process is efficient at separating out the protein aggregates in the system. The reduction in the amount of protein aggregates helps to lessen the burden on downstream filtration processes that could otherwise be overly subject to fouling and clogging due to the large aggregates. Moreover, protein aggregates are typically nonfunctional and are a problem for the efficacy of therapeutic drugs, which makes their removal even more desirable.

Figure 38A:
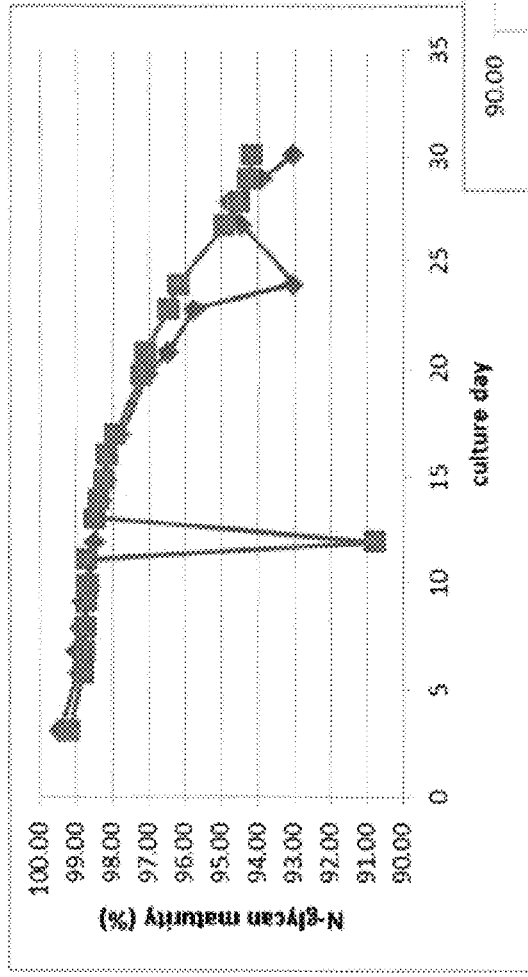
FIGS. 38A-38B illustrate two graphs of glycosylation (N-glycan) results for both a TFF process and an AWS process according to the present disclosure versus time. The x-axis of both graphs represents time (in culture days) and runs from 0 to 35 days in intervals of 5. The y-axis of FIG. 38A represents N-glycan maturity (percentage) and runs from 90 to 100 in intervals of 1. The y-axis of FIG. 38B represents primary form (percentage of G0F glycoforms) and runs from 50 to 90 in intervals of 5.
Figure 38B:
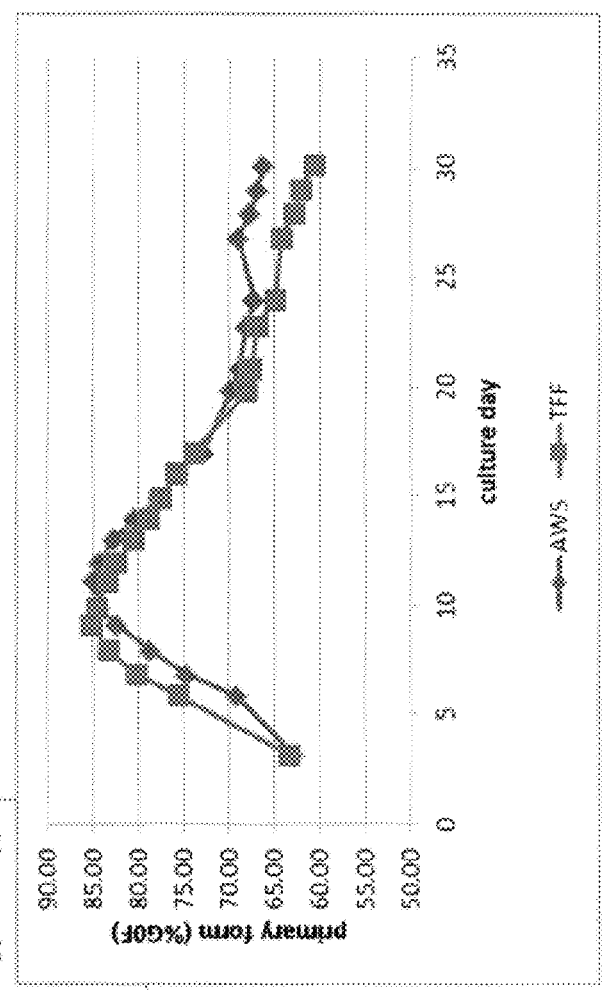

FIGS. 38A-38B graphically illustrate glycosylation (N-glycan) results for both a TFF process and an AWS process according to the present disclosure versus time. In each graph, the line having diamond-shaped data points represents the AWS process, and the line having square-shaped data points represents the TFF process. As can be seen from these two graphs, there is no significant difference between the TFF and AWS processes, once again indicating that AWS is a suitable addition to or substitution for TFF in conventional processes. This process refers particularly to the enzymatic process in which glycans are attached to the proteins of the biomolecules. Antibody glycosylation is a common post-translational modification and has a critical role in antibody effector function. The biomolecules (e.g., antibodies) of the present disclosure can be glycoengineered to product antibodies with specific glycoforms. For example, specific glycoforms may be desired to achieve desired therapeutic effects, and glycoengineering can be used to achieve the same.

FIGS. 39A-39C graphically illustrate additional glycosylation (N-glycan) results for both a TFF process and an AWS process according to the present disclosure versus time. In each graph, the line having diamond-shaped data points represents the AWS process, and the line having square-shaped data points represents the TFF process. The majority of approved monoclonal antibodies have two N-linked biantennary complex-type oligosaccharides bound to the Fc region, making them of the IgG1 isotype type. The Fc region is important in that it exercises the effector function of the antibody-dependent cell-mediated cytotoxicity (ADCC) through its interaction with leukocyte receptors of the FcγR family. ADCC is important in the efficacy of cancer antibodies, but with many approved cancer antibodies there is less ADCC that could be desired due to nonspecific IgG competing with the drugs for binding to FcγIIIa on natural killer cells. As can be seen in FIG. 39B, the afucosylation percentage is decreased in the AWS process versus the TFF process.

Antibody glycosylation can be affected by the composition of growth and feed media, including the concentration of ammonia, glutamine, glucose, and metal ions. As a result, it is critical during media development and optimization to monitor and consider a culture medium's impact on glycosylation. For therapeutic antibodies whose mechanism of action includes antibody-dependent, cell-mediated cytotoxicity (ADCC), it is particularly important to measure N-glycan fucosylation, because the same is known to have a strong influence on ADCC activity. A decrease in fucosylation increases the antibodies' binding affinity on natural killer cells and ultimately increases ADCC potency (which has been identified as a crucial mechanism of anti-cancer therapeutic antibodies). Thus, there exists significant interest in lowering fucosylation to increase therapeutic antibody efficacy. Compared to fucosylated IgGs, these non-fucosylated forms have a much increased ADCC without any detectable chance in CDC or antigen binding capability.

Figure 40:
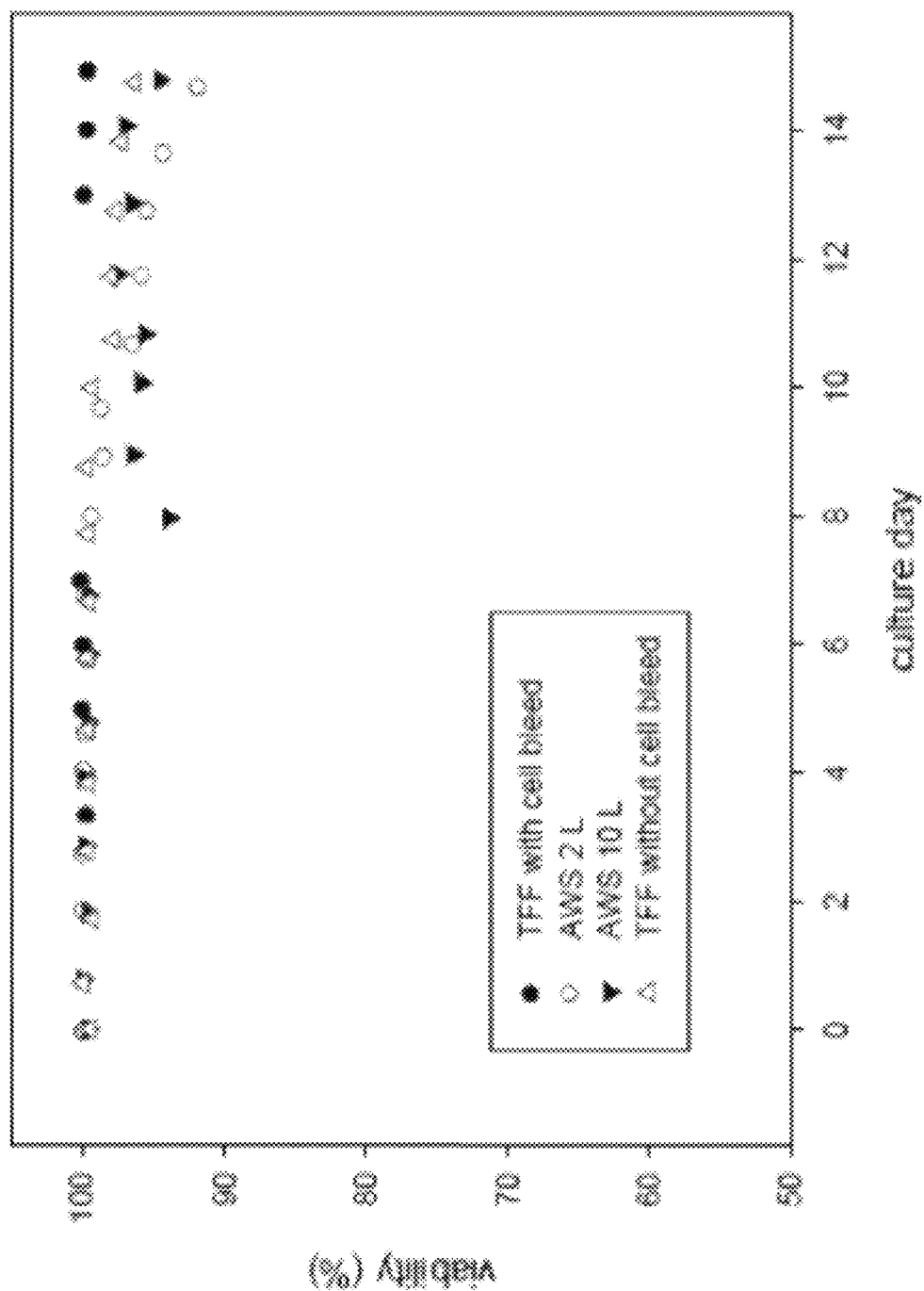
FIG. 40 is a graph of cell viability over time. The y-axis is cell viability in % of original cell count, and runs from 50% to 100% in intervals of 10%. The x-axis is culture days, and runs from 0 to 14 days in intervals of 1. Dark circles are for a TFF process with cell bleed. White circles are for an AWS process using a 2 L flow chamber. Dark inverted triangles are for an AWS process using a 10 L flow chamber. White triangles are for a TFF process without cell bleed.

FIG. 40 is a graph of cell viability over time. Dark circles are for a TFF process with cell bleed. White circles are for an AWS process using a 2 L flow chamber. Dark inverted triangles are for an AWS process using a 10 L flow chamber. White triangles are for a TFF process without cell bleed. As seen here, the AWS processes still maintain well over 90% viability after 14 days.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A process for separating biomolecules from a fluid mixture, the process comprising:
 flowing a fluid mixture containing biomolecules and cells through an acoustic perfusion device, the acoustic perfusion device comprising:
  an acoustic chamber that receives the fluid mixture containing the biomolecules and cells; and
  an ultrasonic transducer that includes a piezoelectric material that can be excited to generate a multi-dimensional acoustic standing wave in the acoustic chamber;
 exciting the ultrasonic transducer to create the multi-dimensional acoustic standing wave; and
 retaining cells with a larger size in the fluid mixture with the multi-dimensional acoustic standing wave.

2. The process of claim 1, wherein the cells with a larger size are trapped by the multi-dimensional acoustic standing wave and the biomolecules pass through the multi-dimensional acoustic standing wave.

3. The process of claim 2, wherein the trapped cells are recycled to a bioreactor upstream of the acoustic perfusion device.

4. The process of claim 1, wherein the biomolecules are therapeutic antibodies.

5. The process of claim 4, wherein a fucosylation of the therapeutic antibodies is increased and the efficacy of the therapeutic antibodies is changed.

6. The process of claim 1, wherein the biomolecules are produced by culturing cells in a bioreactor prior to flowing the fluid mixture through the acoustic perfusion device.

7. The process of claim 1, wherein a pressure rise and an acoustic radiation force on cells are generated at an interface region of the multi-dimensional acoustic standing wave to clarify the fluid mixture as it passes through the multi-dimensional acoustic standing wave.

8. The process of claim 1, wherein the acoustic perfusion device further comprises a recirculating fluid stream that transports away cells that are held back at the interface region of the multi-dimensional acoustic standing wave.

9. The process of claim 1, wherein the multi-dimensional acoustic standing wave results in an acoustic radiation force that includes an axial force component and a lateral force component that are of the same order of magnitude.

10. The process of claim 1, wherein biomolecule aggregates that pass through the multi-dimensional acoustic standing wave are collected outside and downstream of the acoustic perfusion device.

11. The process of claim 1, wherein biomolecules recovered from the acoustic perfusion device are subjected to further processing downstream of the acoustic perfusion device.

12. The process of claim 11, wherein the further processing includes at least one of chromatography and additional filtration.

13. The process of claim 12, wherein the additional filtration includes at least one of depth filtration, crossflow filtration, tangential filtration, and sterile filtration.

14. The process of claim 1, further comprising glycoengineering the biomolecules to produce antibodies with predetermined glycoforms.

15. A process for collecting biomolecules from a cell culture, the process comprising:
 flowing a nutrient fluid stream through the cell culture to collect the biomolecules;
 flowing the nutrient fluid stream through an acoustic perfusion device, the acoustic perfusion device including at least one ultrasonic transducer including a piezoelectric material configured to generate a multi-dimensional acoustic standing wave that holds the cell culture in the acoustic perfusion device; and
 driving the ultrasonic transducer to generate the multi-dimensional acoustic standing wave and separate any biomolecule aggregates present in the nutrient fluid stream; and
 separating the biomolecules from the nutrient fluid stream.

16. The process of claim 15, wherein the biomolecules are monoclonal antibodies.

17. The process of claim 15, wherein any cells in the nutrient fluid stream are recycled back to the cell culture.

* * * * *